(12) United States Patent
Noonan et al.

(10) Patent No.: US 11,382,650 B2
(45) Date of Patent: Jul. 12, 2022

(54) OBJECT CAPTURE WITH A BASKET

(71) Applicant: Auris Health, Inc., Redwood City, CA (US)

(72) Inventors: David P. Noonan, San Francisco, CA (US); Joseph A. Urban, Jr., San Carlos, CA (US); Varun Agrawal, San Carlos, CA (US)

(73) Assignee: Auris Health, Inc., Redwood City, CA (US)

( * ) Notice: Subject to any disclaimer, the term of this patent is extended or adjusted under 35 U.S.C. 154(b) by 471 days.

(21) Appl. No.: 15/948,351

(22) Filed: Apr. 9, 2018

(65) Prior Publication Data
US 2018/0221038 A1     Aug. 9, 2018

Related U.S. Application Data

(63) Continuation of application No. 15/339,476, filed on Oct. 31, 2016, now Pat. No. 9,949,749.
(Continued)

(51) Int. Cl.
*A61B 17/221* (2006.01)
*A61B 34/30* (2016.01)
(Continued)

(52) U.S. Cl.
CPC ...... *A61B 17/320758* (2013.01); *A61B 1/018* (2013.01); *A61B 1/307* (2013.01);
(Continued)

(58) Field of Classification Search
CPC .......... A61B 17/221; A61B 2017/2212; A61B 2017/2215; A61B 2017/2217;
(Continued)

(56) References Cited

U.S. PATENT DOCUMENTS 2,556,601 A    6/1951  Schofield
2,566,183 A    8/1951  Forss
(Continued)

FOREIGN PATENT DOCUMENTS

AU    2017336790 A1    4/2019
AU    2018243364 A1    10/2019
(Continued)

OTHER PUBLICATIONS

U.S. Appl. No. 62/248,737, filed Oct. 30, 2015, Noonan et al.
(Continued)

*Primary Examiner* — Dianne Dornbusch
(74) *Attorney, Agent, or Firm* — Chang & Hale LLP

(57) ABSTRACT

A method for capturing an object in a cavity in a patient is described. The method includes advancing a ureteroscope into the cavity containing the object. A basket is advanced through a working channel of the ureteroscope. The basket is opened within the cavity and is positioned so as to enclose the object. Then, two actions are performed simultaneously. The basket is collapsed while simultaneously the basket tool is advanced forward so that the object remains within the basket, ideally near the center of the basket, as the basket closes around the object. Once the object is captured, the basket is retracted to remove the object out of the cavity. Further, this process may be automated by having the method carried out by robotic arms acting in tandem, with one or more robotic arms advancing the basket tool or ureteroscope, and another robotic arm collapsing the basket.

26 Claims, 25 Drawing Sheets

Related U.S. Application Data

(60) Provisional application No. 62/248,737, filed on Oct. 30, 2015.

(51) Int. Cl.

| | | |
|---|---|---|
| *A61B 17/3207* | (2006.01) | |
| *A61B 1/307* | (2006.01) | |
| *A61B 1/018* | (2006.01) | |
| *A61B 17/3203* | (2006.01) | |
| *A61B 34/00* | (2016.01) | |
| *A61B 18/26* | (2006.01) | |
| *A61B 18/00* | (2006.01) | |

(52) U.S. Cl.
CPC ...... *A61B 17/221* (2013.01); *A61B 17/32037* (2013.01); *A61B 18/26* (2013.01); *A61B 34/30* (2016.02); *A61B 34/71* (2016.02); *A61B 2017/2212* (2013.01); *A61B 2017/2215* (2013.01); *A61B 2018/00511* (2013.01); *A61B 2018/00517* (2013.01); *A61B 2034/301* (2016.02); *A61B 2034/302* (2016.02); *A61B 2217/005* (2013.01)

(58) Field of Classification Search
CPC .............. A61B 34/30; A61B 2034/301; A61B 2034/302; A61B 2034/303
See application file for complete search history.

(56) References Cited

U.S. PATENT DOCUMENTS

| | | | |
|---|---|---|---|
| 2,623,175 A | 12/1952 | Finke | |
| 2,730,699 A | 1/1956 | Gratian | |
| 2,884,808 A | 5/1959 | Mueller | |
| 3,294,183 A | 12/1966 | Riley et al. | |
| 3,472,083 A | 10/1969 | Schnepel | |
| 3,513,724 A | 5/1970 | Box | |
| 3,595,074 A | 7/1971 | Johnson | |
| 3,734,207 A | 5/1973 | Fishbein | |
| 3,739,923 A | 6/1973 | Totsuka | |
| 3,763,860 A | 10/1973 | Clarke | |
| 3,784,031 A | 1/1974 | Niitu et al. | |
| 3,790,002 A | 2/1974 | Guilbaud et al. | |
| 3,921,536 A | 11/1975 | Savage | |
| 3,926,386 A | 12/1975 | Stahmann et al. | |
| 4,040,413 A | 8/1977 | Ohshiro | |
| 4,141,245 A | 2/1979 | Brandstetter | |
| 4,198,960 A | 4/1980 | Utsugi | |
| 4,241,884 A | 12/1980 | Lynch | |
| 4,243,034 A | 1/1981 | Brandt | |
| 4,351,493 A | 9/1982 | Sonnek | |
| 4,357,843 A | 11/1982 | Peck et al. | |
| 4,384,493 A | 5/1983 | Grunbaum | |
| 4,470,407 A | 9/1984 | Hussein | |
| 4,507,026 A | 3/1985 | Lund | |
| 4,530,471 A | 7/1985 | Inoue | |
| 4,532,935 A | 8/1985 | Wang et al. | |
| 4,555,960 A | 12/1985 | King | |
| 4,611,594 A * | 9/1986 | Grayhack ............ | A61B 17/221 606/127 |
| 4,685,458 A | 8/1987 | Leckrone | |
| 4,688,555 A | 8/1987 | Wardle | |
| 4,741,335 A * | 5/1988 | Okada ................. | A61B 17/221 606/127 |
| 4,745,908 A | 5/1988 | Wardle | |
| 4,747,405 A | 5/1988 | Leckrone | |
| 4,784,150 A | 11/1988 | Voorhies et al. | |
| 4,854,301 A | 8/1989 | Nakajima | |
| 4,857,058 A | 8/1989 | W. | |
| 4,898,574 A | 2/1990 | Uchiyama | |
| 4,899,733 A | 2/1990 | DeCastro et al. | |
| 4,907,168 A | 3/1990 | Boggs | |
| 4,945,790 A | 8/1990 | Golden | |
| 4,983,165 A | 1/1991 | Loiterman | |
| 5,029,574 A | 7/1991 | Shimamura | |
| 5,085,659 A | 2/1992 | Rydell | |
| 5,150,452 A | 9/1992 | Pollack et al. | |
| 5,190,542 A * | 3/1993 | Nakao ............... | A61B 17/32056 606/1 |
| 5,190,557 A | 3/1993 | Borodulin et al. | |
| 5,196,023 A | 3/1993 | Martin | |
| 5,207,128 A | 5/1993 | Albright | |
| 5,217,465 A | 6/1993 | Steppe | |
| 5,234,428 A | 8/1993 | Kaufman | |
| 5,256,150 A | 10/1993 | Quiachon et al. | |
| 5,277,085 A | 1/1994 | Tanimura et al. | |
| 5,308,323 A | 5/1994 | Sogawa et al. | |
| 5,318,589 A | 6/1994 | Lichtman | |
| 5,325,848 A | 7/1994 | Adams et al. | |
| 5,342,381 A | 8/1994 | Tidemand | |
| 5,344,395 A | 9/1994 | Whalen et al. | |
| 5,350,101 A | 9/1994 | Godlewski | |
| 5,353,783 A | 10/1994 | Nakao et al. | |
| 5,370,609 A | 12/1994 | Drasler et al. | |
| 5,372,124 A | 12/1994 | Takayama et al. | |
| 5,411,016 A | 5/1995 | Kume | |
| 5,426,687 A | 6/1995 | Goodall et al. | |
| 5,431,649 A | 7/1995 | Mulier et al. | |
| 5,441,485 A | 8/1995 | Peters | |
| 5,449,356 A | 9/1995 | Waibrink | |
| 5,450,843 A | 9/1995 | Moll | |
| 5,472,426 A | 12/1995 | Bonati et al. | |
| 5,496,267 A | 3/1996 | Drasler et al. | |
| 5,501,667 A | 3/1996 | Verduin, Jr. | |
| 5,507,725 A | 4/1996 | Savage et al. | |
| 5,520,684 A | 5/1996 | Imran | |
| 5,524,180 A | 6/1996 | Wang et al. | |
| 5,545,170 A | 8/1996 | Hart | |
| 5,559,294 A | 9/1996 | Hoium et al. | |
| 5,562,239 A | 10/1996 | Boiarski et al. | |
| 5,562,648 A | 10/1996 | Peterson | |
| 5,562,678 A | 10/1996 | Booker | |
| 5,572,999 A | 11/1996 | Funda et al. | |
| 5,573,535 A | 11/1996 | Viklund | |
| 5,613,973 A | 3/1997 | Jackson et al. | |
| 5,645,083 A | 7/1997 | Essig et al. | |
| 5,653,374 A | 8/1997 | Young et al. | |
| 5,658,311 A | 8/1997 | Baden | |
| 5,695,500 A | 12/1997 | Taylor et al. | |
| 5,697,949 A | 12/1997 | Giurtino et al. | |
| 5,709,661 A | 1/1998 | Egmond et al. | |
| 5,710,870 A | 1/1998 | Ohm | |
| 5,716,325 A | 2/1998 | Bonutti | |
| 5,737,500 A | 4/1998 | Seraji et al. | |
| 5,767,840 A | 6/1998 | Selker | |
| 5,779,623 A | 7/1998 | Bonnell | |
| 5,788,667 A | 8/1998 | Stoller | |
| 5,788,710 A * | 8/1998 | Bates ................... | A61B 17/221 606/113 |
| 5,792,135 A | 8/1998 | Madhani et al. | |
| 5,792,165 A | 8/1998 | Klieman | |
| 5,797,900 A | 8/1998 | Madhani | |
| 5,798,627 A | 8/1998 | Gilliland et al. | |
| 5,810,770 A | 9/1998 | Chin | |
| 5,842,390 A | 12/1998 | Bouligny et al. | |
| 5,855,583 A | 1/1999 | Wang et al. | |
| 5,893,869 A | 4/1999 | Barnhart | |
| 5,897,491 A | 4/1999 | Kastenbauer et al. | |
| 5,921,968 A | 7/1999 | Lampropoulos et al. | |
| 5,924,175 A | 7/1999 | Lippitt | |
| 5,943,056 A | 8/1999 | Sato et al. | |
| 5,967,934 A | 10/1999 | Ishida et al. | |
| 5,969,230 A | 10/1999 | Sakai et al. | |
| 5,989,230 A | 11/1999 | Frassica | |
| 6,016,839 A | 1/2000 | Raftis | |
| 6,071,281 A | 6/2000 | Burnside et al. | |
| 6,077,219 A | 6/2000 | Ziebach et al. | |
| 6,084,371 A | 7/2000 | Kress et al. | |
| 6,093,157 A | 7/2000 | Chandrasekaran | |
| 6,110,171 A | 8/2000 | Rydell | |
| 6,120,476 A | 9/2000 | Fung et al. | |
| 6,120,498 A | 9/2000 | Jani et al. | |
| 6,154,000 A | 11/2000 | Rastegar et al. | |

(56) References Cited

U.S. PATENT DOCUMENTS

| | | |
|---|---|---|
| 6,156,030 A | 12/2000 | Neev |
| 6,159,220 A | 12/2000 | Gobron et al. |
| 6,171,234 B1 | 1/2001 | White et al. |
| 6,174,318 B1 * | 1/2001 | Bates .................. A61B 17/221 606/113 |
| 6,183,482 B1 | 2/2001 | Bates et al. |
| 6,185,478 B1 | 2/2001 | Koakutsu et al. |
| 6,206,903 B1 | 3/2001 | Ramans |
| 6,236,906 B1 | 5/2001 | Muller |
| 6,183,435 B1 | 6/2001 | Bumbalough et al. |
| 6,272,371 B1 | 8/2001 | Shlomo |
| 6,289,579 B1 | 9/2001 | Viza et al. |
| 6,302,895 B1 | 10/2001 | Gobron et al. |
| 6,322,557 B1 | 11/2001 | Nikolaevich |
| 6,375,635 B1 | 4/2002 | Moutafis |
| 6,394,998 B1 | 5/2002 | Wallace et al. |
| 6,401,572 B1 | 6/2002 | Provost |
| 6,405,078 B1 | 6/2002 | Moaddeb et al. |
| 6,428,563 B1 | 8/2002 | Keller |
| 6,436,107 B1 | 8/2002 | Wang et al. |
| 6,440,061 B1 | 8/2002 | Wenner et al. |
| 6,487,940 B2 | 12/2002 | Hart et al. |
| 6,491,701 B2 | 12/2002 | Tierney et al. |
| 6,508,823 B1 | 1/2003 | Gonon |
| 6,522,906 B1 | 2/2003 | Salisbury et al. |
| 6,577,891 B1 | 6/2003 | Jaross et al. |
| 6,659,939 B2 | 12/2003 | Moll et al. |
| 6,673,080 B2 | 1/2004 | Reynolds et al. |
| 6,676,668 B2 * | 1/2004 | Mercereau ............ A61B 17/221 606/1 |
| 6,685,698 B2 | 2/2004 | Morley et al. |
| 6,695,818 B2 | 2/2004 | Wollschlager |
| 6,706,050 B1 | 3/2004 | Giannadakis |
| 6,726,675 B1 | 4/2004 | Beyar |
| 6,786,896 B1 | 9/2004 | Madhani et al. |
| 6,827,712 B2 | 12/2004 | Tovey et al. |
| 6,991,602 B2 | 1/2006 | Nakazawa et al. |
| 7,044,936 B2 | 5/2006 | Harding et al. |
| 7,172,580 B2 | 2/2007 | Hruska et al. |
| 7,248,944 B2 | 7/2007 | Green |
| 7,276,044 B2 | 10/2007 | Ferry et al. |
| 7,282,055 B2 | 10/2007 | Tsuruta |
| 7,524,284 B2 | 4/2009 | Murakami et al. |
| 7,559,934 B2 | 7/2009 | Teague et al. |
| 7,615,042 B2 | 11/2009 | Beyar et al. |
| 7,635,342 B2 | 12/2009 | Ferry et al. |
| 7,645,283 B2 | 1/2010 | Reynolds et al. |
| 7,736,356 B2 | 6/2010 | Cooper et al. |
| 7,766,856 B2 | 8/2010 | Ferry et al. |
| 7,882,841 B2 | 2/2011 | Aljuri et al. |
| 7,914,540 B2 * | 3/2011 | Schwartz ............ A61B 17/221 606/128 |
| 7,938,809 B2 | 5/2011 | Lampropoulos et al. |
| 7,963,911 B2 | 6/2011 | Turliuc |
| 7,972,298 B2 | 7/2011 | Wallace et al. |
| 7,974,674 B2 | 7/2011 | Hauck et al. |
| 7,987,046 B1 | 7/2011 | Peterman |
| 7,998,020 B2 | 8/2011 | Kidd et al. |
| 8,002,713 B2 | 8/2011 | Heske |
| 8,004,229 B2 | 8/2011 | Nowlin et al. |
| 8,038,598 B2 | 10/2011 | Khachi |
| 8,043,303 B2 * | 10/2011 | Razvi .................. A61B 17/2909 606/113 |
| 8,052,636 B2 | 11/2011 | Moll et al. |
| 8,092,397 B2 | 1/2012 | Wallace et al. |
| 8,157,308 B2 | 4/2012 | Pedersen |
| 8,182,415 B2 | 5/2012 | Larkin et al. |
| 8,187,173 B2 | 5/2012 | Miyoshi |
| 8,257,303 B2 | 9/2012 | Moll et al. |
| 8,277,417 B2 | 10/2012 | Fedinec |
| 8,291,791 B2 | 10/2012 | Light et al. |
| 8,414,505 B1 | 4/2013 | Weitzner et al. |
| 8,425,465 B2 | 4/2013 | Nagano et al. |
| 8,480,595 B2 | 7/2013 | Speeg |
| 8,523,762 B2 | 9/2013 | Miyamoto et al. |
| 8,540,748 B2 | 9/2013 | Murphy et al. |
| 8,541,970 B2 | 9/2013 | Nowlin et al. |
| 8,602,031 B2 | 12/2013 | Reis et al. |
| 8,671,817 B1 | 3/2014 | Bogusky |
| 8,720,448 B2 | 5/2014 | Reis et al. |
| 8,746,252 B2 | 6/2014 | McGrogan et al. |
| 8,749,190 B2 | 6/2014 | Nowlin et al. |
| 8,755,124 B2 | 6/2014 | Aschwanden et al. |
| 8,786,241 B2 | 7/2014 | Nowlin et al. |
| 8,820,603 B2 | 9/2014 | Shelton et al. |
| 8,821,480 B2 | 9/2014 | Burbank |
| 8,827,948 B2 | 9/2014 | Romo et al. |
| 8,870,815 B2 | 10/2014 | Bhat et al. |
| 8,882,660 B2 | 11/2014 | Phee et al. |
| 8,894,610 B2 | 11/2014 | Macnamara et al. |
| 8,945,163 B2 | 2/2015 | Voegele et al. |
| 8,956,280 B2 | 2/2015 | Eversull et al. |
| 8,961,533 B2 | 2/2015 | Stabler et al. |
| 8,968,333 B2 | 3/2015 | Yu et al. |
| 8,992,542 B2 | 3/2015 | Hagag et al. |
| 9,173,713 B2 | 11/2015 | Hart et al. |
| 9,179,979 B2 | 11/2015 | Jinno |
| 9,204,933 B2 | 12/2015 | Reis et al. |
| 9,254,123 B2 | 2/2016 | Alvarez et al. |
| 9,259,280 B2 | 2/2016 | Au et al. |
| 9,259,281 B2 | 2/2016 | Griffiths et al. |
| 9,259,282 B2 | 2/2016 | Azizian et al. |
| 9,296,104 B2 | 3/2016 | Swarup et al. |
| 9,326,822 B2 | 5/2016 | Lewis et al. |
| 9,345,456 B2 | 5/2016 | Tsonton et al. |
| 9,345,544 B2 | 5/2016 | Hourtash et al. |
| 9,375,284 B2 | 6/2016 | Hourtash |
| 9,408,669 B2 | 8/2016 | Kokish et al. |
| 9,415,510 B2 | 8/2016 | Hourtash et al. |
| 9,446,177 B2 | 9/2016 | Millman et al. |
| 9,452,018 B2 | 9/2016 | Yu |
| 9,457,168 B2 | 10/2016 | Moll et al. |
| 9,460,536 B2 | 10/2016 | Hasegawa et al. |
| 9,480,534 B2 | 11/2016 | Bowling et al. |
| 9,498,601 B2 | 11/2016 | Tanner et al. |
| 9,504,604 B2 | 11/2016 | Alvarez |
| 9,510,911 B2 | 12/2016 | Hourtash |
| 9,517,106 B2 | 12/2016 | Hourtash et al. |
| 9,561,083 B2 | 2/2017 | Yu et al. |
| 9,566,125 B2 | 2/2017 | Bowling et al. |
| 9,592,042 B2 | 3/2017 | Titus |
| 9,597,152 B2 | 3/2017 | Schaeffer |
| 9,622,827 B2 | 4/2017 | Yu et al. |
| 9,636,184 B2 | 5/2017 | Lee et al. |
| 9,636,483 B2 | 5/2017 | Hart et al. |
| 9,668,814 B2 | 6/2017 | Kokish |
| 9,675,422 B2 | 6/2017 | Hourtash et al. |
| 9,687,310 B2 | 6/2017 | Nowlin et al. |
| 9,713,509 B2 | 7/2017 | Schuh et al. |
| 9,727,963 B2 | 8/2017 | Mintz et al. |
| 9,730,757 B2 | 8/2017 | Brudniok |
| 9,737,371 B2 | 8/2017 | Romo |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,818,681 B2 | 11/2017 | Machida |
| 9,844,412 B2 | 12/2017 | Bogusky et al. |
| 9,867,635 B2 | 1/2018 | Alvarez et al. |
| 9,918,659 B2 | 3/2018 | Chopra et al. |
| 9,918,681 B2 | 3/2018 | Wallace et al. |
| 9,931,025 B1 | 4/2018 | Graetzel et al. |
| 9,943,962 B2 | 4/2018 | Sattler et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 9,993,614 B2 | 6/2018 | Pacheco et al. |
| 10,016,900 B1 | 7/2018 | Meyer et al. |
| 10,022,192 B1 | 7/2018 | Ummalaneni |
| 10,029,367 B2 | 7/2018 | Hourtash |
| 10,046,140 B2 | 8/2018 | Kokish et al. |
| 10,071,479 B2 | 9/2018 | Swarup et al. |

(56) References Cited

U.S. PATENT DOCUMENTS

| | | |
|---|---|---|
| 10,080,576 B2 | 9/2018 | Romo et al. |
| 10,117,713 B2 | 11/2018 | Barrera et al. |
| 10,130,429 B1 | 11/2018 | Weir |
| 10,136,949 B2 | 11/2018 | Felder et al. |
| 10,136,959 B2 | 11/2018 | Mintz et al. |
| 10,143,360 B2 | 12/2018 | Roelle et al. |
| 10,145,747 B1 | 12/2018 | Lin et al. |
| 10,149,720 B2 | 12/2018 | Romo |
| 10,154,822 B2 | 12/2018 | Henderson et al. |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,176,681 B2 | 1/2019 | Plewe et al. |
| 10,213,264 B2 | 2/2019 | Tanner et al. |
| 10,219,867 B2 | 3/2019 | Saglam et al. |
| 10,219,868 B2 | 3/2019 | Weir |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,258,285 B2 | 4/2019 | Hauck et al. |
| 10,285,574 B2 | 5/2019 | Landey et al. |
| 10,299,870 B2 | 5/2019 | Connolly et al. |
| 10,314,463 B2 | 6/2019 | Agrawal et al. |
| 10,314,661 B2 | 6/2019 | Bowling et al. |
| 10,327,855 B2 | 6/2019 | Hourtash et al. |
| 10,350,017 B2 | 7/2019 | Bowling et al. |
| 10,350,390 B2 | 7/2019 | Moll et al. |
| 10,363,103 B2 | 7/2019 | Alvarez et al. |
| 10,383,765 B2 | 8/2019 | Alvarez et al. |
| 10,398,518 B2 | 9/2019 | Yu et al. |
| 10,405,939 B2 | 9/2019 | Romo |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer et al. |
| 10,454,347 B2 | 10/2019 | Covington et al. |
| 10,463,440 B2 | 11/2019 | Bowling et al. |
| 10,464,209 B2 | 11/2019 | Ho et al. |
| 10,470,830 B2 | 11/2019 | Hill et al. |
| 10,478,595 B2 | 11/2019 | Kokish |
| 10,482,599 B2 | 11/2019 | Mintz et al. |
| 10,493,239 B2 | 12/2019 | Hart et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan |
| 10,524,867 B2 | 1/2020 | Kokish et al. |
| 10,539,478 B2 | 1/2020 | Lin et al. |
| 10,543,047 B2 | 1/2020 | Yu |
| 10,543,048 B2 | 1/2020 | Noonan et al. |
| 10,555,778 B2 | 2/2020 | Ummalaneni |
| 10,556,092 B2 | 2/2020 | Yu et al. |
| 10,569,052 B2 | 2/2020 | Kokish et al. |
| 10,631,949 B2 | 4/2020 | Schuh et al. |
| 10,639,108 B2 | 5/2020 | Romo et al. |
| 10,639,109 B2 | 5/2020 | Bovay et al. |
| 10,639,114 B2 | 5/2020 | Schuh |
| 10,667,871 B2 | 6/2020 | Romo et al. |
| 10,667,875 B2 | 6/2020 | DeFonzo |
| 10,682,189 B2 | 6/2020 | Schuh et al. |
| 10,687,903 B2 | 6/2020 | Lewis et al. |
| 10,695,536 B2 | 6/2020 | Weitzner et al. |
| 10,702,348 B2 | 7/2020 | Moll et al. |
| 10,716,461 B2 | 7/2020 | Jenkins |
| 10,743,751 B2 | 8/2020 | Landey |
| 10,744,035 B2 | 8/2020 | Alvarez et al. |
| 10,751,140 B2 | 8/2020 | Wallace et al. |
| 10,765,303 B2 | 9/2020 | Graetzel et al. |
| 10,765,487 B2 | 9/2020 | Ho |
| 10,779,898 B2 | 9/2020 | Hill et al. |
| 10,786,329 B2 | 9/2020 | Schuh et al. |
| 10,786,432 B2 | 9/2020 | Jornitz et al. |
| 10,792,112 B2 | 10/2020 | Kokish et al. |
| 10,792,464 B2 | 10/2020 | Romo et al. |
| 10,792,466 B2 | 10/2020 | Landey et al. |
| 10,813,539 B2 | 10/2020 | Graetzel et al. |
| 10,814,101 B2 | 10/2020 | Jiang |
| 10,820,947 B2 | 11/2020 | Julian |
| 10,820,952 B2 | 11/2020 | Yu |
| 10,820,954 B2 | 11/2020 | Marsot et al. |
| 10,827,913 B2 | 11/2020 | Ummalaneni et al. |
| 10,828,118 B2 | 11/2020 | Schuh et al. |
| 10,835,153 B2 | 11/2020 | Rafii-Tari et al. |
| 10,850,013 B2 | 12/2020 | Hsu et al. |
| 10,881,280 B2 | 1/2021 | Baez, Jr. |
| 10,888,386 B2 | 1/2021 | Eyre et al. |
| 10,898,276 B2 | 1/2021 | Graetzel et al. |
| 2001/0042643 A1 | 11/2001 | Krueger et al. |
| 2002/0019644 A1 | 2/2002 | Hastings et al. |
| 2002/0045905 A1 | 4/2002 | Gerbi et al. |
| 2002/0068954 A1* | 6/2002 | Foster ................. A61B 17/221 606/200 |
| 2002/0098938 A1 | 7/2002 | Milbourne et al. |
| 2002/0100254 A1 | 8/2002 | Dharssi |
| 2002/0107573 A1 | 8/2002 | Steinberg |
| 2002/0111608 A1 | 8/2002 | Baerveldt et al. |
| 2002/0111621 A1 | 8/2002 | Wallace et al. |
| 2002/0117017 A1 | 8/2002 | Bernhardt et al. |
| 2002/0161355 A1 | 10/2002 | Wollschlager |
| 2002/0161426 A1 | 10/2002 | Iancea |
| 2002/0177789 A1 | 11/2002 | Ferry et al. |
| 2003/0004455 A1 | 1/2003 | Kadziauskas et al. |
| 2003/0040681 A1 | 2/2003 | Ng et al. |
| 2003/0056561 A1 | 3/2003 | Butscher et al. |
| 2003/0065358 A1 | 4/2003 | Frecker et al. |
| 2003/0088254 A1* | 5/2003 | Gregory, Jr. ......... A61B 17/221 606/127 |
| 2003/0100882 A1 | 5/2003 | Beden et al. |
| 2003/0109780 A1 | 6/2003 | Coste-Maniere et al. |
| 2003/0109877 A1 | 6/2003 | Morley et al. |
| 2003/0109889 A1* | 6/2003 | Mercereau ........... A61B 17/221 606/127 |
| 2003/0158545 A1 | 8/2003 | Hovda et al. |
| 2003/0167623 A1 | 9/2003 | Lorenz |
| 2003/0208189 A1 | 11/2003 | Payman |
| 2003/0212308 A1 | 11/2003 | Bendall |
| 2003/0225419 A1* | 12/2003 | Lippitt ................. A61B 17/221 606/127 |
| 2004/0015053 A1 | 1/2004 | Bieger et al. |
| 2004/0122444 A1 | 6/2004 | Gerard |
| 2004/0143253 A1 | 7/2004 | Vanney et al. |
| 2004/0152972 A1 | 8/2004 | Hunter |
| 2004/0153093 A1 | 8/2004 | Donovan |
| 2004/0158261 A1 | 8/2004 | Vu |
| 2004/0186349 A1 | 9/2004 | Ewers et al. |
| 2004/0193146 A1 | 9/2004 | Lee et al. |
| 2004/0210116 A1 | 10/2004 | Nakao et al. |
| 2004/0243147 A1 | 12/2004 | Lipow |
| 2004/0253079 A1 | 12/2004 | Sanchez |
| 2004/0254566 A1 | 12/2004 | Plicchi et al. |
| 2004/0260246 A1 | 12/2004 | Desmond |
| 2005/0004579 A1 | 1/2005 | Schneider et al. |
| 2005/0033270 A1 | 2/2005 | Ramans et al. |
| 2005/0054900 A1 | 3/2005 | Mawn et al. |
| 2005/0059645 A1 | 3/2005 | Bodor |
| 2005/0159645 A1 | 7/2005 | Bertolero et al. |
| 2005/0177026 A1 | 8/2005 | Hoeg et al. |
| 2005/0183532 A1 | 8/2005 | Najafi et al. |
| 2005/0222554 A1 | 10/2005 | Wallace et al. |
| 2005/0240178 A1 | 10/2005 | Morley et al. |
| 2005/0261705 A1* | 11/2005 | Gist ..................... A61B 17/221 606/113 |
| 2005/0267488 A1* | 12/2005 | Hare .................... A61B 17/221 606/113 |
| 2006/0015133 A1 | 1/2006 | Grayzel et al. |
| 2006/0041245 A1 | 2/2006 | Ferry et al. |
| 2006/0058813 A1* | 3/2006 | Teague ............. A61B 17/32056 606/113 |
| 2006/0111692 A1 | 5/2006 | Hlavka et al. |
| 2006/0116693 A1* | 6/2006 | Weisenburgh ... A61B 17/22031 606/128 |
| 2006/0135963 A1 | 6/2006 | Kick et al. |

(56) References Cited

U.S. PATENT DOCUMENTS

| | | |
|---|---|---|
| 2006/0142657 A1 | 6/2006 | Quaid et al. |
| 2006/0146010 A1 | 7/2006 | Schneider |
| 2006/0156875 A1 | 7/2006 | Mcrury et al. |
| 2006/0161137 A1 | 7/2006 | Orban et al. |
| 2006/0189891 A1 | 8/2006 | Waxman et al. |
| 2006/0201688 A1 | 9/2006 | Jenner et al. |
| 2006/0229587 A1 | 10/2006 | Beyar et al. |
| 2006/0237205 A1 | 10/2006 | Sia et al. |
| 2007/0000498 A1 | 1/2007 | Glynn et al. |
| 2007/0000577 A1 | 1/2007 | Chen |
| 2007/0013336 A1 | 1/2007 | Nowlin et al. |
| 2007/0016164 A1 | 1/2007 | Dudney et al. |
| 2007/0021768 A1 | 1/2007 | Nance et al. |
| 2007/0027443 A1 | 2/2007 | Rose et al. |
| 2007/0027534 A1 | 2/2007 | Bergheim et al. |
| 2007/0032906 A1 | 2/2007 | Sutherland et al. |
| 2007/0060879 A1 | 3/2007 | Weitzner et al. |
| 2007/0086934 A1 | 4/2007 | Huber et al. |
| 2007/0100201 A1 | 5/2007 | Komiya et al. |
| 2007/0100254 A1 | 5/2007 | Murakami et al. |
| 2007/0106304 A1* | 5/2007 | Hammack ........... A61B 17/8014 606/113 |
| 2007/0112355 A1 | 5/2007 | Salahieh et al. |
| 2007/0119274 A1 | 5/2007 | Devengenzo et al. |
| 2007/0123855 A1 | 5/2007 | Morley et al. |
| 2007/0135803 A1 | 6/2007 | Belson |
| 2007/0149946 A1 | 6/2007 | Viswanathan et al. |
| 2007/0185485 A1 | 8/2007 | Hauck et al. |
| 2007/0191177 A1 | 8/2007 | Nagai et al. |
| 2007/0203475 A1 | 8/2007 | Fischer et al. |
| 2007/0208252 A1 | 9/2007 | Makower |
| 2007/0208375 A1 | 9/2007 | Nishizawa |
| 2007/0213668 A1 | 9/2007 | Spitz |
| 2007/0239028 A1 | 10/2007 | Houser et al. |
| 2007/0239178 A1 | 10/2007 | Weitzner et al. |
| 2007/0245175 A1 | 10/2007 | Zheng et al. |
| 2007/0250111 A1 | 10/2007 | Lu et al. |
| 2007/0299427 A1 | 12/2007 | Yeung et al. |
| 2008/0009884 A1* | 1/2008 | Kennedy ............... A61B 17/221 606/127 |
| 2008/0015566 A1 | 1/2008 | Livneh et al. |
| 2008/0021440 A1 | 1/2008 | Solomon et al. |
| 2008/0027464 A1 | 1/2008 | Moll et al. |
| 2008/0033467 A1* | 2/2008 | Miyamoto ....... A61B 17/320725 606/180 |
| 2008/0039255 A1 | 2/2008 | Jinno et al. |
| 2008/0045981 A1 | 2/2008 | Margolin et al. |
| 2008/0046122 A1 | 2/2008 | Manzo et al. |
| 2008/0065103 A1 | 3/2008 | Cooper et al. |
| 2008/0065111 A1 | 3/2008 | Blumenkranz et al. |
| 2008/0065112 A1 | 3/2008 | Tovey et al. |
| 2008/0082109 A1 | 4/2008 | Moll et al. |
| 2008/0091215 A1* | 4/2008 | Saleh ................... A61B 18/14 606/113 |
| 2008/0125698 A1 | 5/2008 | Gerg et al. |
| 2008/0147011 A1 | 6/2008 | Urmey |
| 2008/0177277 A1 | 7/2008 | Huang et al. |
| 2008/0177285 A1 | 7/2008 | Brock et al. |
| 2008/0187101 A1 | 8/2008 | Gertner |
| 2008/0188864 A1* | 8/2008 | Ducharme ........... A61B 17/221 606/127 |
| 2008/0196533 A1 | 8/2008 | Bergamasco et al. |
| 2008/0214925 A1 | 9/2008 | Wilson et al. |
| 2008/0228104 A1 | 9/2008 | Uber et al. |
| 2008/0243064 A1 | 10/2008 | Stahler et al. |
| 2008/0249536 A1 | 10/2008 | Stahler et al. |
| 2008/0253108 A1 | 10/2008 | Eilenburg et al. |
| 2008/0262301 A1 | 10/2008 | Gibbons et al. |
| 2008/0262480 A1 | 10/2008 | Stahler et al. |
| 2008/0262513 A1 | 10/2008 | Stahler et al. |
| 2008/0287963 A1 | 11/2008 | Rogers et al. |
| 2008/0300592 A1 | 12/2008 | Weitzner et al. |
| 2008/0302200 A1 | 12/2008 | Tobey |
| 2008/0312521 A1 | 12/2008 | Solomon |
| 2009/0005768 A1 | 1/2009 | Sharareh et al. |
| 2009/0012507 A1 | 1/2009 | Culbertson et al. |
| 2009/0030446 A1 | 1/2009 | Measamer |
| 2009/0036900 A1 | 2/2009 | Moll |
| 2009/0043305 A1 | 2/2009 | Brodbeck et al. |
| 2009/0062602 A1 | 3/2009 | Rosenberg et al. |
| 2009/0082634 A1 | 3/2009 | Kathrani et al. |
| 2009/0082722 A1 | 3/2009 | Munger et al. |
| 2009/0088774 A1 | 4/2009 | Swarup et al. |
| 2009/0098971 A1 | 4/2009 | Ho et al. |
| 2009/0105645 A1 | 4/2009 | Kidd et al. |
| 2009/0105723 A1 | 4/2009 | Dillinger |
| 2009/0131885 A1 | 5/2009 | Akahoshi |
| 2009/0138025 A1 | 5/2009 | Stahler et al. |
| 2009/0161827 A1 | 6/2009 | Gertner et al. |
| 2009/0163948 A1 | 6/2009 | Sunaoshi et al. |
| 2009/0171371 A1 | 7/2009 | Nixon et al. |
| 2009/0192510 A1* | 7/2009 | Bahney ............... A61B 17/221 606/45 |
| 2009/0192524 A1 | 7/2009 | Itkowitz et al. |
| 2009/0227998 A1 | 9/2009 | Aljuri |
| 2009/0247944 A1 | 10/2009 | Kirschenman et al. |
| 2009/0248039 A1 | 10/2009 | Cooper et al. |
| 2009/0248041 A1 | 10/2009 | Williams et al. |
| 2009/0248043 A1 | 10/2009 | Tierney et al. |
| 2009/0264878 A1 | 10/2009 | Carmel et al. |
| 2009/0270760 A1 | 10/2009 | Leimbach et al. |
| 2009/0287188 A1 | 11/2009 | Golden et al. |
| 2009/0299352 A1 | 12/2009 | Zerfas et al. |
| 2009/0312773 A1 | 12/2009 | Cabrera et al. |
| 2010/0004642 A1 | 1/2010 | Lumpkin |
| 2010/0010504 A1 | 1/2010 | Simaan et al. |
| 2010/0011900 A1 | 1/2010 | Burbank |
| 2010/0011901 A1 | 1/2010 | Burbank |
| 2010/0016852 A1 | 1/2010 | Manzo et al. |
| 2010/0016853 A1 | 1/2010 | Burbank |
| 2010/0030023 A1 | 2/2010 | Yoshie |
| 2010/0069833 A1 | 3/2010 | Wenderow et al. |
| 2010/0073150 A1 | 3/2010 | Olson et al. |
| 2010/0081965 A1 | 4/2010 | Mugan et al. |
| 2010/0082017 A1 | 4/2010 | Zickler et al. |
| 2010/0082041 A1 | 4/2010 | Prisco |
| 2010/0125284 A1 | 5/2010 | Tanner et al. |
| 2010/0130923 A1 | 5/2010 | Cleary et al. |
| 2010/0130987 A1 | 5/2010 | Wenderow et al. |
| 2010/0137846 A1 | 6/2010 | Desai et al. |
| 2010/0175701 A1 | 7/2010 | Reis et al. |
| 2010/0179632 A1 | 7/2010 | Bruszewski et al. |
| 2010/0204605 A1 | 8/2010 | Blakley et al. |
| 2010/0204646 A1 | 8/2010 | Plicchi et al. |
| 2010/0210923 A1 | 8/2010 | Li et al. |
| 2010/0217235 A1 | 8/2010 | Thorstenson et al. |
| 2010/0225209 A1 | 9/2010 | Goldberg et al. |
| 2010/0228191 A1 | 9/2010 | Alvarez et al. |
| 2010/0228249 A1 | 9/2010 | Mohr et al. |
| 2010/0248177 A1 | 9/2010 | Mangelberger et al. |
| 2010/0249506 A1 | 9/2010 | Prisco |
| 2010/0268211 A1 | 10/2010 | Manwaring et al. |
| 2010/0274078 A1 | 10/2010 | Kim et al. |
| 2010/0312141 A1 | 12/2010 | Keast et al. |
| 2010/0331856 A1 | 12/2010 | Carlson et al. |
| 2010/0331858 A1 | 12/2010 | Simaan et al. |
| 2010/0332033 A1 | 12/2010 | Diolaiti et al. |
| 2011/0009863 A1 | 1/2011 | Marczyk et al. |
| 2011/0015483 A1* | 1/2011 | Barbagli ............... A61B 34/30 600/108 |
| 2011/0015484 A1 | 1/2011 | Alvarez et al. |
| 2011/0015648 A1 | 1/2011 | Alvarez et al. |
| 2011/0015650 A1 | 1/2011 | Choi et al. |
| 2011/0028790 A1 | 2/2011 | Farr et al. |
| 2011/0028991 A1 | 2/2011 | Ikeda et al. |
| 2011/0071541 A1 | 3/2011 | Prisco et al. |
| 2011/0071543 A1 | 3/2011 | Prisco et al. |
| 2011/0106146 A1 | 5/2011 | Jeong |
| 2011/0125165 A1 | 5/2011 | Simaan et al. |
| 2011/0130718 A1 | 6/2011 | Kidd et al. |
| 2011/0147030 A1 | 6/2011 | Blum et al. |
| 2011/0152880 A1 | 6/2011 | Alvarez et al. |
| 2011/0160713 A1 | 6/2011 | Neuberger |

(56) References Cited

U.S. PATENT DOCUMENTS

| | | |
|---|---|---|
| 2011/0160745 A1 | 6/2011 | Fielding et al. |
| 2011/0167611 A1 | 7/2011 | Williams |
| 2011/0184391 A1 | 7/2011 | Aljuri et al. |
| 2011/0208211 A1 | 8/2011 | Whitfield et al. |
| 2011/0213362 A1 | 9/2011 | Cunningham et al. |
| 2011/0224660 A1 | 9/2011 | Neuberger et al. |
| 2011/0238064 A1 | 9/2011 | Williams et al. |
| 2011/0238083 A1 | 9/2011 | Moll et al. |
| 2011/0257641 A1 | 10/2011 | Hastings et al. |
| 2011/0261183 A1 | 10/2011 | Ma et al. |
| 2011/0270273 A1 | 11/2011 | Moll et al. |
| 2011/0276085 A1 | 11/2011 | Krzyzanowski |
| 2011/0277775 A1 | 11/2011 | Holop et al. |
| 2011/0288573 A1 | 11/2011 | Fates et al. |
| 2011/0306836 A1 | 12/2011 | Ohline et al. |
| 2011/0313343 A1 | 12/2011 | Milutinovic et al. |
| 2012/0048759 A1 | 3/2012 | Disch et al. |
| 2012/0069167 A1 | 3/2012 | Liu et al. |
| 2012/0071821 A1 | 3/2012 | Yu |
| 2012/0071894 A1 | 3/2012 | Fanner et al. |
| 2012/0071895 A1 | 3/2012 | Stabler et al. |
| 2012/0132018 A1 | 5/2012 | Fang et al. |
| 2012/0136419 A1 | 5/2012 | Zarembo et al. |
| 2012/0138586 A1 | 6/2012 | Webster et al. |
| 2012/0138660 A1 | 6/2012 | Shelton, IV et al. |
| 2012/0143226 A1 | 6/2012 | Belson et al. |
| 2012/0150154 A1 | 6/2012 | Brisson et al. |
| 2012/0186194 A1 | 7/2012 | Schlieper |
| 2012/0191107 A1 | 7/2012 | Fanner et al. |
| 2012/0209315 A1 | 8/2012 | Amat |
| 2012/0217457 A1 | 8/2012 | Schena et al. |
| 2012/0232342 A1 | 9/2012 | Reydel |
| 2012/0232476 A1 | 9/2012 | Bhat et al. |
| 2012/0239012 A1 | 9/2012 | Laurent et al. |
| 2012/0253277 A1 | 10/2012 | Tah et al. |
| 2012/0253332 A1 | 10/2012 | Moll |
| 2012/0259320 A1 | 10/2012 | Loesel et al. |
| 2012/0277730 A1 | 11/2012 | Salahieh et al. |
| 2012/0283747 A1 | 11/2012 | Popovic |
| 2012/0296318 A1 | 11/2012 | Wellhoefer et al. |
| 2013/0006144 A1 | 1/2013 | Clancy et al. |
| 2013/0018400 A1 | 1/2013 | Milton et al. |
| 2013/0035537 A1 | 2/2013 | Wallace et al. |
| 2013/0053877 A1 | 2/2013 | BenMaamer |
| 2013/0066136 A1 | 3/2013 | Palese et al. |
| 2013/0066335 A1 | 3/2013 | Barwinkel et al. |
| 2013/0085442 A1 | 4/2013 | Shtul et al. |
| 2013/0085486 A1 | 4/2013 | Boutoussov et al. |
| 2013/0096422 A1 | 4/2013 | Boctor et al. |
| 2013/0096574 A1 | 4/2013 | Kang et al. |
| 2013/0110042 A1 | 5/2013 | Humphreys |
| 2013/0110107 A1 | 5/2013 | Smith et al. |
| 2013/0116716 A1 | 5/2013 | Bahls et al. |
| 2013/0144116 A1 | 6/2013 | Cooper et al. |
| 2013/0144274 A1 | 6/2013 | Stefanchik et al. |
| 2013/0144395 A1 | 6/2013 | Stefanchik |
| 2013/0190741 A1 | 7/2013 | Moll et al. |
| 2013/0190796 A1 | 7/2013 | Tilson et al. |
| 2013/0204124 A1 | 8/2013 | Duindam et al. |
| 2013/0225997 A1 | 8/2013 | Dillard et al. |
| 2013/0226151 A1 | 8/2013 | Suehara |
| 2013/0226161 A1 | 8/2013 | Hickenbotham |
| 2013/0231678 A1 | 9/2013 | Wenderow et al. |
| 2013/0233908 A1 | 9/2013 | Knodel |
| 2013/0253267 A1 | 9/2013 | Collins |
| 2013/0303876 A1 | 11/2013 | Gelfand et al. |
| 2013/0304084 A1 | 11/2013 | Beira et al. |
| 2013/0310819 A1 | 11/2013 | Neuberger et al. |
| 2013/0317519 A1 | 11/2013 | Romo et al. |
| 2013/0334281 A1 | 12/2013 | Williams |
| 2013/0345519 A1 | 12/2013 | Piskun et al. |
| 2013/0345686 A1 | 12/2013 | Brown et al. |
| 2014/0000411 A1 | 1/2014 | Shelton, IV et al. |
| 2014/0005681 A1 | 1/2014 | Gee et al. |
| 2014/0039517 A1 | 2/2014 | Bowling et al. |
| 2014/0039681 A1 | 2/2014 | Bowling et al. |
| 2014/0046308 A1 | 2/2014 | Bischoff et al. |
| 2014/0051985 A1 | 2/2014 | Fan et al. |
| 2014/0058365 A1 | 2/2014 | Bille et al. |
| 2014/0058404 A1 | 2/2014 | Hammack et al. |
| 2014/0058428 A1 | 2/2014 | Christopher et al. |
| 2014/0066944 A1 | 3/2014 | Taylor et al. |
| 2014/0069437 A1 | 3/2014 | Reis et al. |
| 2014/0100445 A1 | 4/2014 | Stenzel et al. |
| 2014/0142591 A1 | 5/2014 | Alvarez et al. |
| 2014/0163318 A1 | 6/2014 | Swanstrom |
| 2014/0163736 A1 | 6/2014 | Azizian et al. |
| 2014/0166023 A1 | 6/2014 | Kishi |
| 2014/0171778 A1 | 6/2014 | Tsusaka et al. |
| 2014/0180063 A1 | 6/2014 | Zhao et al. |
| 2014/0194859 A1 | 7/2014 | Tanchulev |
| 2014/0194905 A1 | 7/2014 | Kappel |
| 2014/0222019 A1 | 8/2014 | Brudniok |
| 2014/0222207 A1 | 8/2014 | Bowling et al. |
| 2014/0243849 A1 | 8/2014 | Saglam et al. |
| 2014/0246473 A1 | 9/2014 | Auld |
| 2014/0257333 A1 | 9/2014 | Blumenkranz |
| 2014/0275956 A1 | 9/2014 | Fan et al. |
| 2014/0276233 A1 | 9/2014 | Murphy |
| 2014/0276389 A1 | 9/2014 | Walker |
| 2014/0276394 A1 | 9/2014 | Wong et al. |
| 2014/0276594 A1 | 9/2014 | Tanner et al. |
| 2014/0276723 A1 | 9/2014 | Parihar et al. |
| 2014/0276935 A1 | 9/2014 | Yu |
| 2014/0276936 A1 | 9/2014 | Kokish et al. |
| 2014/0276956 A1 | 9/2014 | Crainich |
| 2014/0277334 A1 | 9/2014 | Yu et al. |
| 2014/0309649 A1 | 10/2014 | Alvarez et al. |
| 2014/0309655 A1* | 10/2014 | Gal ............ A61B 34/20 606/127 |
| 2014/0316203 A1 | 10/2014 | Carroux et al. |
| 2014/0357984 A1 | 12/2014 | Wallace et al. |
| 2014/0364870 A1 | 12/2014 | Alvarez et al. |
| 2014/0375784 A1 | 12/2014 | Massetti |
| 2014/0379000 A1 | 12/2014 | Romo et al. |
| 2015/0012134 A1 | 1/2015 | Robinson et al. |
| 2015/0028195 A1 | 1/2015 | King et al. |
| 2015/0051592 A1 | 2/2015 | Kintz |
| 2015/0073439 A1 | 3/2015 | Dannaher |
| 2015/0080879 A1 | 3/2015 | Trees |
| 2015/0090063 A1 | 4/2015 | Lantermann et al. |
| 2015/0101442 A1 | 4/2015 | Romo |
| 2015/0119634 A1 | 4/2015 | Jones |
| 2015/0119638 A1 | 4/2015 | Yu et al. |
| 2015/0127045 A1 | 5/2015 | Prestel |
| 2015/0133960 A1 | 5/2015 | Lohmeier |
| 2015/0133963 A1 | 5/2015 | Barbagli |
| 2015/0142013 A1 | 5/2015 | Tanner et al. |
| 2015/0144514 A1 | 5/2015 | Brennan et al. |
| 2015/0148600 A1 | 5/2015 | Ashinuma et al. |
| 2015/0150635 A1 | 6/2015 | Kilroy et al. |
| 2015/0164522 A1 | 6/2015 | Budiman |
| 2015/0164594 A1 | 6/2015 | Romo et al. |
| 2015/0164595 A1 | 6/2015 | Bogusky et al. |
| 2015/0164596 A1 | 6/2015 | Romo et al. |
| 2015/0182250 A1 | 7/2015 | Conlon et al. |
| 2015/0190204 A1 | 7/2015 | Popovi |
| 2015/0201917 A1 | 7/2015 | Snow et al. |
| 2015/0202085 A1 | 7/2015 | Lemonis et al. |
| 2015/0231364 A1 | 8/2015 | Blanchard et al. |
| 2015/0314110 A1 | 11/2015 | Park |
| 2015/0335480 A1 | 11/2015 | Alvarez et al. |
| 2015/0366629 A1 | 12/2015 | Bowling et al. |
| 2015/0374445 A1 | 12/2015 | Gombert et al. |
| 2015/0374446 A1 | 12/2015 | Malackowski et al. |
| 2016/0000512 A1 | 1/2016 | Gombert et al. |
| 2016/0001038 A1 | 1/2016 | Romo et al. |
| 2016/0022289 A1 | 1/2016 | Wan et al. |
| 2016/0022466 A1 | 1/2016 | Pedtke |
| 2016/0030073 A1 | 2/2016 | Isakov et al. |
| 2016/0045208 A1 | 2/2016 | Giulia |
| 2016/0051318 A1 | 2/2016 | Manzo et al. |
| 2016/0066935 A1 | 3/2016 | Nguyen et al. |
| 2016/0124220 A1 | 5/2016 | Bueeler et al. |

(56) References Cited

U.S. PATENT DOCUMENTS

| | | |
|---|---|---|
| 2016/0151122 A1 | 6/2016 | Alvarez et al. |
| 2016/0157945 A1 | 6/2016 | Madhani et al. |
| 2016/0158490 A1 | 6/2016 | Leeflang et al. |
| 2016/0166234 A1 | 6/2016 | Zhang et al. |
| 2016/0183841 A1 | 6/2016 | Duindam et al. |
| 2016/0184032 A1 | 6/2016 | Romo et al. |
| 2016/0192860 A1 | 7/2016 | Allenby et al. |
| 2016/0199984 A1 | 7/2016 | Lohmeier et al. |
| 2016/0206389 A1 | 7/2016 | Miller et al. |
| 2016/0213435 A1 | 7/2016 | Hourtash et al. |
| 2016/0235478 A1* | 8/2016 | Bonneau ............ A61B 18/245 |
| 2016/0235495 A1 | 8/2016 | Wallace et al. |
| 2016/0242858 A1 | 8/2016 | Barrera et al. |
| 2016/0249932 A1 | 9/2016 | Rogers et al. |
| 2016/0270865 A1 | 9/2016 | Landey et al. |
| 2016/0270866 A1 | 9/2016 | Yu et al. |
| 2016/0279394 A1 | 9/2016 | Moll et al. |
| 2016/0287279 A1 | 10/2016 | Bovay et al. |
| 2016/0287840 A1 | 10/2016 | Jiang |
| 2016/0296294 A1 | 10/2016 | Moll et al. |
| 2016/0302871 A1 | 10/2016 | Gregerson et al. |
| 2016/0303743 A1 | 10/2016 | Rockrohr |
| 2016/0310146 A1 | 10/2016 | Levy et al. |
| 2016/0331358 A1 | 11/2016 | Gordon et al. |
| 2016/0338783 A1 | 11/2016 | Romo et al. |
| 2016/0338785 A1 | 11/2016 | Kokish et al. |
| 2016/0346049 A1 | 12/2016 | Mien et al. |
| 2016/0367324 A1 | 12/2016 | Sato et al. |
| 2016/0374541 A1 | 12/2016 | Agrawal et al. |
| 2017/0000577 A1 | 1/2017 | Bowling et al. |
| 2017/0007279 A1 | 1/2017 | Sharma |
| 2017/0007337 A1 | 1/2017 | Dan |
| 2017/0020615 A1 | 1/2017 | Koenig et al. |
| 2017/0049471 A1 | 2/2017 | Gaffney et al. |
| 2017/0055995 A1 | 3/2017 | Weir et al. |
| 2017/0065227 A1 | 3/2017 | Marrs et al. |
| 2017/0065357 A1 | 3/2017 | Schuh |
| 2017/0065363 A1 | 3/2017 | Schuh et al. |
| 2017/0065364 A1 | 3/2017 | Schuh et al. |
| 2017/0065365 A1 | 3/2017 | Schuh |
| 2017/0071584 A1 | 3/2017 | Suigetsu et al. |
| 2017/0086934 A1 | 3/2017 | Devengenzo et al. |
| 2017/0095234 A1 | 4/2017 | Prisco et al. |
| 2017/0095295 A1 | 4/2017 | Overmyer et al. |
| 2017/0100199 A1 | 4/2017 | Yu et al. |
| 2017/0119411 A1 | 5/2017 | Shah |
| 2017/0119412 A1 | 5/2017 | Noonan et al. |
| 2017/0119413 A1 | 5/2017 | Romo |
| 2017/0119481 A1 | 5/2017 | Romo et al. |
| 2017/0135706 A1 | 5/2017 | Frey |
| 2017/0151028 A1 | 6/2017 | Ogawa et al. |
| 2017/0151416 A1 | 6/2017 | Kutikov |
| 2017/0165009 A1 | 6/2017 | Chaplin et al. |
| 2017/0165011 A1 | 6/2017 | Bovay et al. |
| 2017/0172553 A1 | 6/2017 | Chaplin |
| 2017/0172673 A1 | 6/2017 | Yu et al. |
| 2017/0172680 A1 | 6/2017 | Bowling et al. |
| 2017/0202627 A1 | 7/2017 | Sramek et al. |
| 2017/0202827 A1 | 7/2017 | Genkin et al. |
| 2017/0209073 A1 | 7/2017 | Sramek et al. |
| 2017/0252096 A1 | 9/2017 | Felder |
| 2017/0258534 A1 | 9/2017 | Hourtash et al. |
| 2017/0265923 A1 | 9/2017 | Privitera |
| 2017/0265954 A1 | 9/2017 | Burbank |
| 2017/0281049 A1 | 10/2017 | Yamamoto et al. |
| 2017/0290631 A1 | 10/2017 | Lee et al. |
| 2017/0319289 A1 | 11/2017 | Neff |
| 2017/0325932 A1 | 11/2017 | Hoelzle |
| 2017/0333147 A1 | 11/2017 | Bernstein |
| 2017/0333679 A1 | 11/2017 | Jiang |
| 2017/0340396 A1 | 11/2017 | Romo et al. |
| 2017/0365055 A1 | 12/2017 | Mintz et al. |
| 2017/0367782 A1 | 12/2017 | Schuh et al. |
| 2018/0000563 A1 | 1/2018 | Shanjani et al. |
| 2018/0025666 A1 | 1/2018 | Ho et al. |
| 2018/0042464 A1 | 2/2018 | Arai et al. |
| 2018/0042686 A1 | 2/2018 | Peine |
| 2018/0049792 A1 | 2/2018 | Eckert et al. |
| 2018/0049824 A1 | 2/2018 | Harris |
| 2018/0055583 A1 | 3/2018 | Schuh et al. |
| 2018/0056044 A1 | 3/2018 | Choi et al. |
| 2018/0079090 A1 | 3/2018 | Koenig et al. |
| 2018/0080841 A1 | 3/2018 | Cordoba et al. |
| 2018/0104820 A1 | 4/2018 | Troy et al. |
| 2018/0116735 A1 | 5/2018 | Tierney et al. |
| 2018/0140371 A1 | 5/2018 | Hares et al. |
| 2018/0168681 A1 | 6/2018 | Kirk et al. |
| 2018/0177383 A1 | 6/2018 | Noonan et al. |
| 2018/0177556 A1 | 6/2018 | Noonan |
| 2018/0177561 A1 | 6/2018 | Mintz et al. |
| 2018/0193049 A1 | 7/2018 | Heck et al. |
| 2018/0206927 A1 | 7/2018 | Prisco et al. |
| 2018/0206931 A1 | 7/2018 | Scheib |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0243048 A1 | 8/2018 | Shan et al. |
| 2018/0250083 A1 | 9/2018 | Schuh et al. |
| 2018/0250085 A1 | 9/2018 | Simi et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289431 A1 | 10/2018 | Draper et al. |
| 2018/0296285 A1 | 10/2018 | Simi et al. |
| 2018/0296299 A1 | 10/2018 | Iceman |
| 2018/0303566 A1 | 10/2018 | Soundararajan et al. |
| 2018/0325499 A1 | 11/2018 | Landey et al. |
| 2018/0326181 A1 | 11/2018 | Kokish et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000576 A1 | 1/2019 | Mintz et al. |
| 2019/0015166 A1 | 1/2019 | Mahoney et al. |
| 2019/0017320 A1 | 1/2019 | Lombardini |
| 2019/0069962 A1 | 3/2019 | Tabandeh et al. |
| 2019/0083183 A1 | 3/2019 | Moll et al. |
| 2019/0099231 A1 | 4/2019 | Bruehwiler |
| 2019/0099232 A1 | 4/2019 | Soto et al. |
| 2019/0105776 A1 | 4/2019 | Ho et al. |
| 2019/0105785 A1 | 4/2019 | Meyer et al. |
| 2019/0107454 A1 | 4/2019 | Lin et al. |
| 2019/0110839 A1 | 4/2019 | Rafii-Tari et al. |
| 2019/0110843 A1 | 4/2019 | Ummalaneni |
| 2019/0117324 A1 | 4/2019 | Hibner et al. |
| 2019/0125465 A1 | 5/2019 | Evans et al. |
| 2019/0142537 A1 | 5/2019 | Covington |
| 2019/0151148 A1 | 5/2019 | Alvarez et al. |
| 2019/0167366 A1 | 6/2019 | Ummalaneni et al. |
| 2019/0175009 A1 | 6/2019 | Mintz et al. |
| 2019/0175062 A1 | 6/2019 | Rafii-Tari et al. |
| 2019/0175287 A1 | 6/2019 | Hill et al. |
| 2019/0175799 A1 | 6/2019 | Hsu et al. |
| 2019/0183585 A1 | 6/2019 | Rafii-Tari et al. |
| 2019/0183587 A1 | 6/2019 | Rafii-Tari et al. |
| 2019/0191967 A1 | 6/2019 | Yamamoto et al. |
| 2019/0192249 A1 | 6/2019 | Bowling et al. |
| 2019/0216548 A1 | 7/2019 | Ummalaneni |
| 2019/0216550 A1 | 7/2019 | Eyre et al. |
| 2019/0216576 A1 | 7/2019 | Eyre et al. |
| 2019/0223967 A1 | 7/2019 | Abbott et al. |
| 2019/0223974 A1 | 7/2019 | Romo et al. |
| 2019/0228525 A1 | 7/2019 | Mintz et al. |
| 2019/0228528 A1 | 7/2019 | Mintz et al. |
| 2019/0231458 A1 | 8/2019 | DiMaio et al. |
| 2019/0231460 A1 | 8/2019 | DiMaio et al. |
| 2019/0239890 A1 | 8/2019 | Stokes |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |

(56) References Cited

U.S. PATENT DOCUMENTS

| | | |
|---|---|---|
| 2019/0298460 A1 | 10/2019 | Al-Jadda |
| 2019/0298464 A1 | 10/2019 | Abbott |
| 2019/0298465 A1 | 10/2019 | Chin |
| 2019/0298469 A1 | 10/2019 | Ramstad et al. |
| 2019/0314616 A1 | 10/2019 | Moll et al. |
| 2019/0328213 A1 | 10/2019 | Landey et al. |
| 2019/0336238 A1 | 11/2019 | Yu |
| 2019/0365201 A1 | 12/2019 | Noonan et al. |
| 2019/0365209 A1 | 12/2019 | Ye et al. |
| 2019/0365479 A1 | 12/2019 | Rafii-Tar |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000533 A1 | 1/2020 | Schuh |
| 2020/0000855 A1 | 1/2020 | Ku et al. |
| 2020/0008874 A1 | 1/2020 | Barbagli |
| 2020/0022767 A1 | 1/2020 | Hill |
| 2020/0030046 A1 | 1/2020 | Bowling et al. |
| 2020/0034526 A1 | 1/2020 | Asokan et al. |
| 2020/0038123 A1 | 2/2020 | Graetzel |
| 2020/0039086 A1 | 2/2020 | Meyer |
| 2020/0040537 A1 | 2/2020 | Groeneweg |
| 2020/0046434 A1 | 2/2020 | Graetzel |
| 2020/0054408 A1 | 2/2020 | Schuh et al. |
| 2020/0055801 A1 | 2/2020 | Fish et al. |
| 2020/0060516 A1 | 2/2020 | Baez |
| 2020/0085516 A1 | 3/2020 | DeFonzo |
| 2020/0086087 A1 | 3/2020 | Hart et al. |
| 2020/0091799 A1 | 3/2020 | Covington et al. |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho et al. |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0129252 A1 | 4/2020 | Kokish et al. |
| 2020/0138531 A1 | 5/2020 | Chaplin |
| 2020/0146769 A1 | 5/2020 | Eyre |
| 2020/0155245 A1 | 5/2020 | Yu |
| 2020/0163726 A1 | 5/2020 | Tanner |
| 2020/0170720 A1 | 6/2020 | Ummalaneni |
| 2020/0171660 A1 | 6/2020 | Ho |
| 2020/0188043 A1 | 6/2020 | Yu |
| 2020/0197109 A1 | 6/2020 | Chaplin |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0230360 A1 | 7/2020 | Yu et al. |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |
| 2020/0281787 A1 | 9/2020 | Ruiz |
| 2020/0297437 A1 | 9/2020 | Schuh |
| 2020/0297444 A1 | 9/2020 | Camarillo et al. |
| 2020/0305922 A1 | 10/2020 | Schuh |
| 2020/0305983 A1 | 10/2020 | Yampolsky |
| 2020/0305989 A1 | 10/2020 | Schuh |
| 2020/0305992 A1 | 10/2020 | Schuh et al. |
| 2020/0315717 A1 | 10/2020 | Bovay |
| 2020/0315723 A1 | 10/2020 | Hassan |
| 2020/0323596 A1 | 10/2020 | Moll |
| 2020/0330167 A1 | 10/2020 | Romo |
| 2020/0345216 A1 | 11/2020 | Jenkins |
| 2020/0352420 A1 | 11/2020 | Graetzel et al. |
| 2020/0360183 A1 | 11/2020 | Alvarez et al. |
| 2020/0367726 A1 | 11/2020 | Landey et al. |
| 2020/0367981 A1 | 11/2020 | Ho et al. |
| 2020/0375678 A1 | 12/2020 | Wallace et al. |
| 2020/0383735 A1 | 12/2020 | Lewis et al. |
| 2020/0405411 A1 | 12/2020 | Draper et al. |
| 2020/0405413 A1 | 12/2020 | Kokish et al. |
| 2020/0405419 A1 | 12/2020 | Mao et al. |
| 2020/0405420 A1 | 12/2020 | Purohit et al. |
| 2020/0405423 A1 | 12/2020 | Schuh |
| 2020/0405424 A1 | 12/2020 | Schuh |
| 2020/0405434 A1 | 12/2020 | Schuh et al. |
| 2020/0406002 A1 | 12/2020 | Romo et al. |
| 2021/0007819 A1 | 1/2021 | Schuh et al. |
| 2021/0008341 A1 | 1/2021 | Landey et al. |
| 2021/0045819 A1 | 2/2021 | Castillo et al. |
| 2021/0045822 A1 | 2/2021 | Landey et al. |
| 2021/0045823 A1 | 2/2021 | Landey et al. |
| 2021/0045824 A1 | 2/2021 | Landey et al. |
| 2021/0059766 A1 | 3/2021 | Graetzel et al. |
| 2021/0121052 A1 | 4/2021 | Graetzel et al. |
| 2021/0169588 A1 | 6/2021 | Graetzel et al. |
| 2021/0178032 A1 | 6/2021 | Hsu et al. |
| 2021/0196293 A1 | 7/2021 | Lin et al. |
| 2021/0196312 A1 | 7/2021 | Plewe et al. |
| 2021/0196399 A1 | 7/2021 | Ayvali et al. |
| 2021/0196410 A1 | 7/2021 | Hsu et al. |

FOREIGN PATENT DOCUMENTS

| | | |
|---|---|---|
| AU | 2018290831 A1 | 12/2019 |
| AU | 2018292606 A1 | 1/2020 |
| AU | 2018347472 A1 | 4/2020 |
| AU | 2018378808 A1 | 5/2020 |
| AU | 2019347767 A1 | 4/2021 |
| AU | 2021204979 A1 | 8/2021 |
| CN | 101161426 A | 4/2008 |
| CN | 101443069 | 5/2009 |
| CN | 100515347 | 7/2009 |
| CN | 101495023 A | 7/2009 |
| CN | 102015759 A | 4/2011 |
| CN | 201884596 U | 6/2011 |
| CN | 102316817 | 1/2012 |
| CN | 102327118 A | 1/2012 |
| CN | 102458295 A | 5/2012 |
| CN | 102665590 A | 9/2012 |
| CN | 102834043 A | 12/2012 |
| CN | 102973317 A | 3/2013 |
| CN | 103037799 A | 4/2013 |
| CN | 103298414 | 9/2013 |
| CN | 103735313 A | 4/2014 |
| CN | 104619281 | 5/2015 |
| CN | 102947730 B | 7/2015 |
| CN | 105005103 A | 10/2015 |
| CN | 105147393 A | 12/2015 |
| CN | 105559850 A | 5/2016 |
| CN | 105559886 A | 5/2016 |
| CN | 205729413 | 11/2016 |
| CN | 108882837 A | 11/2018 |
| CN | 108990412 A | 12/2018 |
| CN | 110831653 A | 2/2020 |
| CN | 110868903 A | 3/2020 |
| CN | 110891514 A | 3/2020 |
| CN | 111386450 A | 7/2020 |
| CN | 111432856 A | 7/2020 |
| CN | 112472007 A | 3/2021 |
| CN | 108369450 B | 4/2021 |
| CN | 112770690 A | 5/2021 |
| CN | 112804946 A | 5/2021 |
| DE | 19649082 C1 | 1/1998 |
| DE | 102004020465 | 9/2005 |
| DE | 102015016152 A1 | 6/2017 |
| EP | 1 321 106 | 6/2003 |
| EP | 1442720 A1 | 8/2004 |
| EP | 1321106 B1 | 10/2005 |
| EP | 1 849 423 | 10/2007 |
| EP | 1849423 A2 | 10/2007 |
| EP | 2043501 A2 | 4/2009 |
| EP | 2046227 A2 | 4/2009 |
| EP | 2210066 A2 | 7/2010 |
| EP | 2239600 A1 | 10/2010 |
| EP | 2567670 A1 | 3/2013 |
| EP | 3025630 A1 | 6/2016 |
| EP | 3387514 B1 | 6/2019 |

(56) References Cited

FOREIGN PATENT DOCUMENTS

| | | |
|---|---|---|
| EP | 3518724 A1 | 8/2019 |
| EP | 2577363 B1 | 7/2020 |
| EP | 3676587 A1 | 7/2020 |
| EP | 3752085 A1 | 12/2020 |
| EP | 3600031 A4 | 1/2021 |
| EP | 3644820 A4 | 3/2021 |
| EP | 3645100 A4 | 3/2021 |
| EP | 3820373 A1 | 5/2021 |
| EP | 3856064 A1 | 8/2021 |
| EP | 3684438 A4 | 9/2021 |
| JP | 3736173 A | 5/1995 |
| JP | 2005-270464 | 10/2005 |
| JP | 2009139187 A | 6/2009 |
| JP | 2010046384 A | 3/2010 |
| JP | 2014159071 A | 9/2014 |
| JP | 2015181495 A | 10/2015 |
| JP | 2020512102 A | 4/2020 |
| JP | 2020526252 A | 8/2020 |
| JP | 2020526254 A | 8/2020 |
| JP | 2019531807 | 11/2020 |
| JP | 2020536754 A | 12/2020 |
| JP | 2021505287 A | 2/2021 |
| JP | 2021513436 A | 5/2021 |
| KR | 20190119541 A | 10/2019 |
| KR | 20190134968 A | 12/2019 |
| KR | 20200023640 A | 3/2020 |
| KR | 20200024873 A | 3/2020 |
| KR | 20200071744 A | 6/2020 |
| KR | 20200099127 A | 8/2020 |
| KR | 20200122337 A | 10/2020 |
| KR | 20210042134 A | 4/2021 |
| KR | 20210073542 A | 6/2021 |
| KR | 102297011 B1 | 9/2021 |
| WO | 9414494 A2 | 7/1994 |
| WO | 9622591 A1 | 7/1996 |
| WO | 32074178 A2 | 9/2002 |
| WO | 2007005976 A1 | 1/2007 |
| WO | 2007088208 A1 | 8/2007 |
| WO | 2007146987 A2 | 12/2007 |
| WO | 2008014425 A2 | 1/2008 |
| WO | 2008031077 A2 | 3/2008 |
| WO | 2008017080 A3 | 10/2008 |
| WO | 2008157399 A1 | 12/2008 |
| WO | 2008101228 A3 | 1/2009 |
| WO | 2009023801 A1 | 2/2009 |
| WO | 2009064629 A2 | 5/2009 |
| WO | 2009092059 A2 | 7/2009 |
| WO | 2010133982 A2 | 11/2010 |
| WO | 2010133982 A3 | 1/2011 |
| WO | 2011005335 A1 | 1/2011 |
| WO | 2011008922 A2 | 1/2011 |
| WO | 2011150526 A1 | 12/2011 |
| WO | WO 11/161218 | 12/2011 |
| WO | 2012037506 A2 | 3/2012 |
| WO | 2012167043 A2 | 12/2012 |
| WO | WO 13/107468 | 7/2013 |
| WO | WO 13/130895 | 9/2013 |
| WO | 2013179600 A1 | 12/2013 |
| WO | 2015127231 A1 | 8/2015 |
| WO | 2015153174 A1 | 10/2015 |
| WO | 2016137612 A1 | 9/2016 |
| WO | 2017059412 A1 | 4/2017 |
| WO | 2017075574 A1 | 5/2017 |
| WO | 2017097399 A1 | 6/2017 |
| WO | WO 17/114855 | 7/2017 |
| WO | 2017151993 A1 | 9/2017 |
| WO | 20171156070 | 9/2017 |
| WO | 2018064394 A1 | 4/2018 |
| WO | WO 18/069679 | 4/2018 |
| WO | 2018094191 A1 | 5/2018 |
| WO | 2018183727 A1 | 10/2018 |
| WO | WO 18/189722 | 10/2018 |
| WO | 2019005872 A1 | 1/2019 |
| WO | 2019005992 A1 | 1/2019 |
| WO | 2019074669 A1 | 4/2019 |
| WO | 2019113389 A1 | 6/2019 |
| WO | 2019160865 A1 | 8/2019 |
| WO | 2020033318 A1 | 2/2020 |
| WO | 2020069430 A1 | 4/2020 |
| WO | 2021028889 A1 | 2/2021 |
| WO | 2021044297 A1 | 3/2021 |
| WO | 2021137071 A1 | 7/2021 |
| WO | 2021137106 A1 | 7/2021 |
| WO | 2021137108 A1 | 7/2021 |
| WO | 2021137109 A1 | 7/2021 |

OTHER PUBLICATIONS

Invitation to Pay Additional Fees in PCT application No. PCT/US16/059686, dated Dec. 8, 2016.

International Search Report in PCT application No. PCT/US16/059686, dated Feb. 17, 2017.

Extended European Search Report dated Jun. 12, 2019 in patent application No. 16861031.9.

Hernansanz et al., 2015, A multi-robot cooperation strategy for dexterous task oriented teleoperation, 2015, ELSEVIER Robotics and Autonomous Systems, 68(205):156-172.

International Preliminary Report on Patentability for PCT/US2016/059686 dated Feb. 17, 2017, 7 pages.

International search report for appl No. PCTIB2020057704, dated Dec. 18, 2020, 16 pages.

International Search Report for PCT/IB2020/057704 dated Feb. 18, 2021, 16 pages.

International search report for PCT/IB2020/061905, dated Mar. 18, 2021, 8 pages.

International Search Report for PCT/US2016/059686 dated Feb. 17, 2017,4 pages.

Invitation to Pay Additional Fees in PCT appl No. PCT/US2016/059686, dated Dec. 8, 2016, 2 pages.

Mayo Clinic, Robotic Surgery, https://www.mayoclinic.org/tests-procedures/robotic-surgery/about/pac- 20394974?p=1, downloaded from the internet on Jul. 12, 2018, 2 pgs.

Mayo Clinic, Robotic Surgery, https://www.mayoclinic.org/tests-procedures/robotic-surgery/about/pac- 20394974?p=1, downloaded from the internet on Jul. 12, 2018, 2 pp.

Notice of Acceptance for appl No. 2016343849, dated Aug. 5, 2021, 3 pages.

Notice of allowance for U.S. Appl. No. 15/948,369, dated Aug. 17, 2021, 10 pages.

Notice of Allowance for U.S. Appl. No. 15/948,369, dated Dec. 14, 2021, 11 pages.

Notice of allowance for U.S. Appl. No. 16/355,437, dated Oct. 28, 2021, 10 pages.

Notice of allowance for appl No. 1711167, dated Jul. 20, 2021, 7 pages.

Notice of allowance for U.S. Appl. No. 17/121,167, dated Apr. 6, 2021, 7 pages.

Notice of Allowance for U.S. Appl. No. 17/121,167, dated Nov. 10, 2021,4 pages.

Notice of allowance for U.S. Appl. No. 17/121,167, dated Nov. 3, 2021, 7 pages.

Office action for U.S. Appl. No. 15/948,369, dated May 25, 2021,14 pages.

Office action for U.S. Appl. No. 15/948,369, dated Nov. 20, 2020, 14 pages.

Office action for U.S. Appl. No. 16/865,904, dated Sep. 17, 2021, 13 pages.

PCT Invitation to Pay Additional Fees, PCT Application No. PCT/US2016/059686, Dec. 8, 2016, 2 pages.

Ramezanifard et al., 2007, A Novel Modeling Approach for Collision Avoidance in Robotic Surgery, 2007 Science Publications, American Journal of Applied Sciences 4(9):693-699, 7 pages.

U.S. Appl. No. 62/248,737, filed Oct. 30, 2015, Inventors: David P. Noonan et al., 76 pages.

Written opinion for PCT/IB2020/061905, dated Mar. 18, 2021, 6 pages.

Written Opinion of the International Search Authority for PCT/IB2020/057704 dated Feb. 18, 2021, 9 pages.

(56) References Cited

OTHER PUBLICATIONS

Written Opinion of the International Searching Authority for PCT/US2016/059686 dated Feb. 17, 2017, 6 pages.
JP Office Action dated Dec. 1, 2020, for Patent Appl. No. 2018-521951,4 pages.
AU Examination report for appl. no. 2016343849, dated Mar. 16, 2021, 5 pages.

* cited by examiner 1060A
1060B
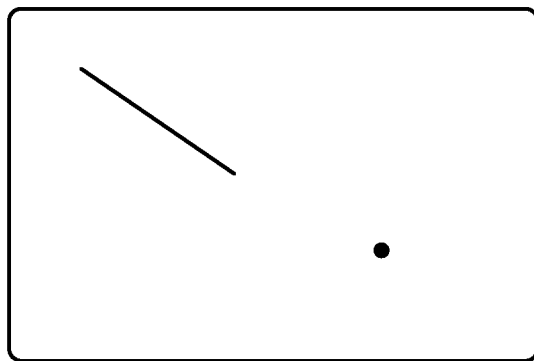
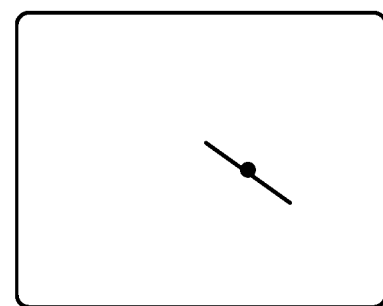
FIG. 10C
FIG. 10D
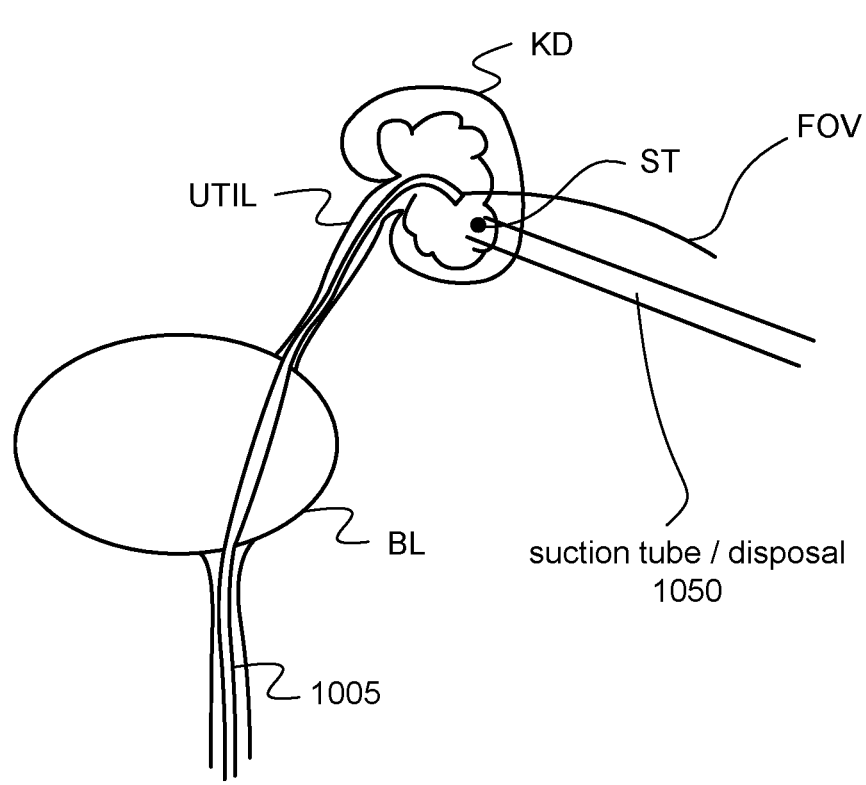
FIG. 10E

OBJECT CAPTURE WITH A BASKET

CROSS-REFERENCE TO RELATED APPLICATIONS

This application is a continuation of U.S. patent application Ser. No. 15/339,476, filed Oct. 31, 2016, and scheduled to issue as U.S. Pat. No. 9,949,749 on Apr. 24, 2018, which claims the benefit of and priority to U.S. Provisional Application No. 62/248,737, filed Oct. 30, 2015, each of which is incorporated herein by reference.

BACKGROUND

1. Field of Art

This description generally relates to surgical robotics, and particularly to lithotomy devices and procedures using a surgical robotics system.

2. Description of the Related Art

Every year, doctors perform thousands of procedures to remove urinary stones from patients' urinary tracts. Urinary stones may include kidney stones found in the kidneys and ureters as well as bladder stones found in the bladder. Such urinary stones form as a result of concentrated minerals and cause significant abdominal pain once they reach a size sufficient to impede urine flow through the ureter or urethra. Such stones may formed from calcium, magnesium, ammonia, ur acid, cysteine, or other compounds.

To remove urinary stones from the bladder and ureter, surgeons use a ureteroscope inserted into the urinary tract through the urethra. Typically, a ureteroscope includes an endoscope at its distal end to enable visualization of the urinary tract. The ureteroscope also includes a lithotomy mechanism to capture or break apart urinary stones. During the ureteroscopy procedure, one physician controls the position of the ureteroscope and the other surgeon controls the lithotomy mechanism. The controls of the ureteroscope are located on a proximal handle of the ureteroscope and accordingly are difficult to grasp as the orientation of the ureteroscope changes. Accordingly, present ureteroscopy techniques are labor intensive and reliant on ureteroscopes with non-ergonomic designs.

To remove large kidney stones from the kidneys, surgeons use a percutaneous nephrolithotomy technique that includes inserting a nephroscope through the skin to break up and remove the kidney stone. However, present techniques for percutaneous nephrolithotomy ("PCNL") include using fluoroscopy to locate the kidney stone and to ensure accurate insertion of the nephroscope. Fluoroscopy increases the cost of the nephrolithotomy procedure due to the cost of the fluoroscope itself as well as the cost of a technician to operate the fluoroscope. Fluoroscopy also exposes the patient to radiation for a prolonged period of time. Even with fluoroscopy, accurately making a percutaneous incision to access the kidney stone is difficult and imprecise. Additionally, present nephrolithotomy techniques typically involve a two-day or three-day inpatient stay. In sum, present nephrolithotomy techniques are costly and problematic for patients.

SUMMARY

This description includes methods and devices for more easily carrying out a ureteroscopy. This description also includes methods and devices for more easily carrying out a PCNL. For ureteroscopy, a basketing device includes a number of independently manipulable pull wires that allow full 360 degree motion of the basket, which makes capture of a stone easier. A central working channel in the basketing apparatus allows a variety of other tools to be placed near a basket to break up a captured stone. Further, a technique for ureteroscopy is described that helps prevent stones from escaping from a basket while the basket is being closed.

For PCNL, a variety of techniques and devices are described that make use of an alignment sensor in place of fluoroscopy to detect the position of a stone in a kidney. The alignment sensor may, for example, be an EM sensor which works in conjunction with EM field generators placed around the patient and an associated CT (or other) scan to provide position and orientation information for EM sensor in the patient's body. The alignment sensor is placed via a cavity, such as the ureter using a ureteroscope, and together with a camera is used to identify the location of the stone. The alignment sensor provides a guidance mechanism for directing the percutaneous cut for accessing the stone within the kidney. Further, as at this point in the PCNL procedure, a scope is already present, a working channel of the scope can be used to advance other tools to assist in the removal of the stone through a port created by the PCNL. Techniques for performing the PCNL are described, as well as for how to go about removing the stone via the PCNL port.

Although this description is largely described with respect to the example use cases of ureteroscopy, PCNL, and the removal of urinary stones and stone fragments, these descriptions are equally applicable to other surgical operations concerned with the removal of objects from the patient, including any object that can be safely removed via a patient cavity (e.g., the esophagus, ureter, intestine, etc.) or via percutaneous access, such as gallbladder stone removal or lung (pulmonary/transthoracic) tumor biopsy.

BRIEF DESCRIPTION OF DRAWINGS

FIGS. 10A-10E illustrate an example of a PCNL process that includes a ureteroscope including an electromagnetic sensor to identify the location of a stone, according to one embodiment.

Reference will now be made in detail to several embodiments, examples of which are illustrated in the accompanying figures. It is noted that wherever practicable similar or like reference numbers may be used in the figures and may indicate similar or like functionality. The figures depict embodiments of the described system (or method) for purposes of illustration only. One skilled in the art will readily recognize from the following description that alternative embodiments of the structures and methods illustrated herein may be employed without departing from the principles described herein.

DETAILED DESCRIPTION

I. Overview

I.A. Surgical Robotics System

Figure 1A:
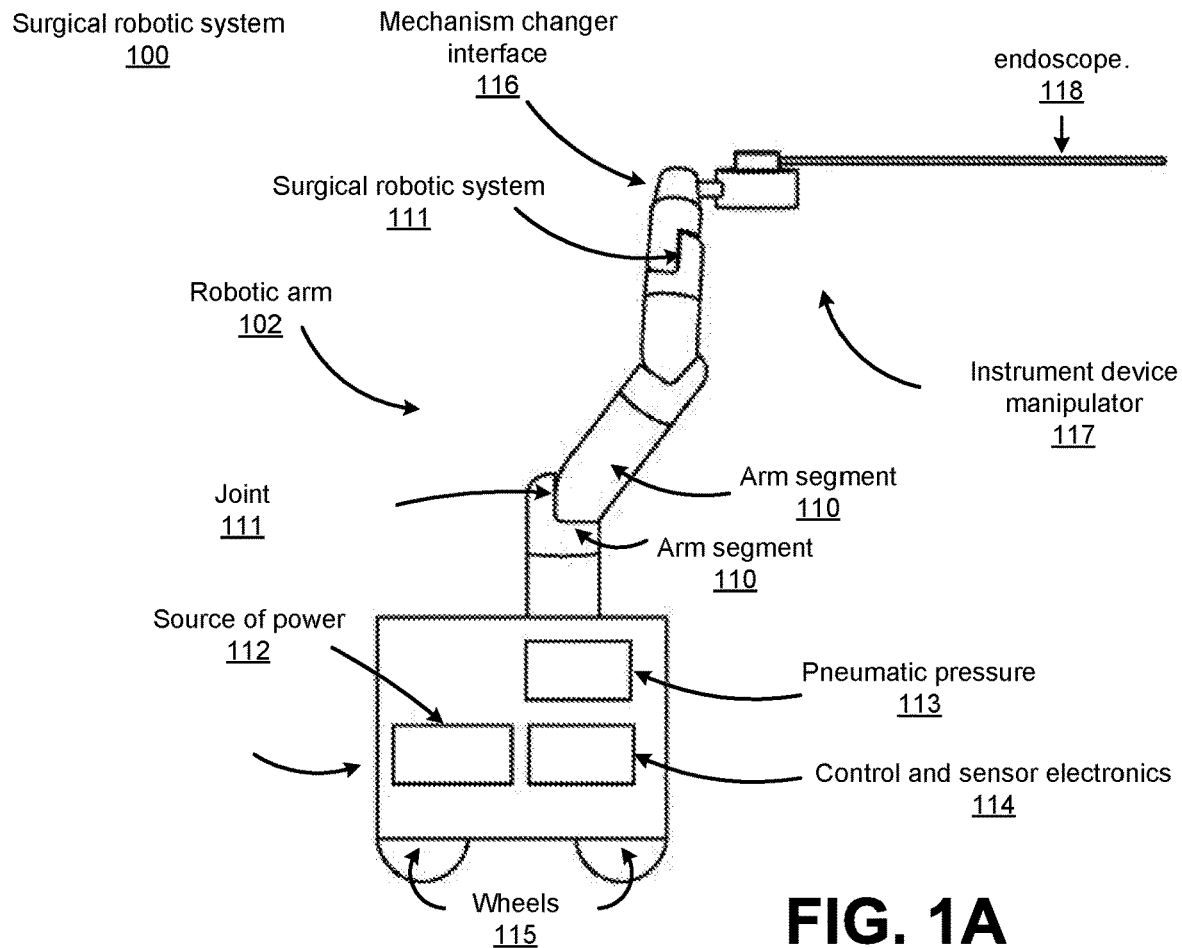
FIG. 1A shows an example surgical robotic system, according to one embodiment.

FIG. 1A shows an example surgical robotic system 100, according to one embodiment. The surgical robotic system 100 includes a base 101 coupled to one or more robotic arms, e.g., robotic arm 102. The base 101 is communicatively coupled to a command console, which is further described with reference to FIG. 2. The base 101 can be positioned such that the robotic arm 102 has access to perform a surgical procedure on a patient, while a user such as a physician may control the surgical robotic system 100 from the comfort of the command console. In some embodiments, the base 101 may be coupled to a surgical operating table or bed for supporting the patient. Though not shown in FIG. 1 for purposes of clarity, the base 101 may include subsystems such as control electronics, pneumatics, power sources, optical sources, and the like. The robotic arm 102 includes multiple arm segments 110 coupled at joints 111, which provides the robotic arm 102 multiple degrees of freedom, e.g., seven degrees of freedom corresponding to seven arm segments. The base 101 may contain a source of power 112, pneumatic pressure 113, and control and sensor electronics 114—including components such as a central processing unit, data bus, control circuitry, and memory—and related actuators such as motors to move the robotic arm 102. The electronics 114 in the base 101 may also process and transmit control signals communicated from the command console.

In some embodiments, the base 101 includes wheels 115 to transport the surgical robotic system 100. Mobility of the surgical robotic system 100 helps accommodate space constraints in a surgical operating room as well as facilitate appropriate positioning and movement of surgical equipment. Further, the mobility allows the robotic arms 102 to be configured such that the robotic arms 102 do not interfere with the patient, physician, anesthesiologist, or any other equipment. During procedures, a user may control the robotic arms 102 using control devices such as the command console.

In some embodiments, the robotic arm 102 includes set up joints that use a combination of brakes and counter-balances to maintain a position of the robotic arm 102. The counter-balances may include gas springs or coil springs. The brakes, e.g., fail safe brakes, may be include mechanical and/or electrical components. Further, the robotic arms 102 may be gravity-assisted passive support type robotic arms.

Each robotic arm 102 may be coupled to an instrument device manipulator (IDM) 117 using a mechanism changer interface (MCI) 116. The IDM 117 can be removed and replaced with a different type of IDM, for example, a first type of IDM manipulates an endoscope, while a second type of IDM manipulates a laparoscope. The MCI 116 includes connectors to transfer pneumatic pressure, electrical power, electrical signals, and optical signals from the robotic arm 102 to the IDM 117. The MCI 116 can be a set screw or base plate connector. The IDM 117 manipulates surgical instruments (also referred to as surgical tools) such as the endoscope 118 using techniques including direct drive, harmonic drive, geared drives, belts and pulleys, magnetic drives, and the like. The MCI 116 is interchangeable based on the type of IDM 117 and can be customized for a certain type of surgical procedure. The robotic 102 arm can include a joint level torque sensing and a wrist at a distal end, such as the KUKA AG® LBR5 robotic arm.

An endoscope 118 is a tubular and flexible surgical instrument that is inserted into the anatomy of a patient to capture images of the anatomy (e.g., body tissue). In particular, the endoscope 118 includes one or more imaging devices (e.g., cameras or other types of optical sensors) that capture the images. The imaging devices may include one or more optical components such as an optical fiber, fiber array, or lens. The optical components move along with the tip of the endoscope 118 such that movement of the tip of the endoscope 118 results in changes to the images captured by the imaging devices. An example endoscope 118 is further described with reference to FIGS. 3A-4B in Section IV. Endoscope.

Robotic arms 102 of the surgical robotic system 100 manipulate the endoscope 118 using elongate movement members. The elongate movement members may include pull wires, also referred to as pull or push wires, cables, fibers, or flexible shafts. For example, the robotic arms 102 actuate multiple pull wires coupled to the endoscope 118 to deflect the tip of the endoscope 118. The pull wires may include both metallic and non-metallic materials such as stainless steel, Kevlar, tungsten, carbon fiber, and the like. The endoscope 118 may exhibit nonlinear behavior in response to forces applied by the elongate movement members. The nonlinear behavior may be based on stiffness and compressibility of the endoscope 118, as well as variability in slack or stiffness between different elongate movement members.

Figure 1B:
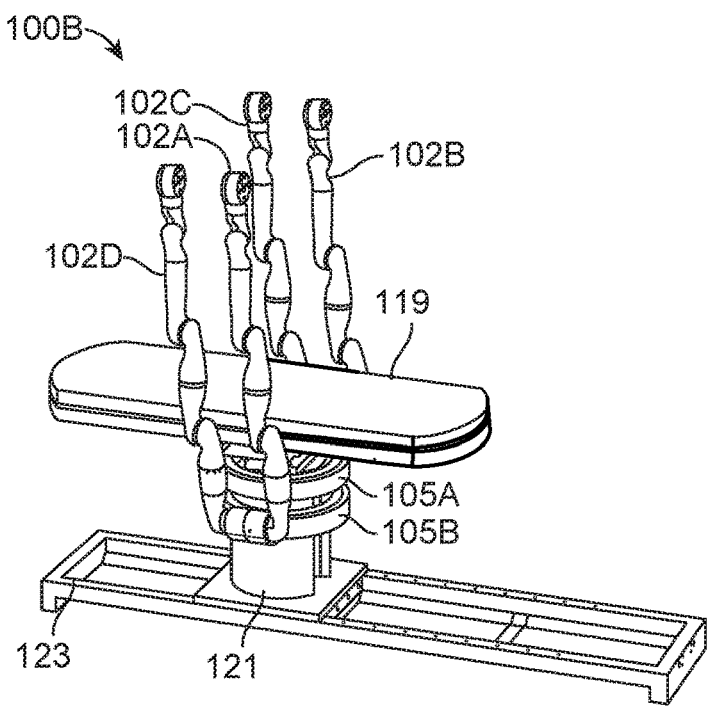
FIG. 1B is a perspective view of a surgical robotics system with column-mounted robotic arms according to one embodiment.

FIG. 1B is a perspective view of a surgical robotics system 100A with column-mounted robotic arms according to one embodiment. The surgical robotics system 100A includes a set of robotic arms 102, a set of column rings, table 119, column 121, and base 123.

The table 119 provides support for a patient undergoing surgery using the surgical robotics system 100. Generally, the table 119 is parallel to the ground, though the table 119 may change its orientation and configuration to facilitate a variety of surgical procedures. The table may be rotated around the patient's transverse axis or tilted along the patient's longitudinal axis using one or more pivots between the table 119 and the column 121. The table 119 may include swivel segments, foldable segments, or both to change the configuration of an upper surface of the table 119 that supports the patient. The table 119 may include a trapdoor to facilitate drainage of bodily fluids or other ensuing fluids during surgical procedures.

The column 121 is coupled to the table 119 on one end and coupled to the base 123 on the other end. Generally, the column 121 is cylindrically shaped to accommodate one or more column rings 105 coupled to the column 121; however, the column 121 may have other shapes such as oval or rectangular. A column ring 105 is movably coupled to the column. For example, a column ring 105 translates vertically along the axis of the column 121, rotates horizontally around the axis of the column 121, or both. Column rings 105 are described in more detail with respect to FIG. 2 below. The column may be rotated around the column's central axis relative to the base 123 using a rotation mechanism.

The base 123 is parallel to the ground and provides support for the column 121 and the table 119. The base 123 may include wheels, treads, or other means of positioning or transporting the surgical robotics system 100. The base 123 may accommodate the set of robotic arms 102, the one or more column rings 105, or both as part of an inactive configuration for storage, such as inside a removable housing (not shown). The base 123 may include rails (not shown) along which robotic arms 102 may be movably coupled as an alternative or supplement to column rings 105.

Generally, the set of robotics arms includes one or more robotic arms 102 coupled to one or more column rings 105, such as column ring 105A. A robotic arm 102 attached to a column 105 may be referred to as a column-mounted robotic arm 102. The surgical robotics system 100A uses robotic arms 102 to perform surgical procedures on a patient lying on the table 119.

Further details and configurations regarding table 119, column 121, base 123, column ring 105, and robotic arm 102 are included in U.S. patent application Ser. No. 15/154,765, filed May 13, 2016, as well as in U.S. patent application Ser. No. 15/154,762, filed May 13, 2016, each of which is incorporated by reference herein. For example, an alternative surgical robotics system includes a first robotic arm 102 mounted to a column ring 105 and a second robotic arm mounted to a rail included in the base 123.

Figure 2:
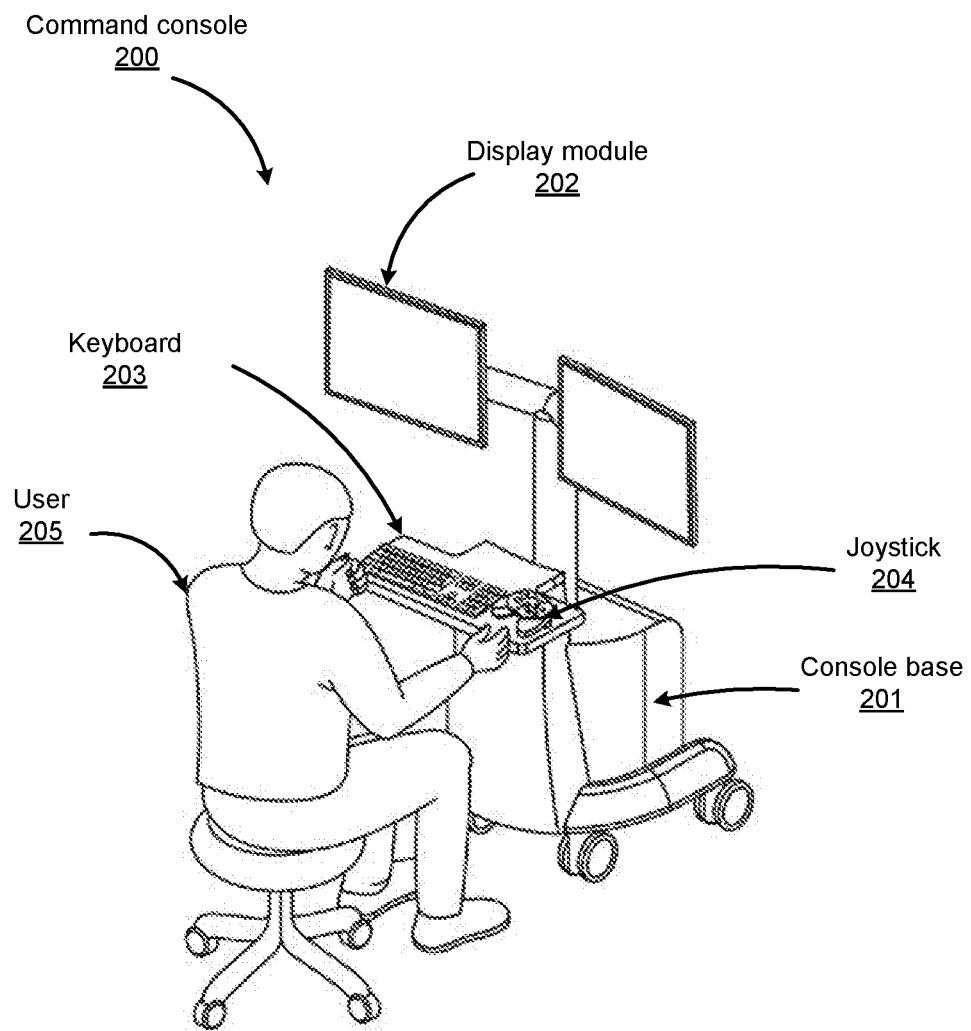
FIG. 2 shows an example command console for the example surgical robotic system 100, according to one embodiment.

FIG. 2 shows an example command console 200 for the example surgical robotic system 100, according to one embodiment. The command console 200 includes a console base 201, display modules 202, e.g., monitors, and control modules, e.g., a keyboard 203 and joystick 204. In some embodiments, one or more of the command console 200 functionality may be integrated into a base 101 of the surgical robotic system 100 or another system communicatively coupled to the surgical robotic system 100. A user 205, e.g., a physician, remotely controls the surgical robotic system 100 from an ergonomic position using the command console 200.

The console base 201 may include the basic components of a computer system, that is a central processing unit (i.e., a computer processer), a memory/data storage unit, a data bus, and associated data communication ports that are responsible for interpreting and processing signals such as imagery and alignment sensor data, e.g., from the endoscope 118 shown in FIG. 1. In some embodiments, both the console base 201 and the base 101 perform signal processing for load-balancing. The console base 201 may also process commands and instructions provided by the user 205 through the control modules 203 and 204. In addition to the keyboard 203 and joystick 204 shown in FIG. 2, the control modules may include other devices, for example, computer mice, trackpads, trackballs, control pads, video game controllers, and sensors (e.g., motion sensors or cameras) that capture hand gestures and finger gestures.

The user 205 can control a surgical instrument such as the endoscope 118 using the command console 200 in a velocity mode or position control mode. In velocity mode, the user 205 directly controls pitch and yaw motion of a distal end of the endoscope 118 based on direct manual control using the control modules. For example, movement on the joystick 204 may be mapped to yaw and pitch movement in the distal end of the endoscope 118. The joystick 204 can provide haptic feedback to the user 205. For example, the joystick 204 vibrates to indicate that the endoscope 118 cannot further translate or rotate in a certain direction. The command console 200 can also provide visual feedback (e.g., pop-up messages) and/or audio feedback (e.g., beeping) to indicate that the endoscope 118 has reached maximum translation or rotation.

In position control mode, the command console 200 uses a three-dimensional (3D) map of a patient and pre-determined computer models of the patient to control a surgical instrument, e.g., the endoscope 118. The command console 200 provides control signals to robotic arms 102 of the surgical robotic system 100 to manipulate the endoscope 118 to a target location. Due to the reliance on the 3D map, position control mode requires accurate mapping of the anatomy of the patient.

In some embodiments, users 205 can manually manipulate robotic arms 102 of the surgical robotic system 100 without using the command console 200. During setup in a surgical operating room, the users 205 may move the robotic arms 102, endoscopes 118, and other surgical equipment to access a patient. The surgical robotic system 100 may rely on force feedback and inertia control from the users 205 to determine appropriate configuration of the robotic arms 102 and equipment.

The display modules 202 may include electronic monitors, virtual reality viewing devices, e.g., goggles or glasses, and/or other means of display devices. In some embodiments, the display modules 202 are integrated with the control modules, for example, as a tablet device with a touchscreen. Further, the user 205 can both view data and input commands to the surgical robotic system 100 using the integrated display modules 202 and control modules. The display modules 202 allow for display of graphical GUIs that may display information about the position and orientation of various instruments operating within the patient based on information provided by one or more alignment sensors. This information may be received by electrical wires or transmitters coupled to the sensors, which transmit the information to the console base 201, which processes the information for presentation via the display modules 202.

The display modules 202 can display 3D images using a stereoscopic device, e.g., a visor or goggle. The 3D images provide an "endo view" (i.e., endoscopic view), which is a computer 3D model illustrating the anatomy of a patient. The endo view provides a virtual environment of the patient's interior and an expected location of an endoscope 118 inside the patient. A user 205 compares the endo view model to actual images captured by a camera to help mentally orient and confirm that the endoscope 118 is in the correct—or approximately correct—location within the patient. The endo view provides information about anatomical structures, e.g., the shape of an intestine or colon of the patient, around the distal end of the endoscope 118. The display modules 202 can simultaneously display the 3D model and computerized tomography (CT) scans of the anatomy the around distal end of the endoscope 118. Further, the display modules 202 may overlay the already determined navigation paths of the endoscope 118 on the 3D model and CT scans.

In some embodiments, a model of the endoscope 118 is displayed with the 3D models to help indicate a status of a surgical procedure. For example, the CT scans identify a lesion in the anatomy where a biopsy may be necessary. During operation, the display modules 202 may show a reference image captured by the endoscope 118 corresponding to the current location of the endoscope 118. The display modules 202 may automatically display different views of the model of the endoscope 118 depending on user settings and a particular surgical procedure. For example, the display modules 202 show an overhead fluoroscopic view of the endoscope 118 during a navigation step as the endoscope 118 approaches an operative region of a patient.

I.B. Endoscope

Figure 3A:
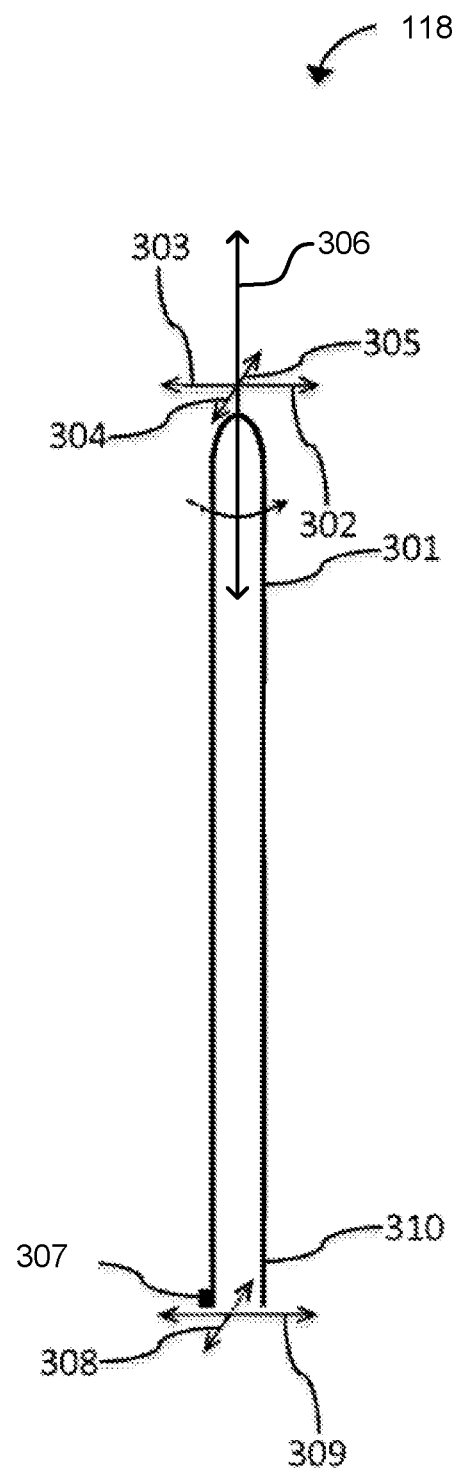
FIG. 3A illustrates multiple degrees of motion of an endoscope according to one embodiment.

FIG. 3A illustrates multiple degrees of motion of an endoscope 118 according to one embodiment. As shown in FIG. 3A, the tip 301 of the endoscope 118 is oriented with zero deflection relative to a longitudinal axis 306 (also referred to as a roll axis 306). To capture images at different orientations of the tip 301, a surgical robotic system 100 deflects the tip 301 on a positive yaw axis 302, negative yaw axis 303, positive pitch axis 304, negative pitch axis 305, or roll axis 306. The tip 301 or body 310 of the endoscope 118 may be elongated or translated in the longitudinal axis 306, x-axis 308, or y-axis 309.

The endoscope 118 includes a reference structure 307 to calibrate the position of the endoscope 118. For example, the surgical robotic system 100 measures deflection of the endoscope 118 relative to the reference structure 307. The reference structure 307 is located on a proximal end of the endoscope 118 and may include a key, slot, or flange. The reference structure 307 is coupled to a first drive mechanism for initial calibration and coupled to a second drive mechanism, e.g., the IDM 117, to perform a surgical procedure.

Figure 3B:
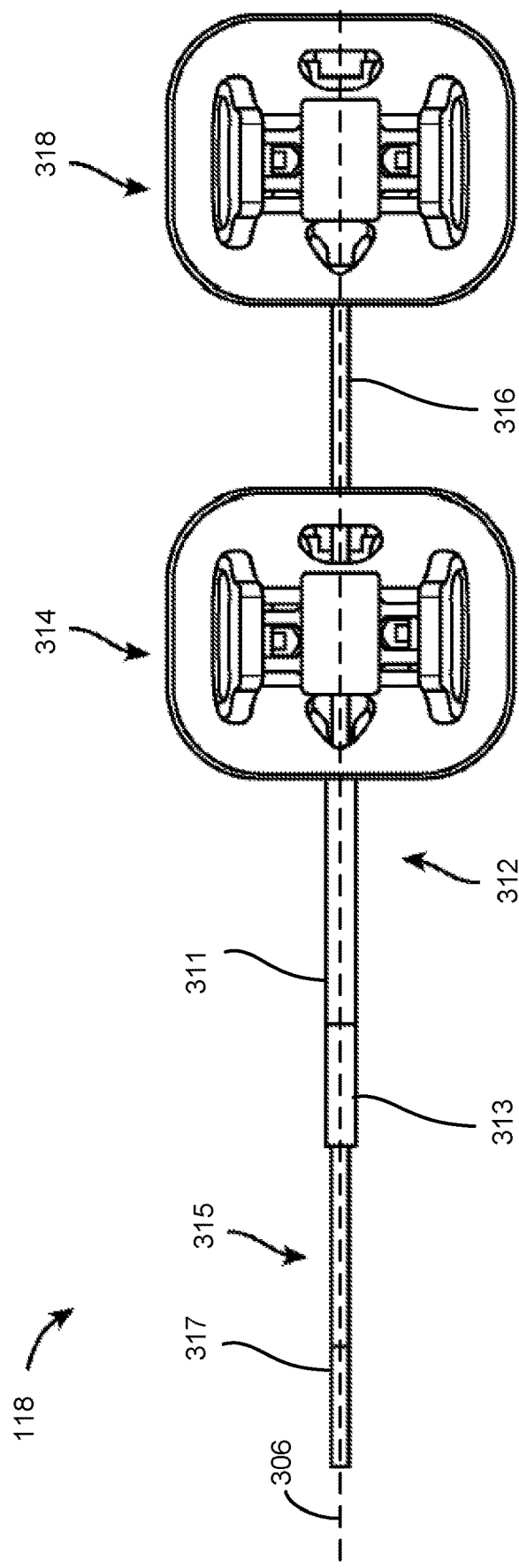
FIG. 3B is a top view of an endoscope according to one embodiment.

FIG. 3B is a top view of an endoscope 118 according to one embodiment. The endoscope 118 includes a leader 315 tubular component (or leaderscope) nested or partially nested inside and longitudinally-aligned with a sheath 311 tubular component. The sheath 311 includes a proximal sheath section 312 and distal sheath section 313. The leader 315 has a smaller outer diameter than the sheath 311 and includes a proximal leader section 316 and distal leader section 317. The sheath base 314 and the leader base 318 actuate the distal sheath section 313 and the distal leader section 317, respectively, for example, based on control signals from a user of a surgical robotic system 100. The sheath base 314 and the leader base 318 are, e.g., part of the IDM 117 shown in FIG. 1.

Both the sheath base 314 and the leader base 318 include drive mechanisms (e.g., the independent drive mechanism further described with reference to FIG. 3D in Section I.C. Instrument Device Manipulator) to control pull wires coupled to the sheath 311 and leader 315. For example, the sheath base 314 generates tensile loads on pull wires coupled to the sheath 311 to deflect the distal sheath section 313. Similarly, the leader base 318 generates tensile loads on pull wires coupled to the leader 315 to deflect the distal leader section 317. Both the sheath base 314 and leader base 318 may also include couplings for the routing of pneumatic pressure, electrical power, electrical signals, or optical signals from IDMs to the sheath 311 and leader 314, respectively. A pull wire may include a steel coil pipe along the length of the pull wire within the sheath 311 or the leader 315, which transfers axial compression back to the origin of the load, e.g., the sheath base 314 or the leader base 318, respectively.

The endoscope 118 can navigate the anatomy of a patient with ease due to the multiple degrees of freedom provided by pull wires coupled to the sheath 311 and the leader 315. For example, four or more pull wires may be used in either the sheath 311 and/or the leader 315, providing eight or more degrees of freedom. In other embodiments, up to three pull wires may be used, providing up to six degrees of freedom. The sheath 311 and leader 315 may be rotated up to 360 degrees along a longitudinal axis 306, providing more degrees of motion. The combination of rotational angles and multiple degrees of freedom provides a user of the surgical robotic system 100 with a user friendly and instinctive control of the endoscope 118.

Figure 3C:
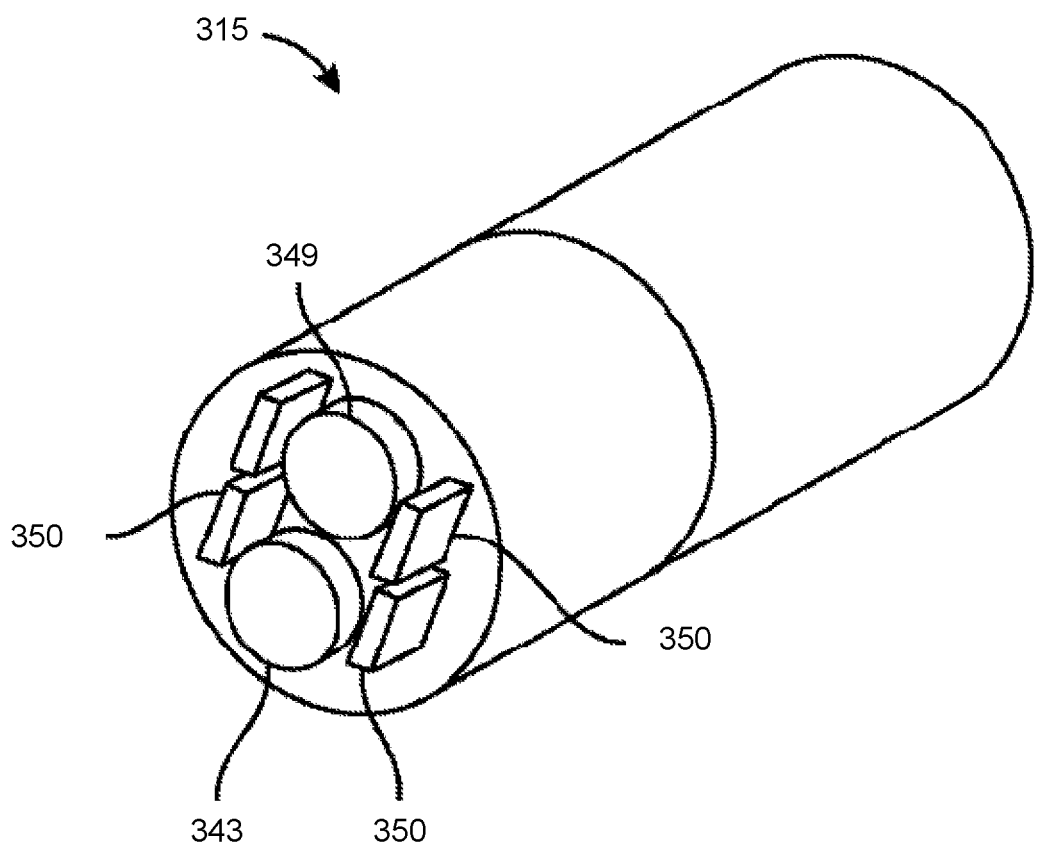
FIG. 3C is an isometric view of the distal end of the leader of an endoscope according to one embodiment.

FIG. 3C is a isometric view of the distal end of leader 315 of an endoscope 118 according to one embodiment. The leader 315 includes at least one working channel 343 and pull wires and running through conduits along the length of the walls. For example, the pull wires and may have a helix section that helps mitigate muscling and curve alignment of the leader 315. The leader 315 includes an imaging device 349 (e.g., charge-coupled device (CCD) or complementary metal-oxide semiconductor (CMOS) camera, imaging fiber bundle, etc.), light sources 350 (e.g., light-emitting diode (LED), optic fiber, etc.), and at least one working channel 343 for other components. For example, other components include camera wires, an insufflation device, a suction device, electrical wires, fiber optics, an ultrasound transducer, electromagnetic (EM) sensing components, and optical coherence tomography (OCT) sensing components. In some embodiments, the leader 315 includes a cavity that runs along the long axis of the leader 315 to form a working channel 343 which accommodates insertion of other devices such as surgical tools.

I.C. Instrument Device Manipulator

Figure 3D:
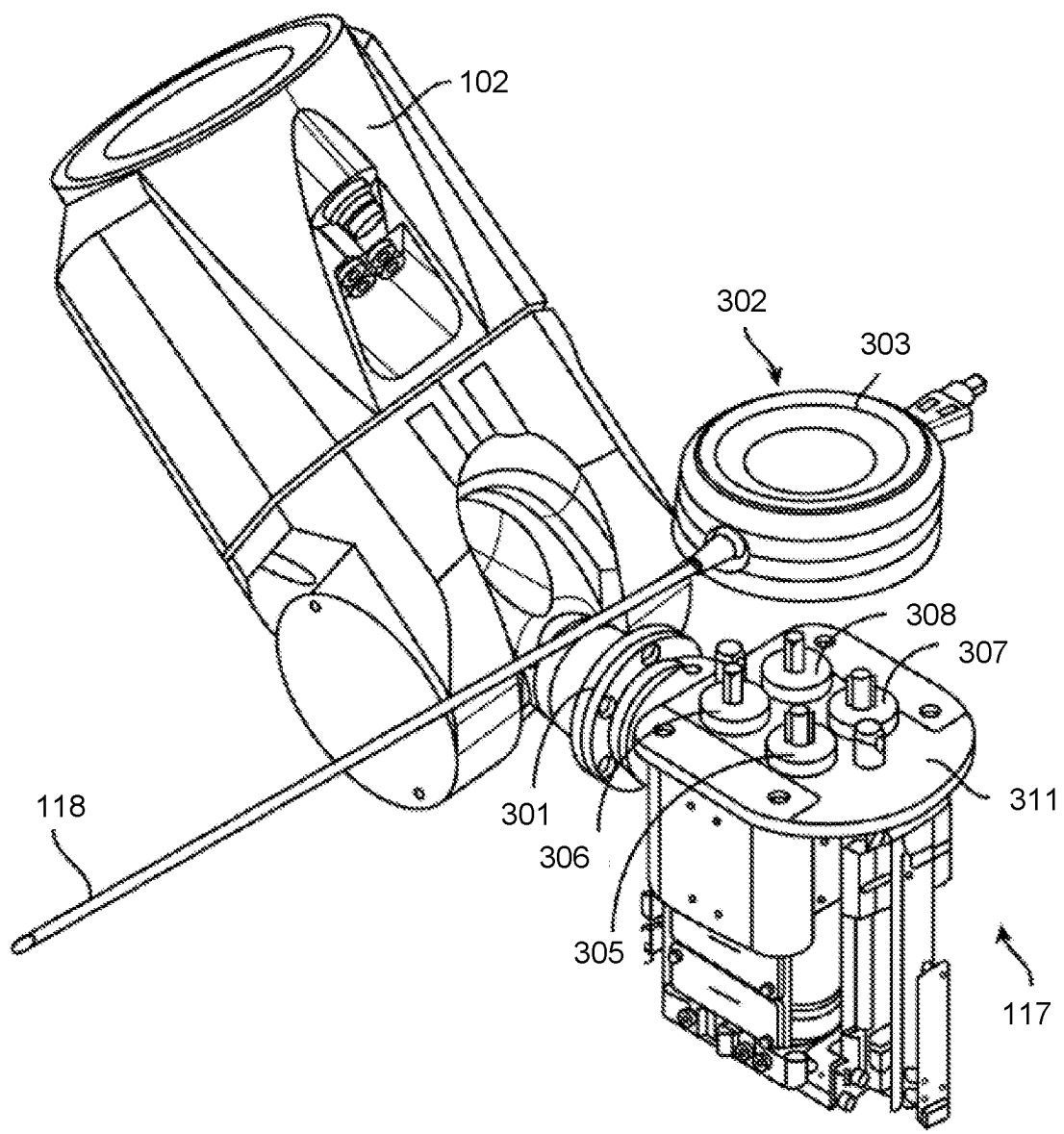
FIG. 3D is an isometric view of an instrument device manipulator of the surgical robotic system according to one embodiment.

FIG. 3D is an isometric view of an instrument device manipulator 117 of the surgical robotic system 100 according to one embodiment. The robotic arm 102 is coupled to the IDM 117 via an articulating interface 301. The IDM 117 is coupled to the endoscope 118. The articulating interface 301 may transfer pneumatic pressure, power signals, control signals, and feedback signals to and from the robotic arm 102 and the IDM 117. The IDM 117 may include a gear head, motor, rotary encoder, power circuits, and control circuits. A base 303 for receiving control signals from the IDM 117 is coupled to the proximal end of the endoscope 118. Responsive to the control signals, the IDM 117 manipulates the endoscope 118 by actuating output shafts, which are further described below with reference to FIG. 3E.

Figure 3E:
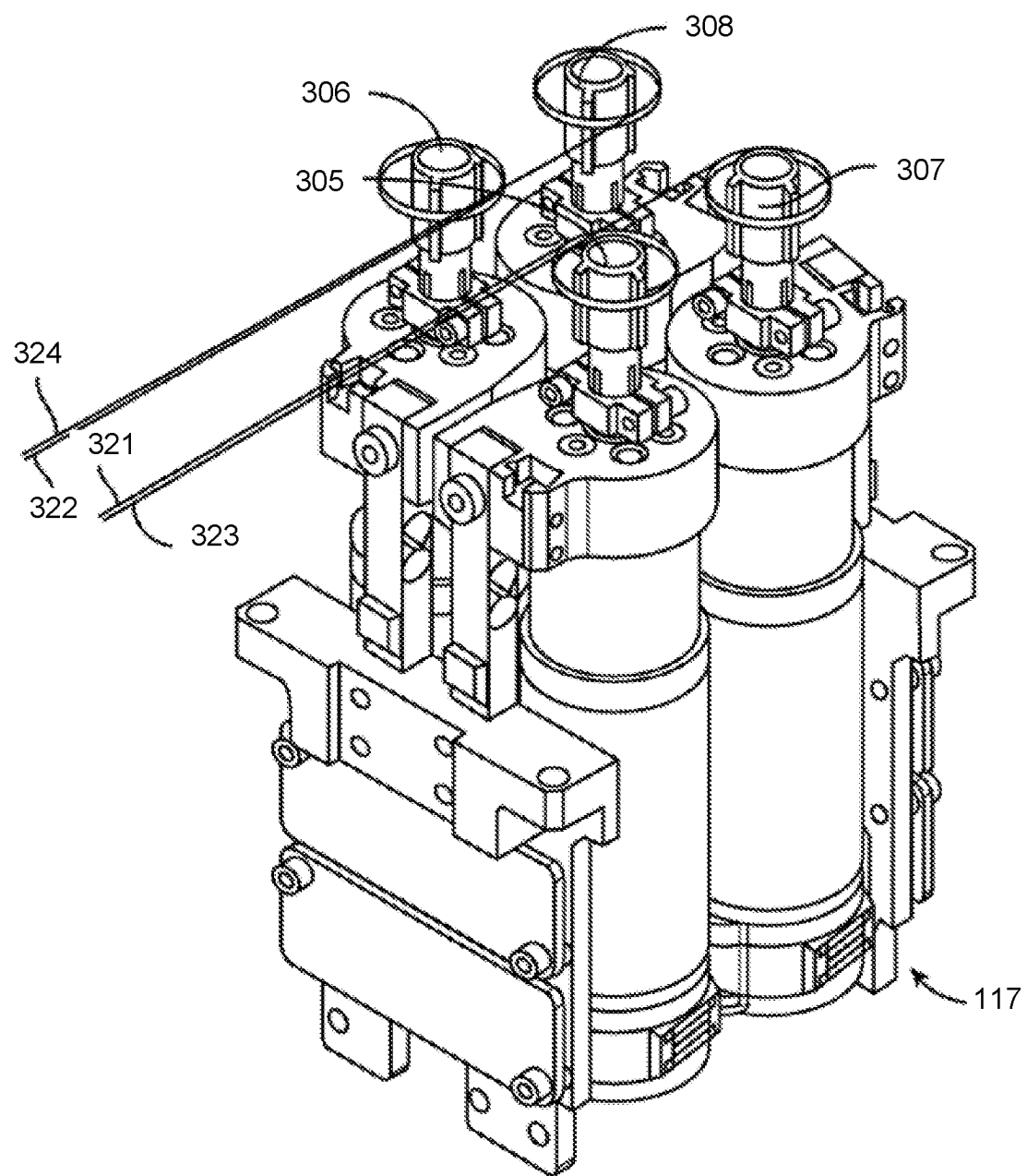
FIG. 3E is an exploded isometric view of the instrument device manipulator shown in FIG. 3D according to one embodiment.

FIG. 3E is an exploded isometric view of the instrument device manipulator shown in FIG. 3D according to one embodiment. In FIG. 3E, the endoscope 118 has been removed from the IDM 117 to reveal the output shafts 305, 306, 307, and 308 which may each control independent pull wires of an endoscope 118 or basket apparatus as described further below.

II. Lower Body Surgery

Figure 4A:
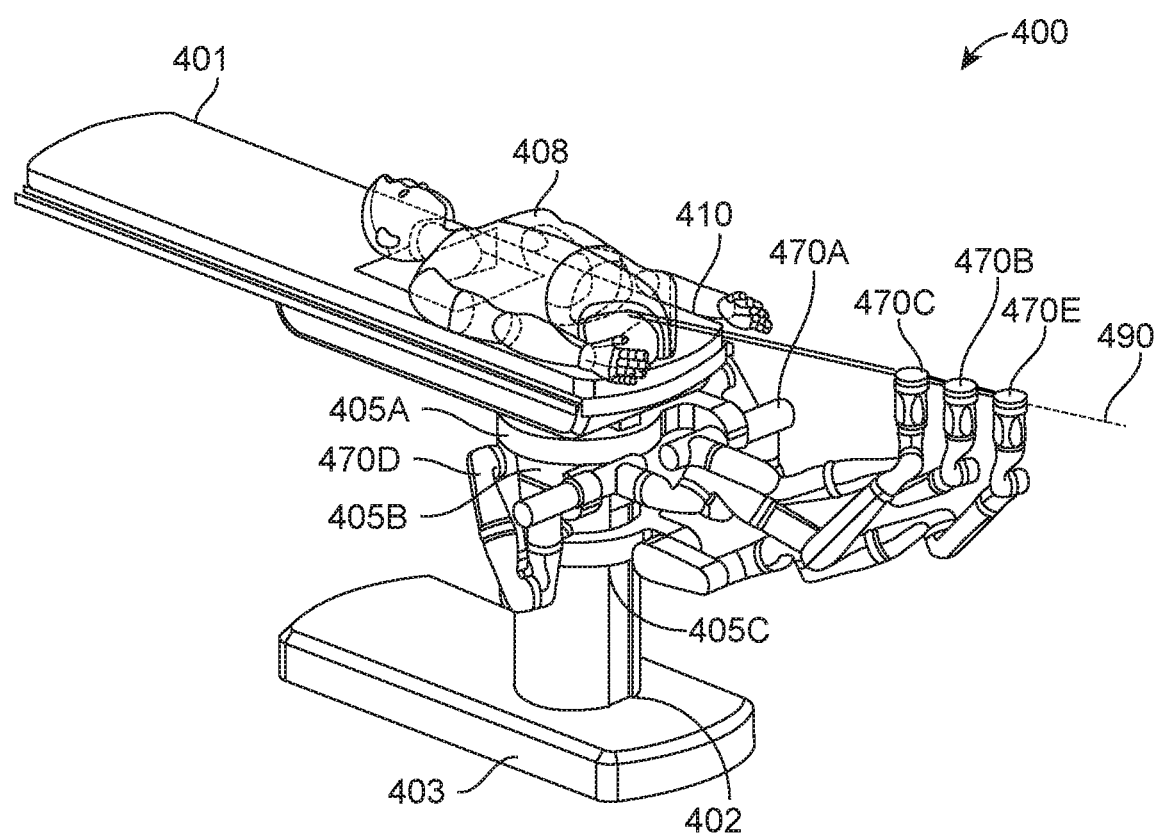
FIG. 4A is a perspective view of a surgical robotics system with column-mounted arms configured to access the lower body area of a simulated patient according to one embodiment.

FIG. 4A is a perspective view of a surgical robotics system 400A with column-mounted arms configured to access the lower body area of a simulated patient 408 according to one embodiment. The surgical robotics system 400A includes a set of robotic arms (including five robotic arms in total) and a set of three column rings. A first robotic arm 470A and a second robotic arm 470B are coupled to a first column ring 405A. A third robotic arm 470C and a fourth robotic arm 470D are coupled to a second column ring 405B. A fifth robotic arm 470E is coupled to a third column ring 405C. FIG. 4A shows a wireframe of the patient 408 lying on the table 401 undergoing a surgical procedure, e.g., ureteroscopy, involving access to the lower body area of the patient 408. Legs of the patient 408 are not shown in order to avoid obscuring portions of the surgical robotics system 400A.

The surgical robotics system 400A configures the set of robotic arms to perform a surgical procedure on the lower body area of the patient 408. Specifically, the surgical robotics system 400A configures the set of robotic arms to manipulate a surgical instrument 410. The set of robotic arms insert the surgical instrument 410 along a virtual rail 490 into the groin area of the patient 408. Generally, a virtual rail 490 is a co-axial trajectory along which the set of robotic arms translates a surgical instrument (e.g., a telescoping instrument). The second robotic arm 470B, the third robotic arm 470C, and the fifth robotic arm 470E are coupled, e.g., holding, the surgical instrument 410. The first robotic arm 470A and the fourth robotic arm 470D are stowed to the sides of the surgical robotics system because they are not necessarily required to for the surgical procedure—or at least part of the surgical procedure—shown in FIG. 4A. The robotic arms are configured such that they manipulate the surgical instrument 410 from a distance away from the patient 408. This is advantageous, for example, because there is often limited space available closer toward the patient's body or there is a sterile boundary around the patient 408. Further, there may also be a sterile drape around surgical equipment. During a surgical procedure, only sterile objects are allowed pass the sterile boundary. Thus, the surgical robotics system 400A may still use robotic arms that are positioned outside of the sterile boundary and that are covered with sterilized drapes to perform a surgical procedure.

In one embodiment, the surgical robotics system 400A configures the set of robotic arms to perform an endoscopy surgical procedure on the patient 408. The set of robotic arms hold an endoscope, e.g., the surgical instrument 410. The set of robotic arms insert the endoscope into the patient's body via an opening in the groin area of the patient 408. The endoscope is a flexible, slender, and tubular instrument with optical components such as a camera and optical cable. The optical components collect data representing images of portions inside the patient's body. A user of the surgical robotics system 400A uses the data to assist with performing the endoscopy.

Figure 4B:
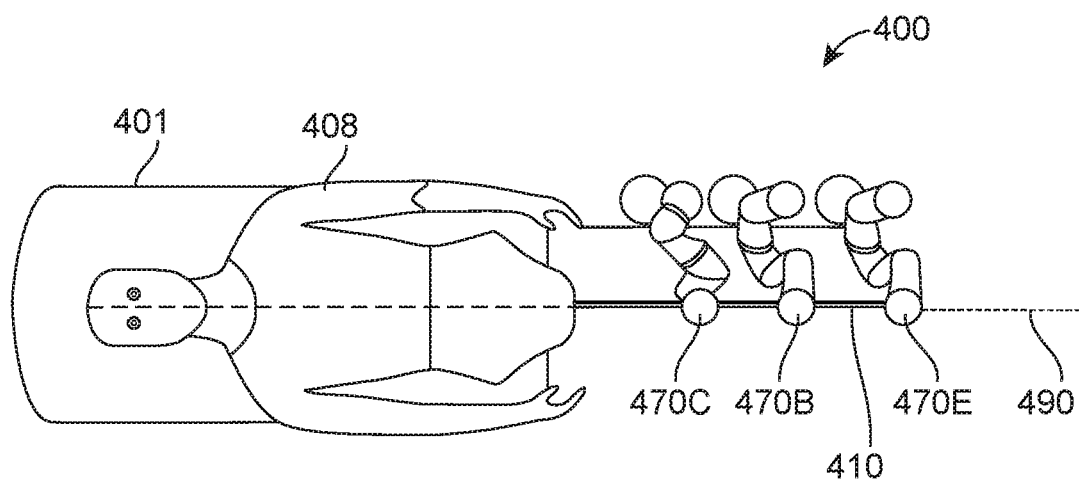
FIG. 4B is a top view of the surgical robotics system with column-mounted arms configured to access the lower body area of the simulated patient according to one embodiment.

FIG. 4B is a top view of the surgical robotics system 400A with column-mounted arms configured to access the lower body area of the patient 408 according to one embodiment.

Figure 4C:
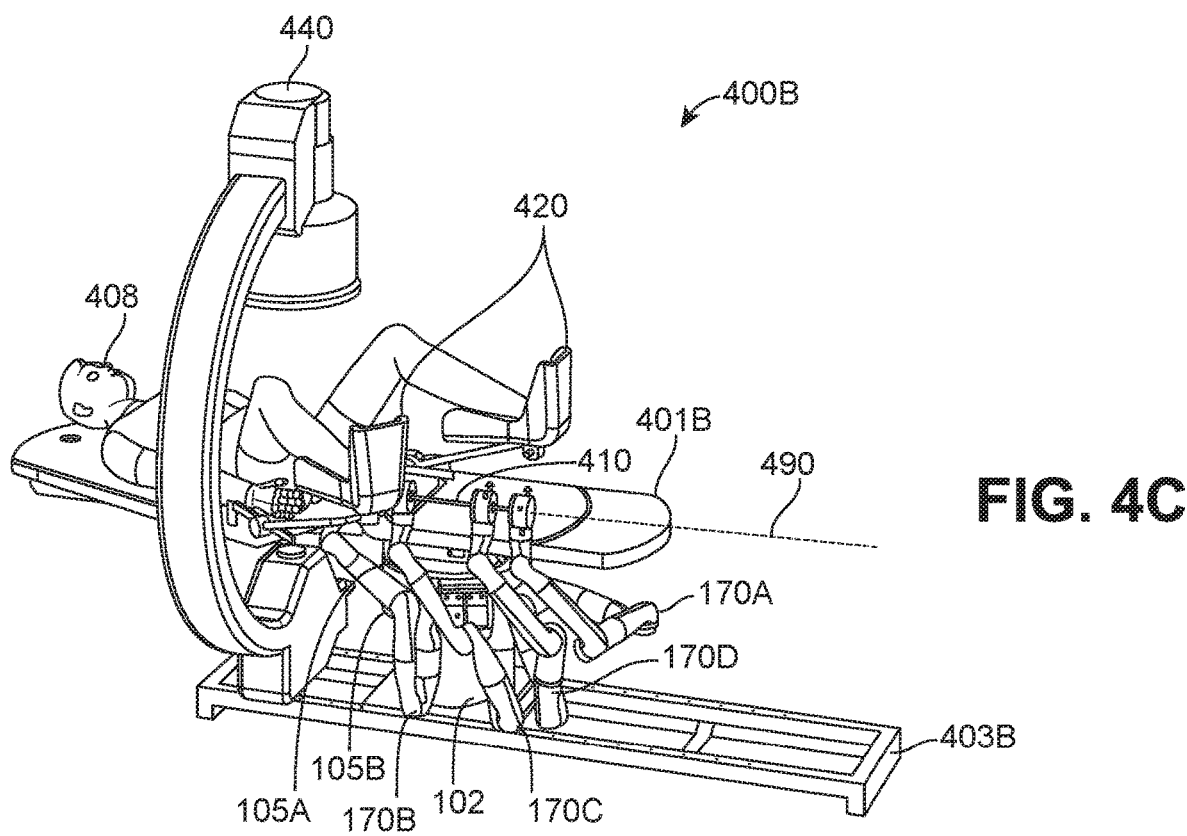
FIG. 4C is a perspective view of an imaging device and a surgical robotics system with column-mounted arms configured to access the lower body area of a patient according to one embodiment.

FIG. 4C is a perspective view of an imaging device 440 and a surgical robotics system 400B with column-mounted arms configured to access the lower body area of a patient 408 according to one embodiment. The surgical robotics system 400B includes a pair of stirrups 420 that support the legs of the patient 408 in order to expose the groin area of the patient 408. Generally, the imaging device 440 captures images of body parts or other objects inside a patient 408. The imaging device 440 may be a C-arm, also referred to as a mobile C-arm, which is often used for fluoroscopy type surgical procedures, or another type of imaging device. A C-arm includes a generator, detector, and imaging system (not shown). The generator is coupled to the bottom end of the C-arm and faces upward toward the patient 408. The detector is coupled to the top end of the C-arm and faces downward toward the patient 408. The generator emits X-ray waves toward the patient 408. The X-ray waves penetrate the patient 408 and are received by the detector. Based on the received X-ray waves, the imaging system 440 generates the images of body parts or other objects inside the patient 408. The swivel segment 210 of the table 119 is rotated laterally such that the groin area of the patient 408 is aligned in between the generator and detector of the C-arm imaging device 440. The C-arm is a physically large device with a footprint stationed underneath the patient during use. In particular, the generator of the C-arm is disposed underneath the operative area of the patient, e.g., the abdomen area. In typical surgical beds mounted to a column, the column interferes with the positioning of the C-arm generator, e.g., because the column is also underneath the operative area. In contrast, due to the configurability of the swivel segment 210, the surgical robotics system 400B may configure the table 119 such that the C-arm, the robotic arms, and a user (e.g., physician) have a sufficient range of access to perform a surgical procedure on a working area the patient's body. In one example use case, the table 119 is translated laterally along a longitudinal axis of the table 119 such that the robotic arms can access the groin or lower abdomen area of a patient on the table 119. In another example use case, by rotating the swivel segment 210 away from the column 121, the generator of the C-arm 440 may be positioned underneath the groin area of the patient 408. The swivel segment 210—with a patient lying on the swivel segment 210—may be rotated at least to 15 degrees relative to a longitudinal axis of the table 119 without tipping over the surgical robotics system. In particular, the surgical robotics system does not tip because the center of mass of the surgical robotics system (e.g., the center of mass of the combined, at least, table, bed, and base) is positioned above a footprint of the base.

The surgical robotics system 400B uses a set of column-mounted robotic arms to manipulate a surgical instrument 410. Each of the robotic arms is coupled to, e.g., holding, the surgical instrument 410. The surgical robotics system 400B uses the robotic arms to insert the surgical instrument 410 into the groin area of the patient along a virtual rail 490.

Figure 4D:
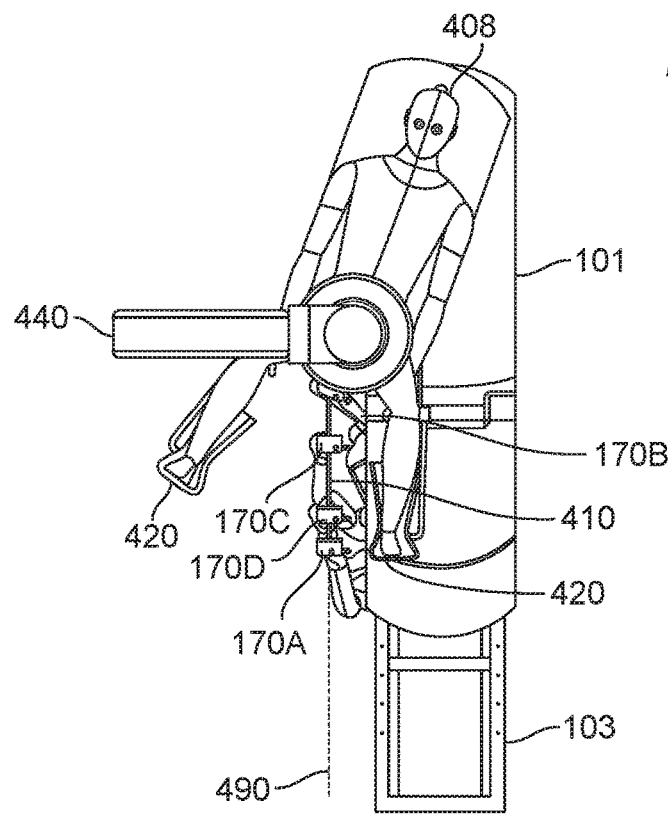
FIG. 4D is a top view of the imaging device and the surgical robotics system with column-mounted arms configured to access the lower body area of the patient according to one embodiment.

FIG. 4D is a top view of the imaging device 440 and the surgical robotics system 400B with column-mounted arms configured to access the lower body area of the patient 408 according to one embodiment.

III. Basket Apparatus

Figure 5A:
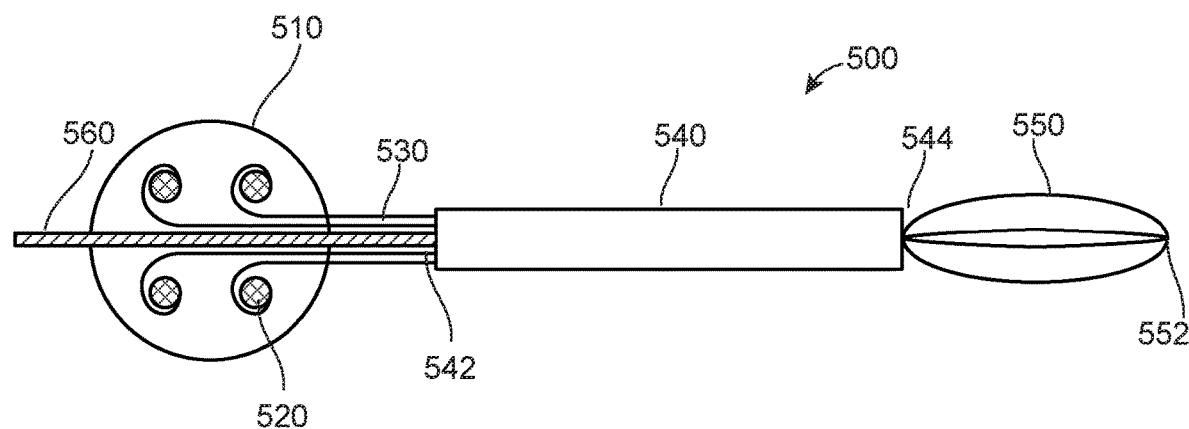
FIG. 5A is a side view of a basket apparatus according to one embodiment.
Figure 5B:
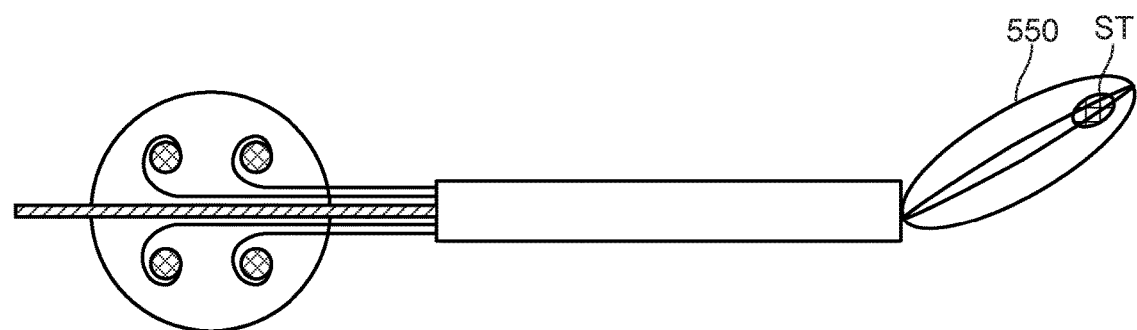
FIGS. 5B and 5C illustrate how the basket apparatus may be used to capture a kidney stone according to one embodiment.
Figure 5C:
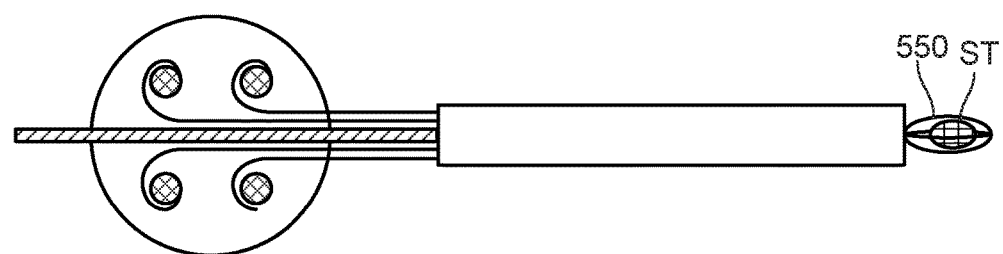

Referring now to FIGS. 5A to 5F, a robotically steerable basket apparatus is described. FIG. 5A is a side view of the basket apparatus. FIGS. 5B and 5C illustrate how the basket apparatus may be used to capture an object, such as a urinary stone, according to one embodiment. The robotically steerable basket apparatus 500 may be operatively and removably coupled to any of the IDMs described herein and above, such as IDM 117 described above. The robotically steerable basket apparatus 500 may be advanced through a natural or artificially created orifice in a subject or patient to capture a target object within the body of the subject or patient. For instance, the robotically steerable basket apparatus 500 may be advanced with the robotic surgical system 100 through the urethra, and optionally the bladder, ureter, and/or the kidney to capture a kidney stone (ST). As another example, the robotically steerable basket apparatus 500 may be advanced into the gallbladder to capture a gallstone. In some embodiments, the robotically steerable basket apparatus 500 may be advanced through another working channel of a catheter, ureteroscope, endoscope, or similar device (e.g., within a 1.2 mm diameter working channel). In those embodiments, the addition of an endoscopic instrument may provide axial support and stiffness, while also delivering additional features, such as vision, navigation, and localization capabilities, to the apparatus.

The robotically steerable basket apparatus 500 may include a handle or tool base 510 adapted to removably and operatively couple with the IDM 117. The tool base 510 may include a number of capstans 520 to couple to the output shafts or drive units of the IDM so that the IDM can actuate the capstans 520 as well as other actuation elements coupled thereto. The basket apparatus 500 further includes a number of pull wires (also referred to as tendons) 530. The pull wires 530 are coupled to the capstans 520 at one end. The pull wires 530 run straight along the long axis of the apparatus 500, and are prevented from sagging or twisting by an outer support shaft 540. The outer support shaft 540 may include a plurality of lumens and channels through which the pull wires 530 may traverse along the direction of the long axis of the apparatus 500. The outer support shaft 540 may be flexible to facilitate advancement of the basket apparatus 500 through a tortuous tissue tract or bodily channel, such as the urethra and ureter. The apparatus 500 may also include an internal shaft 560 for axial stiffness and support. The apparatus 500 may be configured to be inserted into the working channel of an instrument such as an endoscope 118.

The pull wires 530 may be coupled to one another at the distal-most tip 552 of the basket apparatus 500. For example, the basket apparatus 500 may include two different pairs of pull wires 530, with each pull wire pair forming a loop with the tips of the loops coupled to one another at tip 552 and each pull wire having its two ends threaded through opposite peripheral channels or lumens 548 of the outer support shaft 540. The two tips of the looped pull wires may be coupled together in any number of ways. For example, they may be soldered together, crimped together, braided together, bonded together with an adhesive, tied together with a suture or other thread, etc. Once connected together, each pair of pull wires forming a loop can also be referred to as a single pull wire, if that terminology is preferred in a particular implementation.

When the tool base 510 is coupled to an IDM, the capstans 520 may actuate the pull wires 530 so that the pull wires 530 can be translated proximally or distally in the axial (long axis) direction, such as relative to the outer support shaft 540. One or more of the pull wire 530 may be translated independently from one another, such as by their respective capstans 520.

The distal ends of the pull wires 530 may extend from the distal end 544 of the outer support shaft 540 to form a distal wire basket 550. The distal ends of the pull wires 530 may be retracted by the capstans 520 located at the proximal end 542 of the outer support shaft 540 to collapse the basket 550 into the outer support shaft 540. Retraction of the basket 550 into the outer support shaft 540 can lower the profile of the basket apparatus 500 to facilitate the advancement of the basket apparatus 500 into a tissue tract or bodily channel. In some embodiments, the apparatus 500 may be deployed through a working channel of an endoscopic device, wherein the apparatus 500 may be retracted relative to the endoscopic device in order to similarly lower the profile of the basket apparatus 500. Conversely, the capstans 520 may be actuated to extend the pull wires 530 out from the outer support shaft 540 so that the basket 550 may expand. For instance, once the distal end 544 of the outer support shaft 540 is positioned near a stone ST, the basket 550 may be expanded to capture the stone ST.

The basket 550 may be extended from outer support shaft 540 at different amounts of extension to vary the size of the basket 550. For instance, as illustrated in FIGS. 5B and 5C, the basket 550 may initially be extended to an enlarged size to capture the stone ST within the basket 550 and then the basket 550 may be partially collapsed (i.e., reduced in size) to secure the stone within the basket 550. As further shown in FIG. 5B, the pull wires 530 may be selectively actuated to steer or tip the basket 550 to facilitate capture of the stone ST. The outer support shaft 540 may be held stationary relative to the pull wires 530 while the pull wires 530 are differentially actuated. The basket 550 may be steered in any number of directions by the differential actuation of the individual pull wires 530 such that it has a 360° range of motion. For example, one end of an individual pull wire 530 may be held stationary while the other end is pulled or pushed to tip the basket 550 toward or away from the moving end, respectively. In other examples, the individual ends of the pull wires 530 may be differentially pulled, pushed, or held stationary to vary the degree and/or direction of the tipping.

The degree of movement of the capstans 520 may be indicative of the degree and/or direction of the tipping of the basket 550 and also of its current size. Therefore, in some embodiments, the robotic system, and the IDM in particular, can determine and/or track the current configuration of the basket 550 positioned within a subject or patient's body based on the feedback or information from the capstans 520, the drive unit(s), or output shaft(s) and without visualization of the basket 550. Alternatively or in combination, the basket 550 may be visualized to determine and/or track its current configuration. The pull wires 530 may be formed from a shape memory material or metal (e.g., a Nickel-Titanium alloy such as Nitinol) so that the distal ends of the pull wires 530 may be biased to assume the basket shape when unconstrained and/or at body temperature.

Figure 5D:
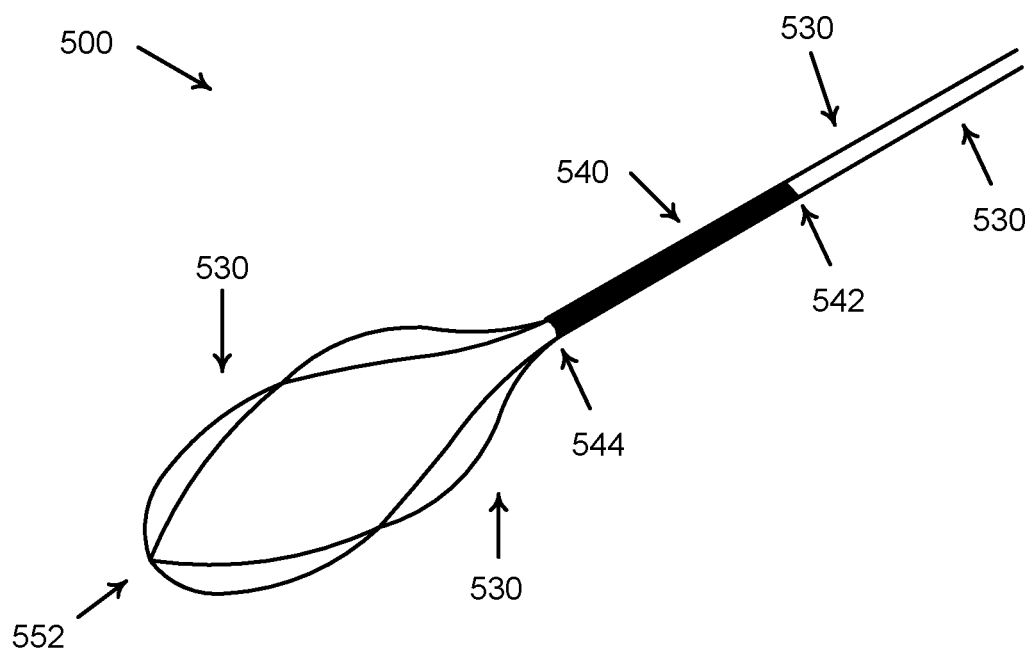
FIG. 5D shows a perspective view of the robotically steerable basket apparatus, according to one embodiment.
Figure 5E:
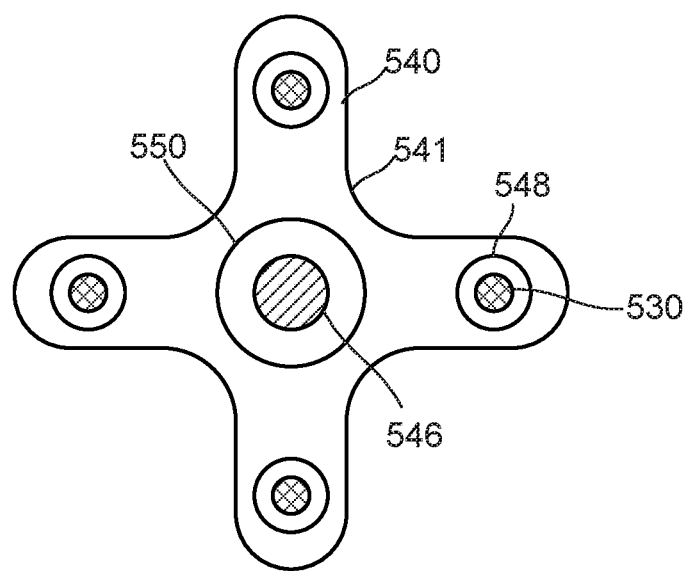
FIG. 5E shows a planar view of the robotically steerable basket apparatus along the plane perpendicular to the center axis of the outer support shaft, assuming it is straight, according to one embodiment.
Figure 5F:
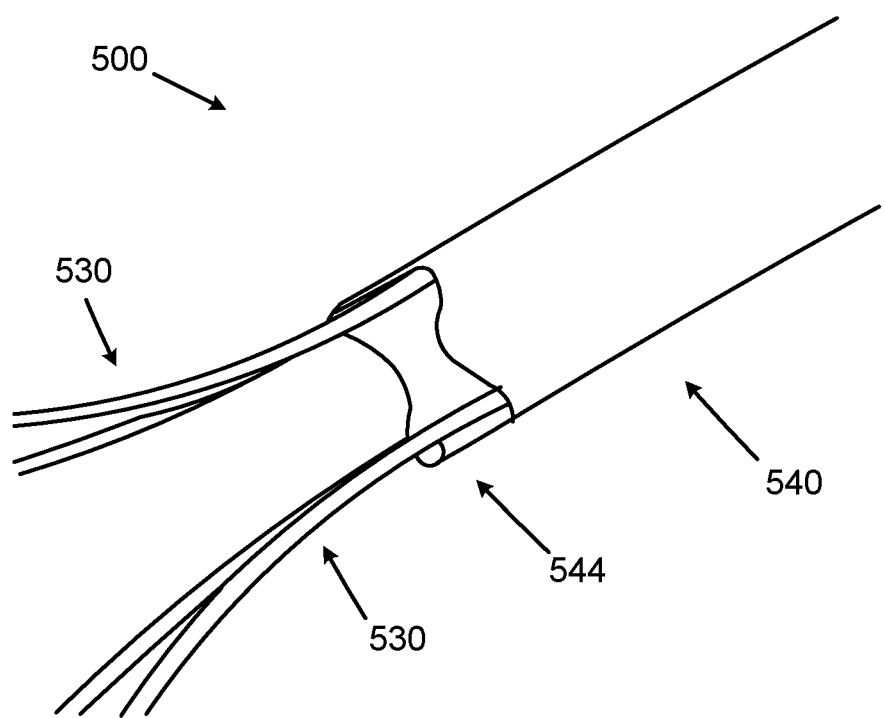
FIG. 5F and illustrates a close up view of the distal end of the outer support shaft of the basket apparatus, according to one embodiment.

FIGS. 5D, 5E, 5F illustrate different views of an embodiment that is intended for use within the working channel of an endoscopic device. FIG. 5D illustrates a perspective view of the outer support shaft of the basket apparatus, while FIG. 5E illustrates a close up side view of the outer support shaft. As shown in FIG. 5E, the outer support shaft 540 may have a square or diamond shaped cross-section. Other shapes such as a circle, ellipse, oval, triangle, quadrilateral, rectangle, pentagon, star, hexagon, and other polygonal shapes for the cross-section of the outer support shaft 540 are also contemplated. The outer support shaft 540 may include a central working channel 546 and a plurality of peripheral channels 548. The pull wires 530 may be positioned within the peripheral channels 548. A guide wire, a further therapeutic device (such as a laser fiber for lithotripsy), or a diagnostic device (such as an imaging device or a camera) may be advanced through the central channel 546 to reach a target area or object, such as a captured stone ST.

The outer support shaft 540 may also comprise a plurality of rounded vertices or corners 543 where the peripheral channels 548 are located and through which the pull wires 530 travel. Slotted lateral edges 541 on the outer surface of the outer support shaft 540 may be concave, and thus at least partially curved around the corners 543 where the peripheral channels 548 are located so as to define a plurality of elongate lateral slots or channels of the outer support shaft 540. These slotted lateral edges 541 may facilitate advancement of the basket apparatus 500 by discouraging apposition of tissue to the edges of the outer support shaft. When the basket apparatus 500 is positioned through a tissue tract, bodily channel, or the working channel of an endoscopic device, the slotted lateral edges 541 may provide sufficient space to allow fluid irrigation and/or aspiration between the outer support shaft 540 and the inner walls of the tissue tract, bodily channel, or working channel.

FIG. 5F shows a perspective view of a robotically steerable basket apparatus, such as the device in FIG. 5D, zoomed in to illustrate the distal end 544 of the outer support shaft 540 with the pull wires exiting the peripheral channels 548 according to one embodiment.

Figure 6A:
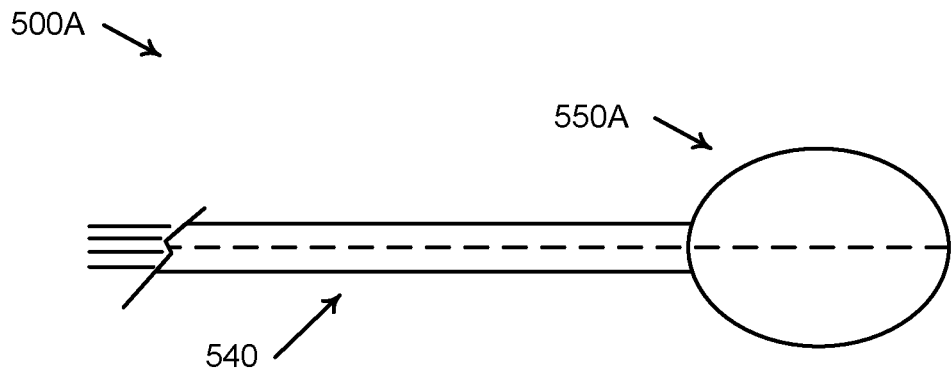
FIG. 6A illustrates an embodiment where the basket has have a spherical shape.
Figure 6B:
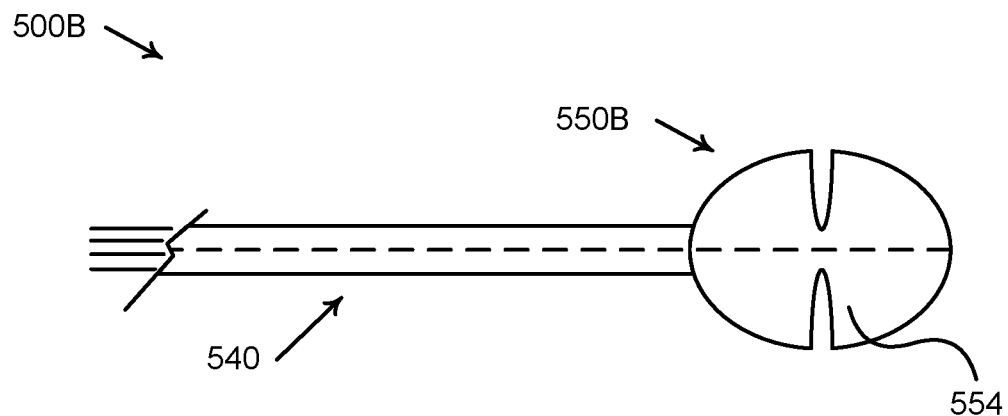
FIG. 6B illustrates an embodiment where the basket is shaped so as to form jaws.
Figure 6C:
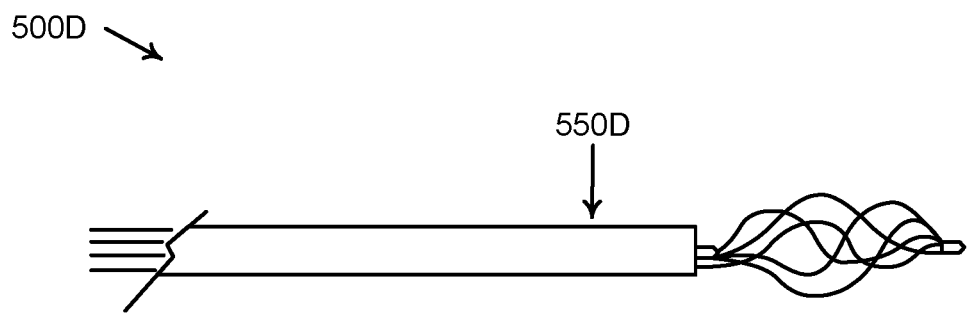
FIG. 6C illustrates an embodiment where the basket is formed of spiral or helically shaped pull wires.

FIGS. 6A-6C show example shapes for the expanded basket, according to one embodiment. When the basket 550 is expanded (e.g., not entirely collapsed with the outer support shaft 540, or extended past the distal end of an endoscopic device), it may have any number of shapes, such as an elliptical shape as shown in FIG. 5A. As an alternative, FIG. 6A illustrates an embodiment where the basket 550B has have a spherical shape. As another alternative, FIG. 6B illustrates an embodiment where the basket 550B is shaped to have the pull wires have a semi- or fully rigid indentation 554 so as to form the shape of "jaws" for improved reaching capabilities within tortuous anatomy. As another alternative, FIG. 6C illustrates an embodiment where the basket 550C is formed of spiral or helically shaped pull wires for alternative reaching capabilities within tortuous anatomy.

FIGS. 7A-7E illustrate various techniques for using the basket apparatus to break up a captured stone, according to one embodiment. The captured stone may be broken apart in many ways.

Figure 7A:
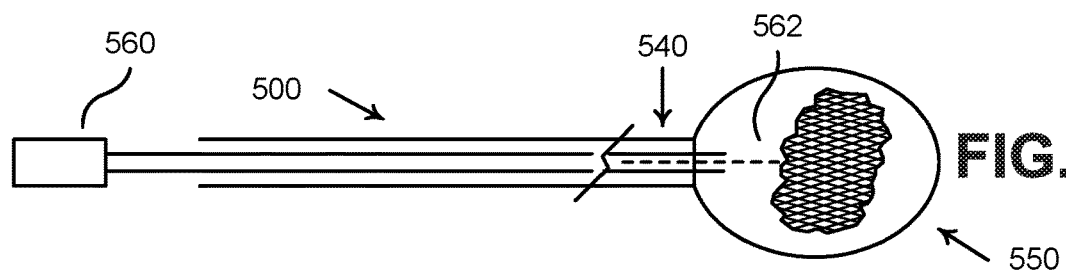
FIG. 7A illustrates insertion of a laser or optical fiber to break up a captured stone, according to one embodiment.

FIG. 7A illustrates insertion of a laser or optical fiber to break up a captured stone, according to one embodiment. The captured stone ST may be broken apart with laser or optical energy, referred to as laser lithotripsy. In such a use case, a laser or optical fiber 562 is introduced from the tool base or handle 510 and advanced through the central working channel 546 so that a laser tip or optical element is positioned at the proximal end of the basket 550. The central working channel 546 may have an appropriate size to accommodate the laser or optical fiber, such as 100-300 μm in diameter. The laser or optical fiber may convey laser or light energy to be directed by the laser tip or optical element to break apart the captured stone ST. Alternatively or in combination, a fluid may be flushed through or aspirated through the central working channel 546. Alternatively, a fluid may be flushed through or aspirated through slotted lateral edges 541 as discussed with respect to FIG. 5E.

The captured stone ST may be broken apart mechanically in many ways as well. For example, ultrasound may be applied such as through the central channel 546 (not shown). Alternatively or in combination, a mechanical device may be advanced through the central channel 546 and the mechanical device may be used to break apart the captured stone.

Figure 7B:
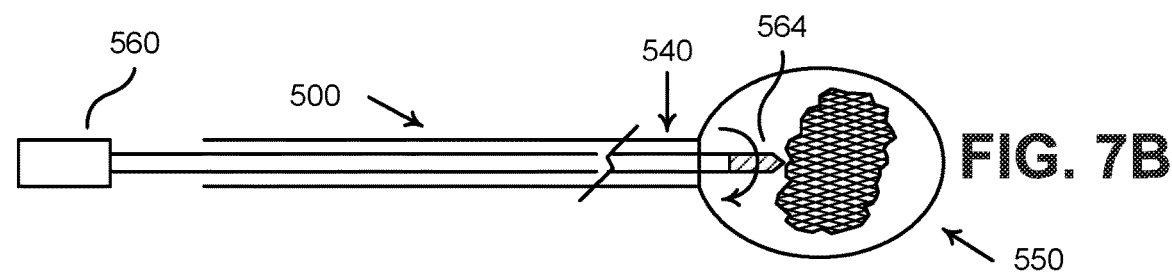
FIG. 7B illustrates insertion of a mechanical drill to break up a captured stone, according to one embodiment.

FIG. 7B illustrates insertion of a mechanical drill to break up a captured stone, according to one embodiment. The mechanical drill bit 564 is advanced through the central working channel 546 of the outer support shaft 540. A rotating motor, located proximal to the tool base 510, rotates the drill bit 564 at the basket 550 to break apart the captured stone ST.

Figure 7C:
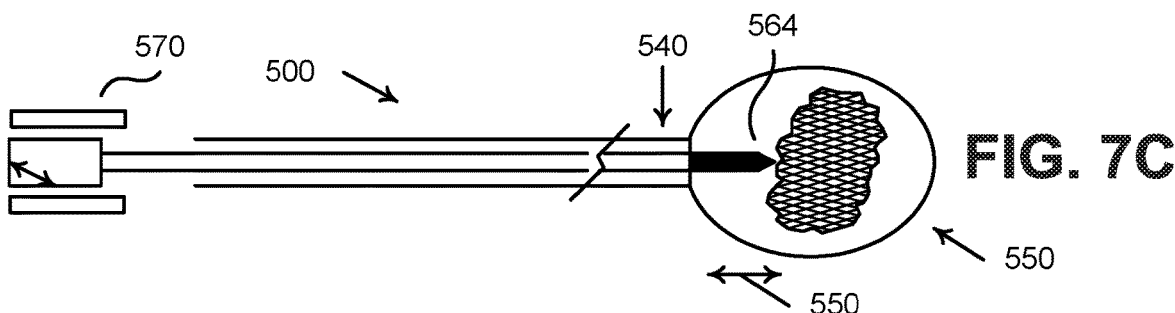
FIGS. 7C and 7D illustrate use of a chisel to break up a captured stone, according to one embodiment.
Figure 7D:
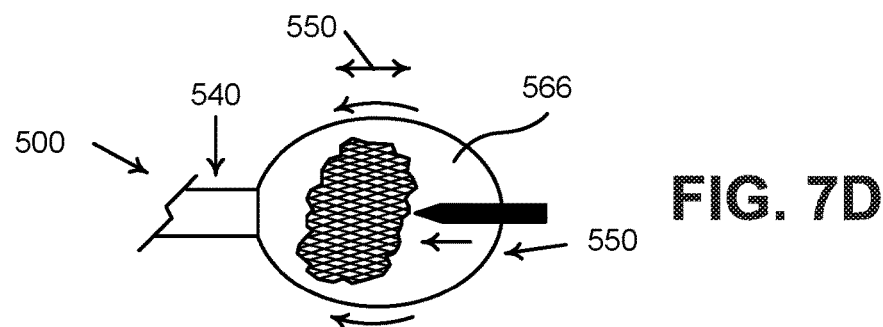

FIGS. 7C and 7D illustrate use of a chisel to break up a captured stone, according to one embodiment. In the embodiment of FIG. 7C, the chisel 566 is advanced through the central working channel 546 of the outer support shaft 540. The chisel 566 is actuated with a reciprocating motor (not shown) located proximal to the tool base 510. The reciprocating motor may drive the chisel 566 axially in the proximal and distal directions. In the embodiment of FIG. 7D, the chisel 566 is provided from a device separate from the apparatus 500, and thus is not advanced through the basket apparatus 500, to break apart the captured stone ST from another direction such as the distal direction. In this case, the working channel 546 of the basket apparatus 500 may be used to evacuate stone fragments.

Figure 7E:
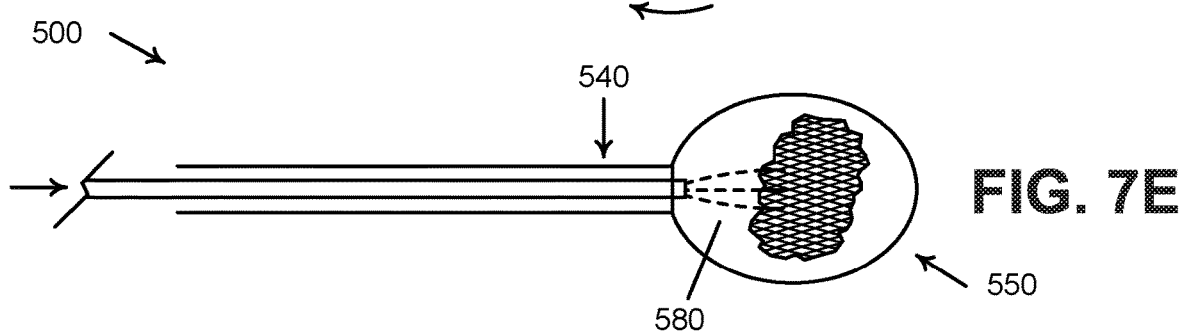
FIG. 7E illustrate use of a high pressure fluid jet to break up a captured stone, according to one embodiment.

FIG. 7E illustrate use of a high pressure fluid jet 580 to break up a captured stone, according to one embodiment. The high pressure fluid jet 5280 may be water, saline, or another liquid ejected from a fluid source. The fluid jet may be abrasive and comprise particulates such as salt particles to facilitate stone destruction. An example implementation may have a pressure of 400 psi and a 100 μm diameter on the central working channel 546 from which the fluid jet exits towards the stone ST.

The captured stone ST may be steered by the basket 550 while the captured stone ST is being broken apart. Once the captured stone ST is broken apart in any of the ways described, the broken apart stone ST may be aspirated through the central channel 546 and/or the broken apart stone ST may be secured by the basket 550 (such as in a lower profile than if the whole stone ST were secured) to be retracted from the target site (e.g., ureter, renal pelvis, gallbladder, etc.). In some embodiments, the broken apart portions of the captured stone ST may be aspirated while the basket 550 continues to capture and secure the larger portions of the captured stone ST that have not yet been broken apart.

IV. Process for Capturing Stones in a Basket Apparatus

IV.A. Problem

Basketing is a technique frequently used by urologists to remove urinary stones or stone fragments from the urinary tract. The current state of the art generally requires at least two experienced operator to control the ureteroscope and the basket apparatus in tandem. Procedure time and clinical outcome can be negatively impacted if one or more of the operators lack sufficient experience.

Current procedure for removing urinary stones involves advancing a ureteroscope into the ureter via the urethra and bladder. The ureteroscope is positioned approximately close to a urinary stone. During a basketing phase of the operation, a basket is advanced through the ureteroscope and may capture the urinary stone with its basket to extract the stone. With the ureteroscope positioned at the stone, the urologist has several potential workflow options for moving the stone. If the stone is small enough that the operator is able to capture the entire stone in the basket, then both the ureteroscope and the basket are withdrawn back to the bladder or outside the subject. If the stone is too big to withdraw in one pass, a laser (Holmium or neodymium-doped yttrium aluminum garnet (ND:YAG)) or a electrohydraulic lithotripsy (EHL) device can be passed through a central working channel of the ureteroscope and used to fragment the stone into smaller pieces. One operator can then exchange the laser fiber or EHL probe for the basket and can extract each stone fragment in turn to the bladder or outside the patient. If the stone is located in the proximal (relative to the center of the body of the subject) ureter or inside the kidney itself, a sheath can be used to enable rapid extraction and introduction of the ureteroscope and the basket.

Such a procedure requires two operators. The primary operator controls the ureteroscope and the secondary operator controls the basket or any other inserted tools such as the laser. Both the primary operator and the secondary operator can be looking at a visual feed from a ureteroscope camera.

Figure 8A:
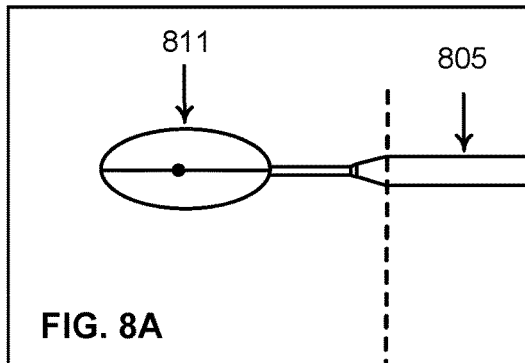
FIGS. 8A-8C illustrate a significant challenge that can face operators during a basketing operation, according to one embodiment.
Figure 8D:
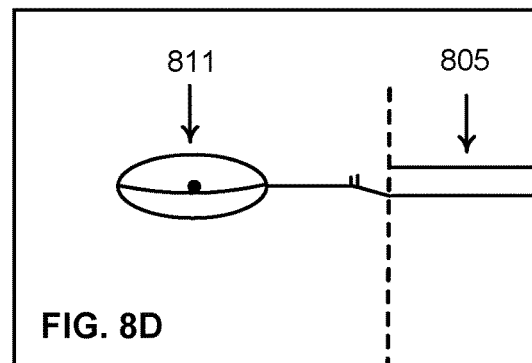
FIGS. 8D-8F illustrate a process for overcoming the challenge in basketing a stone, according to one embodiment.
Figure 8B:
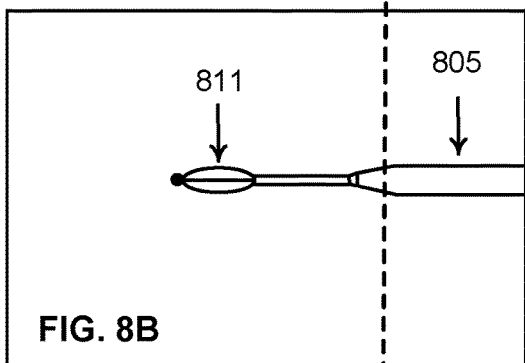
Figure 8E:
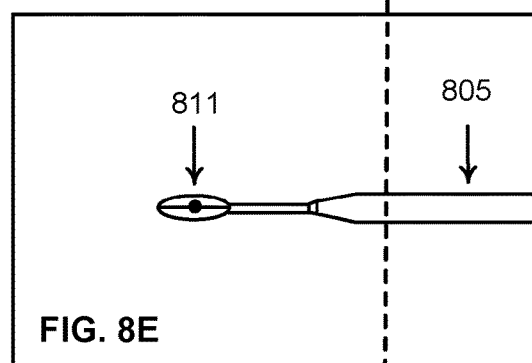
Figure 8C:
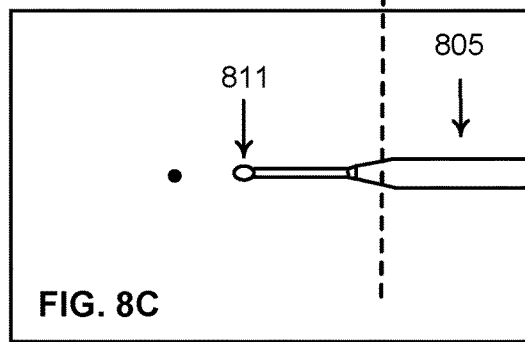

FIGS. 8A-8C illustrate a significant challenge that can face operators during a basketing operation, according tone one embodiment. In FIG. 8A, assume that the operator has advanced through the basketing phase to the point where the stone ST is now located within the open (i.e., unclosed or un-retracted) basket 802, by navigation of the basket, where the basket has been advanced out of the ureteroscope 805. Despite being located around the stone ST prior to retraction, retracting the basket 802 so that the stone ST is trapped in the basket 802 when the basket 802 is retracted is a significant challenge. This can be difficult because the center 811 of the basket 802 can retract laterally along the long axis of the basket as the operator closes the basket 802. In this scenario, if the operator initially positions the basket 802 center 811 over the stone ST (FIG. 8A) and closes or collapses the basket 802 (FIG. 8B), the basket 802 frequently retracts past the stone ST (see moved center 811 of the basket 802) and fails to trap it (FIG. 8C).

IV.B. Manual Process

Figure 8F:
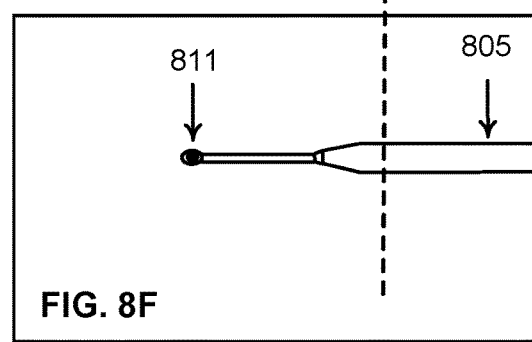

FIGS. 8D-8F illustrate a process for overcoming the challenge in basketing a stone, according to one embodiment. In this process, two operators work together to advance the ureteroscope 805 and/or the basket 802 in tandem as the basket 802 is closed to ensure the stone ST is trapped. FIG. 8D shows the basket 802 expanded and positioned to enclose the stone ST. FIG. 8E shows the basket 802 being collapsed while either the ureteroscope 805 or the basket apparatus (not explicitly shown, enclosed by the ureteroscope 805) is advanced, thereby holding the center 811 position of the basket in place relative to the stone ST. The ureteroscope 805 or basket apparatus may be moved relative to the pull wires through motion of either instrument as a whole by the operator. FIG. 8F shows the stone ST securely captured or trapped by the basket 802. After capture, the stone may be extracted from the patient by retracting the basket and/or the ureteroscope from the patient.

While the procedure above allows a stone ST to be more reliably captured, such a procedure typically requires two or more well trained operators who must work together with a high degree of coordination. For example, a first operator may be tasked with collapsing the basket with a first controller while a second operator may be tasked with advancing the basket apparatus with a second controller.

IV.C. Robotic Process

Robotic control can simplify the basketing phase operation, thus reducing the complexity of the procedure, the time to perform it. Robotic control also removes the need for more than one operator to be present to coordinate and accomplish the basketing phase.

FIGS. 9A-9F illustrate a process for positioning and controlling a basket apparatus to trap stones (and stone fragments) during a robotically assisted ureteroscopy intervention, according to one embodiment. The surgical robotics system 100 includes a robotically controllable ureteroscope 805 which itself includes a sheath component 815, a leader component (or leaderscope) 825, and a basket 802. Throughout the process, aspiration and irrigation/fluid transfer may be performed through the space between the leader and sheath through port 835, and/or they may be performed through the working channel of the ureteroscope, and through the slotted edges of an inserted basketing apparatus as described with respect to FIG. 5E above.

The system further includes at least two robotic arms 102A and 102B which are configured to control the position, orientation and tip articulation of the sheath 815 and leader 825, through instrument bases 801A and 801B for the sheath 815 and leader 825 respectively. In this example, at least one additional robotic arm 102C having a tool base 102C is configured to control the position and basket actuation of the basket 802. The system 100 may further include a graphical user interface suitable for controlling the ureteroscope 805 and basket 802, and a control system suitable for taking command inputs from the user interface and serving the appropriate motor of the appropriate arm 102. The arms 102A-C, particularly their bases 801A-C, may be aligned in a virtual rail configuration.

Figure 9A:
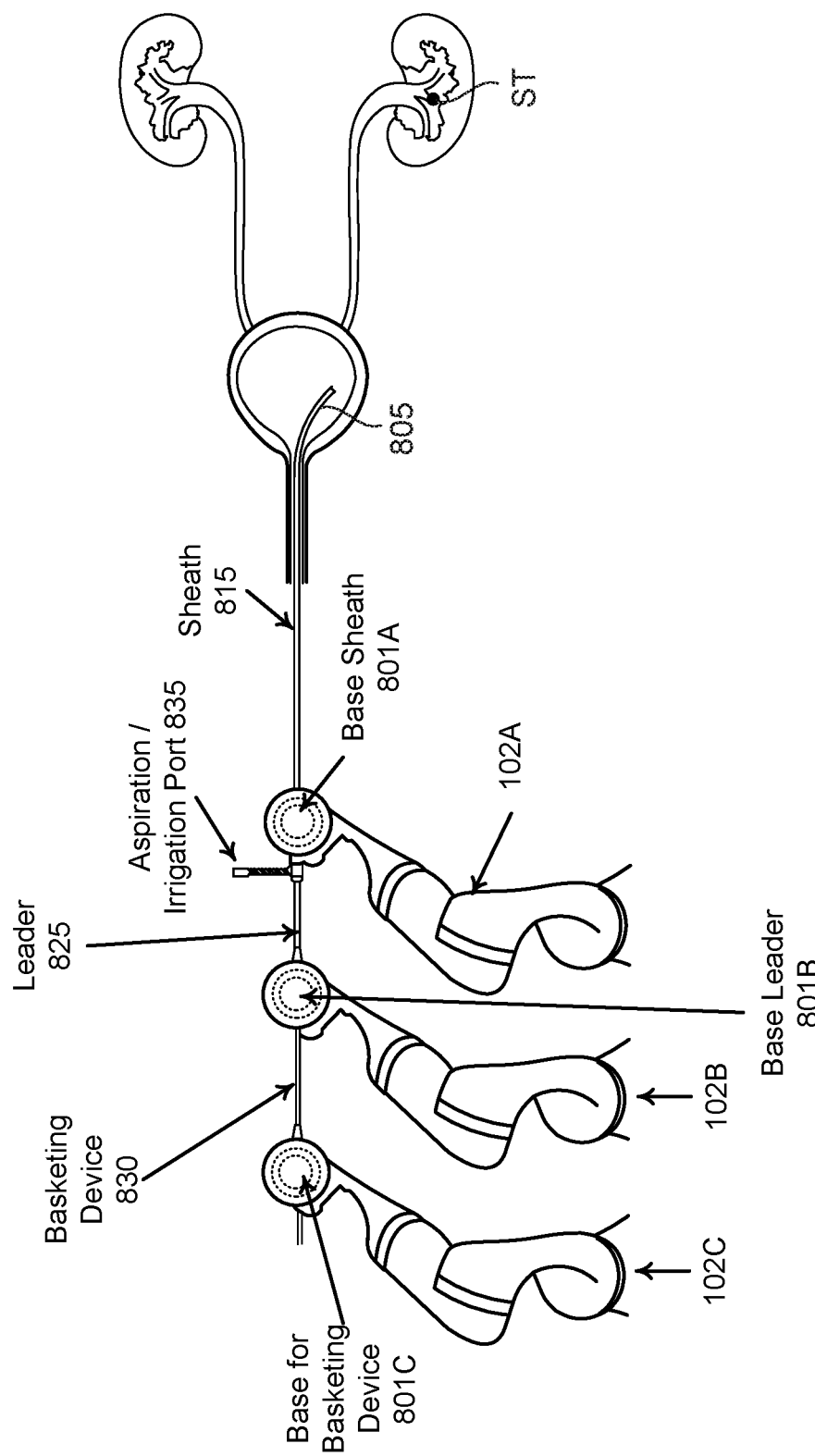
FIGS. 9A-9F illustrate a process for positioning and controlling a basket apparatus to trap stones (and stone fragments) during a robotically assisted ureteroscopy, according to one embodiment.
Figure 9B:
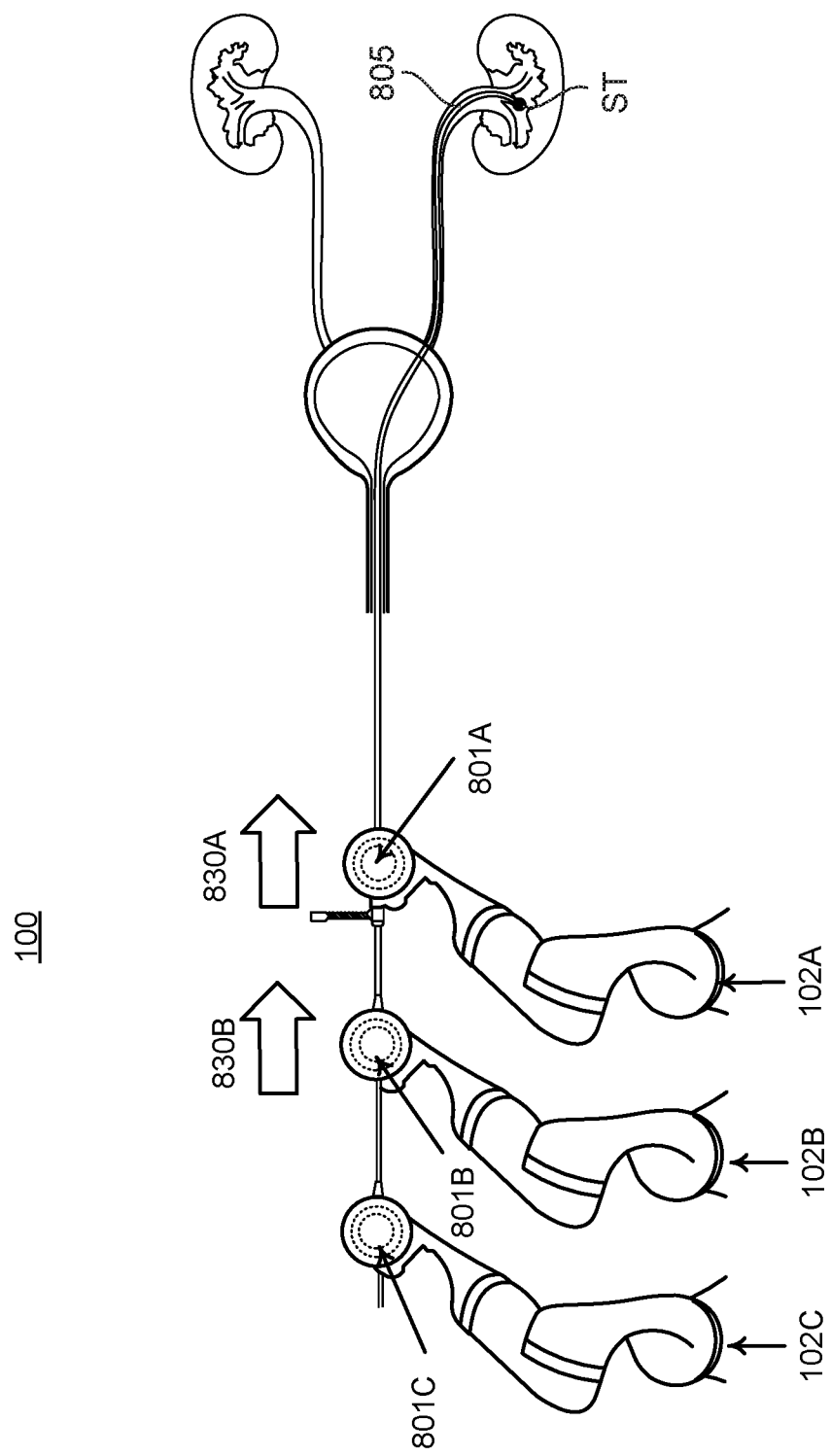
Figure 9C:
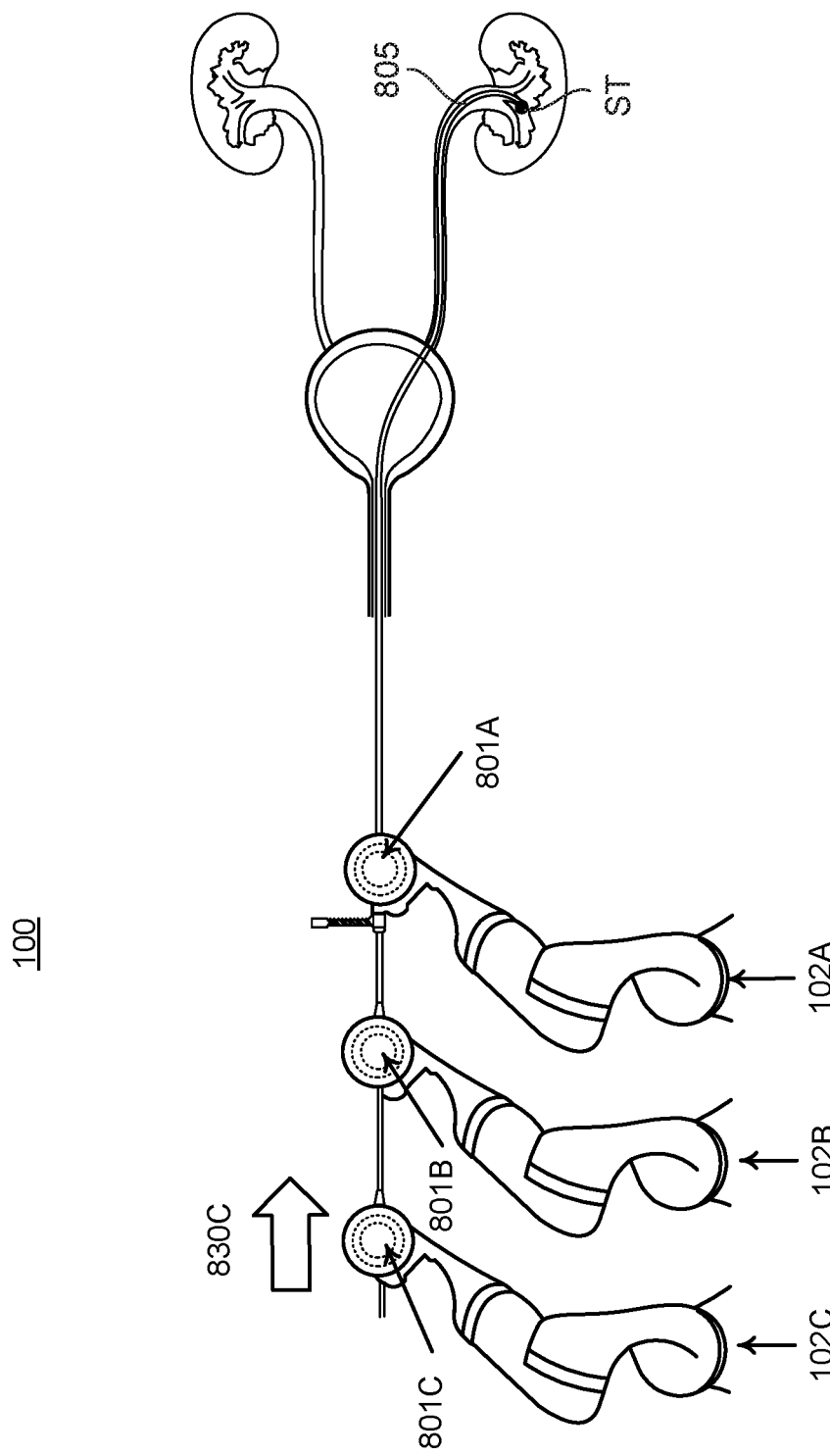

To carry out the process of the operation, the system 100 steers the robotic ureteroscope 805 (for example, either automatically or using operator input received via controls and displayed via the GUI) into position such that the stone ST can be visualized using a tip mounted camera (not shown) in the ureteroscope 805. As shown in FIG. 9B, the first 101A and second 101B instrument bases advance the sheath 815 and the leader 825, respectively, of the ureteroscope 805 relative to the patient in the directions indicated by a first arrow 830A and a second arrow 830B, respectively. The speed and magnitude of the motions of the sheath 815 and leader 825 may vary from each other, and the two parts may move independently from each other. The ureteroscope 805 is advanced through the bladder BL and the ureter UTR. As shown in FIG. 9C, the tool base 801C advances the basket 802 out of the working channel of the ureteroscope 805 in the direction indicated by a third arrow 830C. In one specific implementation of this process, an introducer, such as a rigid metal cystoscope, may be used to help insert the ureteroscope (sheath, leader, or both) into the patient's urethra.

Figure 9D:
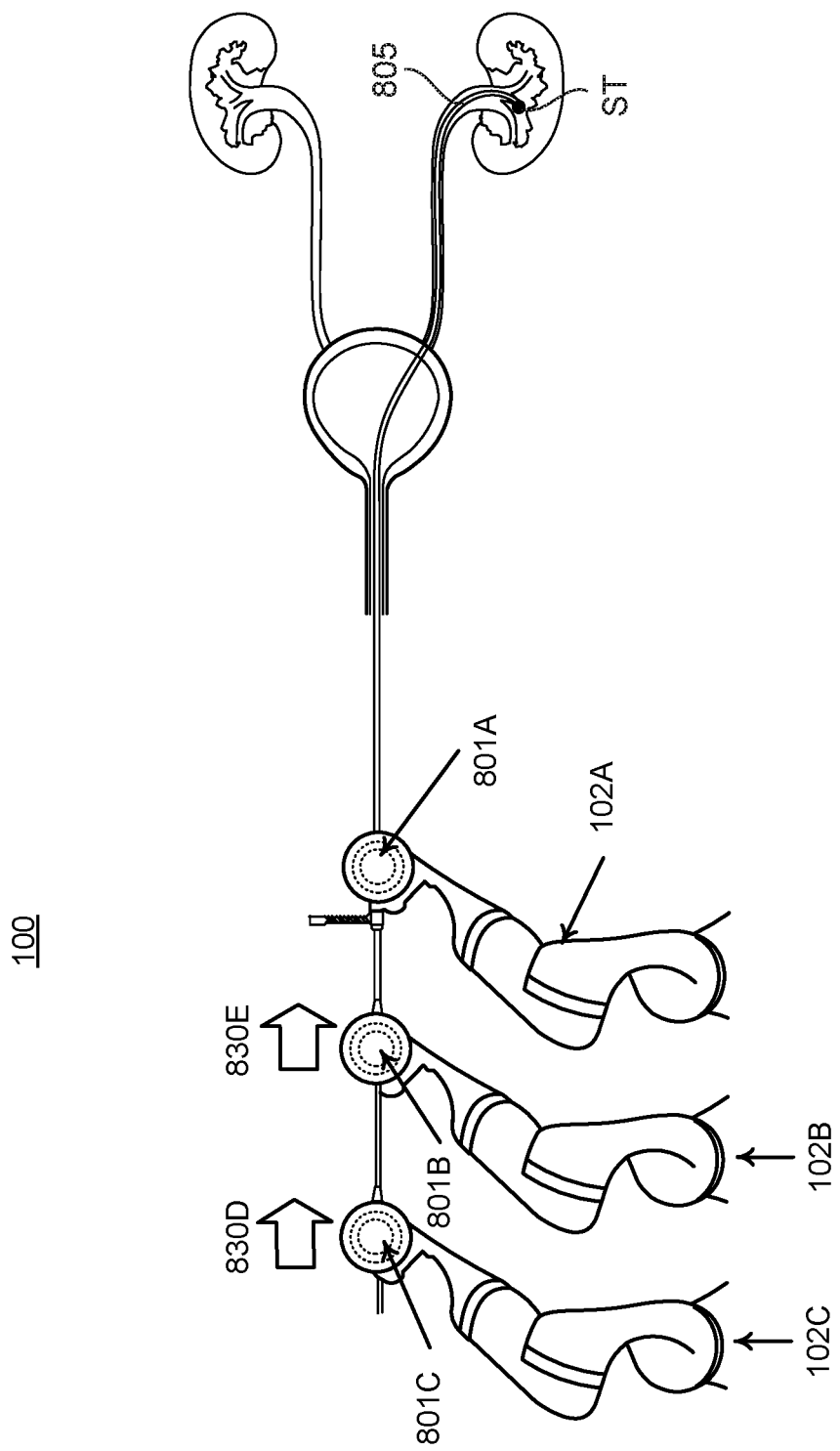

As shown in FIG. 9D, the system commands the basket 802 to open and positions the basket 802 such that the stone ST is located in the center of the basket 802. This may be accomplished, as shown by the fourth arrow 830D, by advancing one or more of the pull wires of the basket 802 using the tool base 801C, or using another arm/tool base (not shown) that separately controls the pull wires from the remainder of the basket apparatus. This may also be in part accomplished, as shown by the fifth arrow 830E, by advancing the leader 825 using the second instrument base 801B, which in turn repositions the basket 802 advanced out of the leader 825.

Figure 9E:
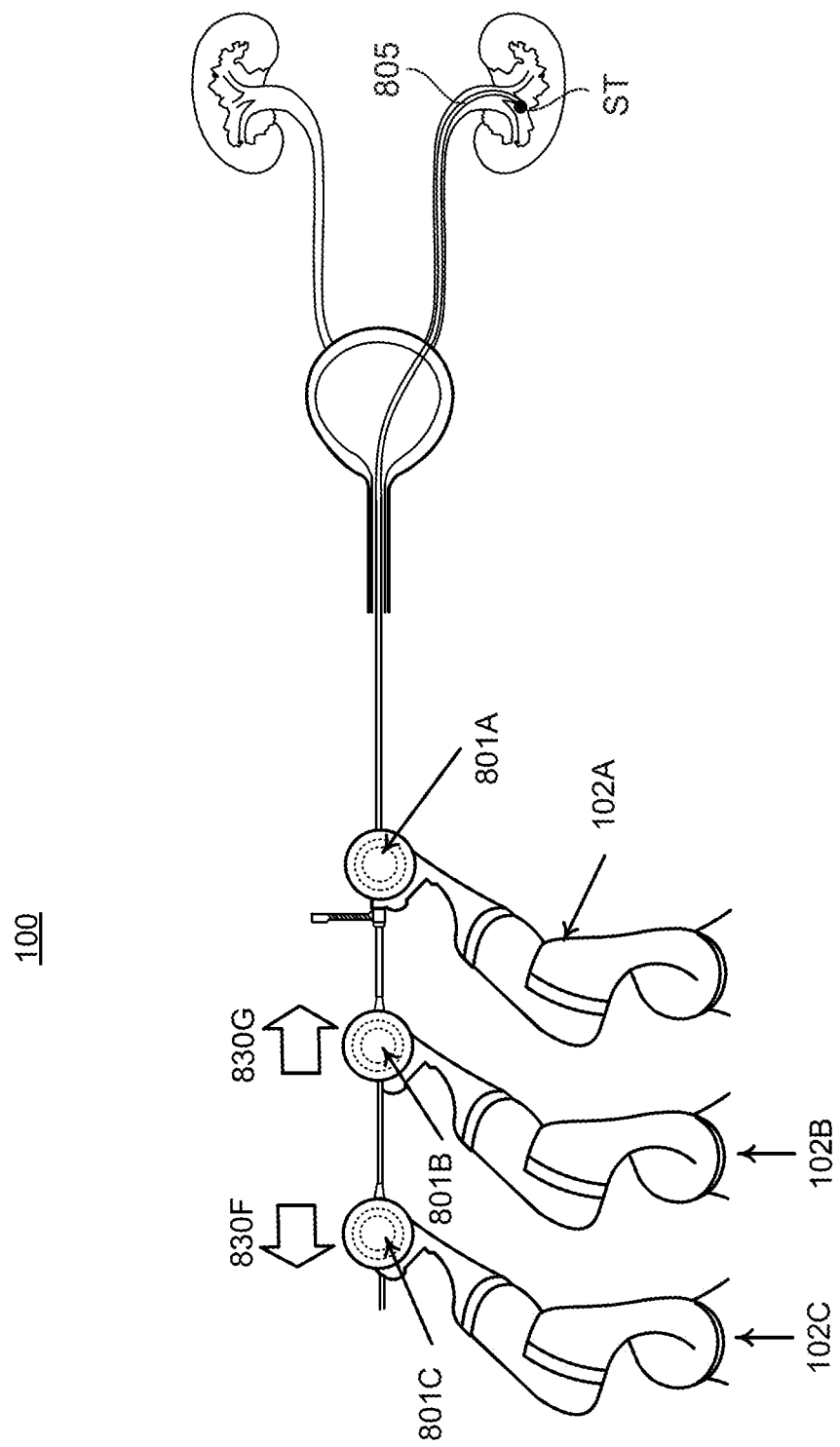

As shown in FIG. 9E, the system then commands the basket 802 to close. This may be accomplished, as shown by the sixth arrow 830F, by retracting the pull wires of the basket 802, again using the tool base 801C or using another arm/tool base (not shown) that separately controls the pull wires from the remainder of the basket apparatus. As the basket 802 closes, either the leader's 825 instrument base 801B or the basket apparatuses' tool base (not shown) may also simultaneously advance the leader 825 or the basket 802, respectively, in the direction indicated by seventh arrow 830G to maintain the stone ST in the center of the basket 802 while the basket is being closed until the stone ST is trapped.

Figure 9F:
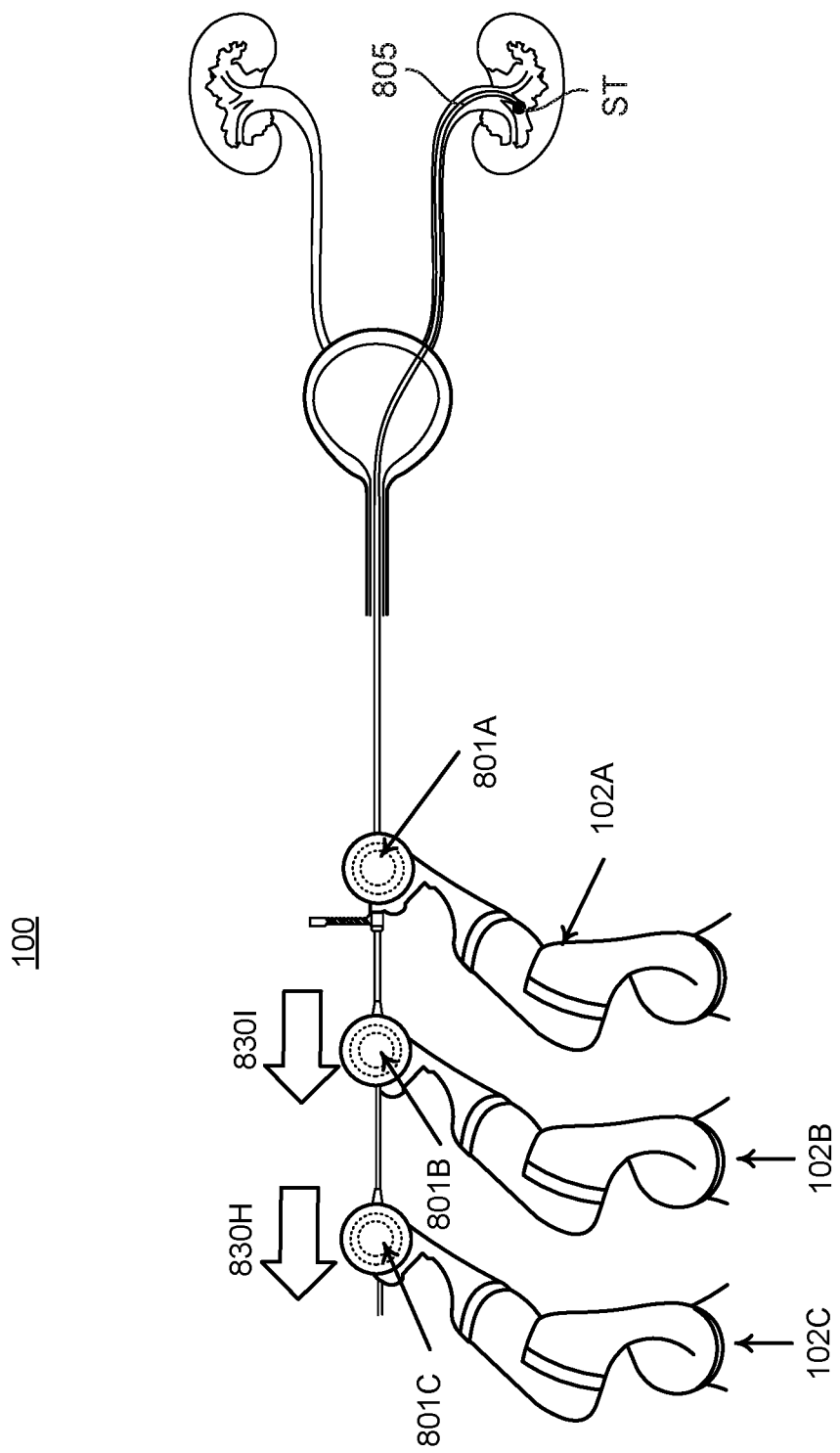

As shown in FIG. 9F, once the stone ST is trapped, the system removes or retracts the basket apparatus 802 and leader 825, according to the eighth 830H and ninth 830I arrows using the tool base 801C and instrument base 801B, respectively, from the subject so the stone ST can be fully extracted from the patient.

V. Process for Percutaneous Nephrolithotomy

V.A. Problem

Some ureteral stones are sufficiently large that removal via ureteroscope is impractical. For example, stones can be greater than 2 centimeters in diameter, and generally the working channel of a ureteroscope through which a stone or fragment can be removed has a diameter of 1.2 millimeters. Although breaking stones into smaller fragments for removal via ureteroscopy does work in many instances, studies have shown that leftover stone debris is often the source of new stone formation, necessitating future similar treatments.

Percutaneous nephrolithotomy (PCNL), in contrast, is a process for stone removal whereby a surgeon cuts into the kidney from outside the body (rather than entering through the ureter) to provide a larger port for stone removal. As no ureteroscope is used to identify the location of the stone within a kidney, the location of the stone must be identified by other mechanisms. A common technique is to use traditional imaging techniques, such as a X-ray computed tomography (CT) scan or fluoroscopy using an intravenous pyelogram, to identify the location of the stone.

Having collected this information it is common for a urologist, who is trained to remove the stone, to ask a radiologist to perform the percutaneous cut to place a guide wire leading near the location of the stone in the kidney out through the cut and outside the body. The cut may be obtained by directing a nephrostomy needle into the patient's body, the nephrostomy needle comprising of a stylet and a cannula. Having directed the needle into the patient, the stylet may be removed, leaving the cannula to form an open port to the location of the kidney stone. Through the cannula, the urologist may then place the guide wire. The urologist can then use this wire to perform the remainder of the PCNL process to remove the stone. It is common for a urologist to ask a radiologist to place the guide wire instead of placing it themselves because radiologists are specifically trained to generate and interpret CT scans, fluoroscopy scans, and other types of imaging that are used to identify objects such as kidney stone. They are further skilled as conceptualizing the imagery information in three dimensional (3D) space to identify the location of an object such as a stone in that 3D space, and consequently are the most skilled at placing a guide wire according to that information.

To complete the PCNL, the urologist uses the placed guide wire to pass a deflated balloon or dilator along the wire. The urologist inflates the balloon or dilator to create a port large enough introduce a hollow suction tube, such as a nephrostomy tube, directly into the calyx of the kidney containing the stone. At this point a nephroscope or any one of a number of other instruments may be introduced into the suction tube to assist in removing the stone. For example, a stone breaker, laser, ultrasound, basket, grasper, drainage tube, etc. may be used to remove the stone or fragments thereof. Drainage tubes, such as nephrostomy catheters, may be deployed down the suction tube to reduce intra-renal pressure during and after the PCNL is completed.

PCNL is advantageous because it allows removal of larger stones than ureteroscopy, and it further allows for better flushing of leftover stone sediment, which helps reduce new stone formation and therefore decreases the frequency of similar follow up treatments being needed. However, PCNL is also a more aggressive treatment than ureteroscopy, requiring a minor surgery and a longer recovery period. Further, the common need for a radiologist to perform part of the procedure in conjunction with the urologist adds additional cost, complication, and operation scheduling time delay to a procedure that would ideally need only the urologist and their staff to perform. Further, PCNL requires the use of imaging techniques that are cumbersome and affecting on the persons involved in the procedure. For example, fluoroscopy requires the use of lead vests to reduce radiation uptake by hospital staff. Lead vests, however, do not eliminate all radiation, and are cumbersome to wear for long periods, and over the course of an entire career can cause orthopedic injury to the staff.

V.B. Process

To address these issues, the following section describes a new process for PCNL including an alignment sensor to identify the location of a stone or the target calyx of interest. FIGS. 10A-10E illustrate an example of this process where the alignment sensor is an electromagnetic (EM) sensor (or probe). In this process, the EM sensor is introduced into through the bladder BL into the ureter UTR and onward into the kidney KD. The EM sensor may be attached to a ureteroscope that includes an EM sensor 1010 proximal to the tip of the ureteroscope 1005. Alternatively, the EM sensor may be as simple as a coil connected to an electrical wire running the length of the ureteroscope which is connected to an external computing device configured to interpret electrical signals generated at the coil and passed down the wire.

V.B.I. Pre-Operative Segmentation & Planning

A pre-operative planning process may be performed in order to plan the procedure and navigation of the robotic tools. The process includes performing a pre-operative computerized tomography (CT) scan of the operative region. The resulting CT scan generates a series of two-dimensional images that are used to generate a three-dimensional model of the anatomical pathways and organs. The process of partitioning a CT image(s) into constituent parts may be referred to as "segmentation." The segmented images are then analyzed by the system 100 to identify the locations in three dimensional coordinate space of landmarks within or on the surface of the patient. For PCNL, this analysis may include identifying landmarks including any one or more of the skin, kidney stone(s), bone structures (e.g., ribs, vertebrae, pelvis, etc.), internal organs (e.g., kidneys, liver, colon, etc.), and external devices (e.g., skin patch sensor). After segmentation is complete, a means of localization (such as electromagnetic detection discussed below or intra-operative fluoroscopy) may be used in combination with the locations of identified landmarks and a registration method to provide a visual representation of the location of medical tools/instruments within the anatomy.

V.B.II. Electromagnetic Detection

Generally, an EM sensor, such as a coil, detect changes in EM fields as the operator moves the EM sensor 1010 in the kidney KD, for example by moving the ureteroscope tip while locating the stone ST. An implementation of the process using an EM sensor thus further includes a number of EM generators 1015 located externally to the patient. The EM generators 1015 emit EM fields that are picked up by the EM sensor 1010. The different EM generators 1015 may be modulated in a number of different ways so that when their emitted fields are captured by the EM sensor 1010 and are processed by an external computer, their signals are separable so that the external computer can process them each as a separate input providing separate triangulation location regarding the location of the EM sensor 1010, and by extension the location of the stone ST. For example, the EM generators may be modulated in time or in frequency, and may use orthogonal modulations so that each signal is fully separable from each other signal despite possibly overlapping in time. Further, the EM generators 1015 may be oriented relative to each other in Cartesian space at non-zero, non-orthogonal angles so that changes in orientation of the EM sensor will result in the EM sensor 1010 receiving at least some signal from at least one of the EM generators 1015 at any instant in time. For example, each EM generator may be, along any axis, offset at a small angle (e.g., 7 degrees) from each of two other EM generators. As many EM generators as desired may be used in this configuration to assure accurate EM sensor position information.

V.B.III. On-the-Fly Electromagnetic Registration

EM data is registered to an image of the patient captured with a different technique other than EM (or whatever mechanism is used to capture the alignment sensor's data), such as a CT scan, in order to establish a reference frame for the EM data. FIGS. 11A-11D show example graphs illustrating on-the-fly registration of an EM system to a segmented 3D model generated by a CT scan of a path through a tubular network (e.g., from the bladder into a ureter into one of the kidneys), according to one embodiment.

FIGS. 11A-11D show example graphs 1110-1140 illustrating on-the-fly registration of an EM system to a segmented 3D model of a path through a tubular network, according to one embodiment. In the example of FIG. 11A-11D, the EM sensor is attached to an endoscope tip 11101, however the principles of registration described with respect to these figures are equally applicable to the case where an EM sensor is attached to a guide wire and the 3D model is replaced with intra-operative fluoroscopy. In such an implementation, the 3D model discussed in the following sections is replaced with fluoroscopy that updates a representation of the patient in with each fluoroscopy update as the guide wire is progressed through the patient. Thus, insertion of the guide wire towards the kidney and registration of the guide wire to external EM generators occur at least partially simultaneously.

Figure 11A:
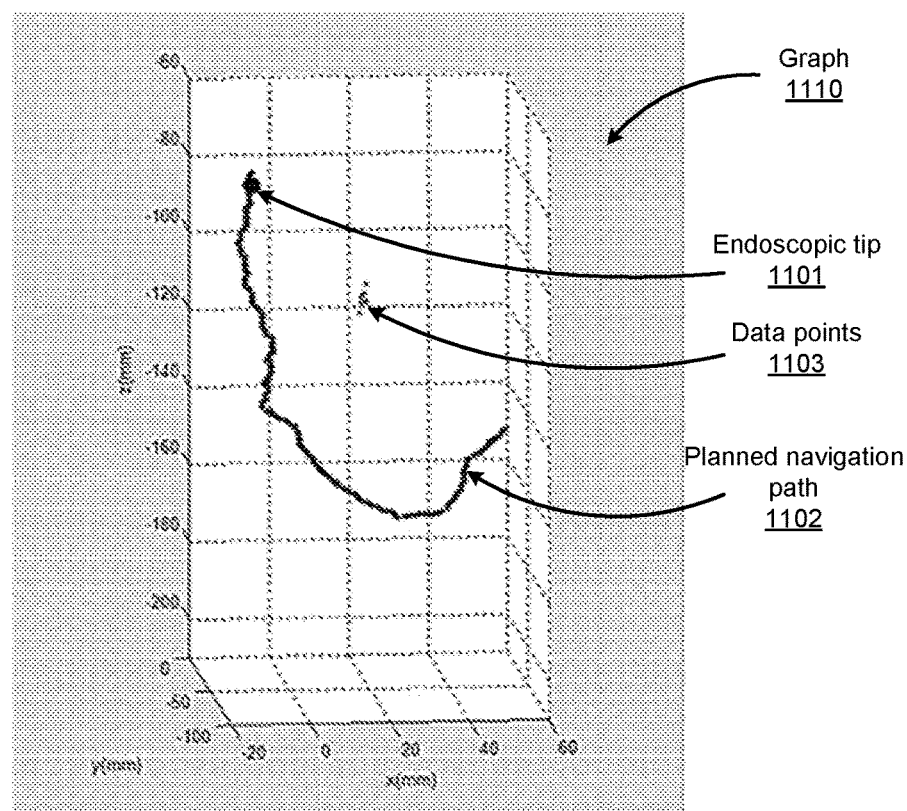
FIGS. 11A-11D show example graphs illustrating on-the-fly registration of an EM system to a 3D model of a path through a tubular network, according to one embodiment.

The navigation configuration system described herein allows for on-the-fly registration of the EM coordinates to the 3D model coordinates without the need for independent registration prior to an endoscopic procedure. In more detail, FIG. 11A shows that the coordinate systems of the EM tracking system and the 3D model are initially not registered to each other, and the graph 1110 in FIG. 11A shows the registered (or expected) location of an endoscope tip 1101 moving along a planned navigation path 1102 through a branched tubular network (not shown here), and the registered location of the instrument tip 1101 as well as the planned path 1102 are derived from the 3D model. The actual position of the tip is repeatedly measured by the EM tracking system 505, resulting in multiple measured location data points 1103 based on EM data. As shown in FIG. 11A, the data points 1103 derived from EM tracking are initially located far from the expected location of the endoscope tip 1101 from the 3D model, reflecting the lack of registration between the EM coordinates and the 3D model coordinates. There may be several reasons for this, for example, even if the endoscope tip is being moved relatively smoothly through the tubular network, there may still be some visible scatter in the EM measurement, due to breathing movement of the lungs of the patient.

The points on the 3D model may also be determined and adjusted based on correlation between the 3D model itself, image data received from optical sensors (e.g., cameras) and robot data from robot commands. The 3D transformation between these points and collected EM data points will determine the initial registration of the EM coordinate system to the 3D model coordinate system.

Figure 11B:
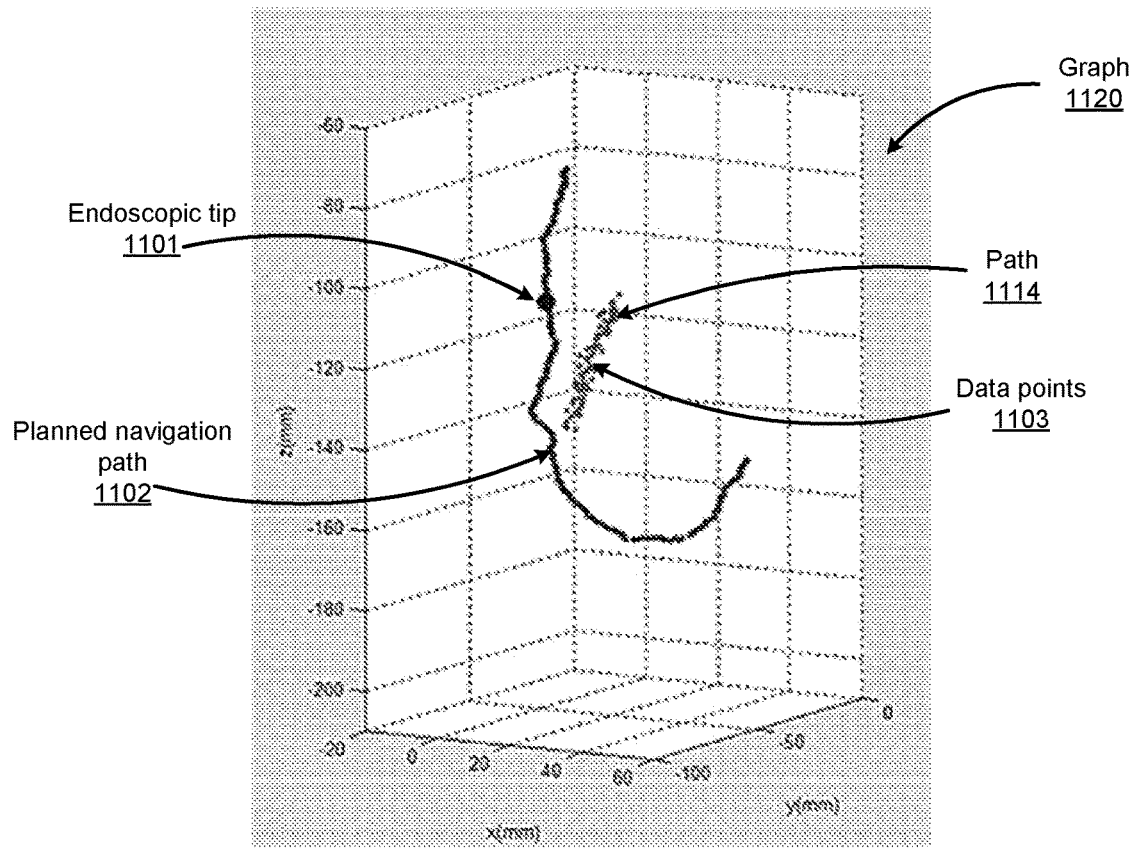

FIG. 11B shows a graph 1120 at a later temporal stage compared with the graph 1110, according to one embodiment. More specifically, the graph 1120 shows the expected location of the endoscope tip 1101 expected from the 3D model has been moved farther along the preplanned navigation path 1102, as illustrated by the shift from the original expected position of the instrument tip 1101 shown in FIG. 11A along the path to the position shown in FIG. 11B. During the EM tracking between generation of the graph 1110 and generation of graph 1120, additional data points 1103 have been recorded by the EM tracking system but the registration has not yet been updated based on the newly collected EM data. As a result, the data points 1103 in FIG. 11B are clustered along a visible path 1114, but that path differs in location and orientation from the planned navigation path 1102 the endoscope tip is being directed by the operator to travel along. Eventually, once sufficient data (e.g., EM data) is accumulated, compared with using only the 3D model or only the EM data, a relatively more accurate estimate can be derived from the transform needed to register the EM coordinates to those of the 3D model. The determination of sufficient data may be made by threshold criteria such as total data accumulated or number of changes of direction. For example, in a branched tubular network such as a bronchial tube network, it may be judged that sufficient data have been accumulated after arriving at two branch points.

Figure 11C:
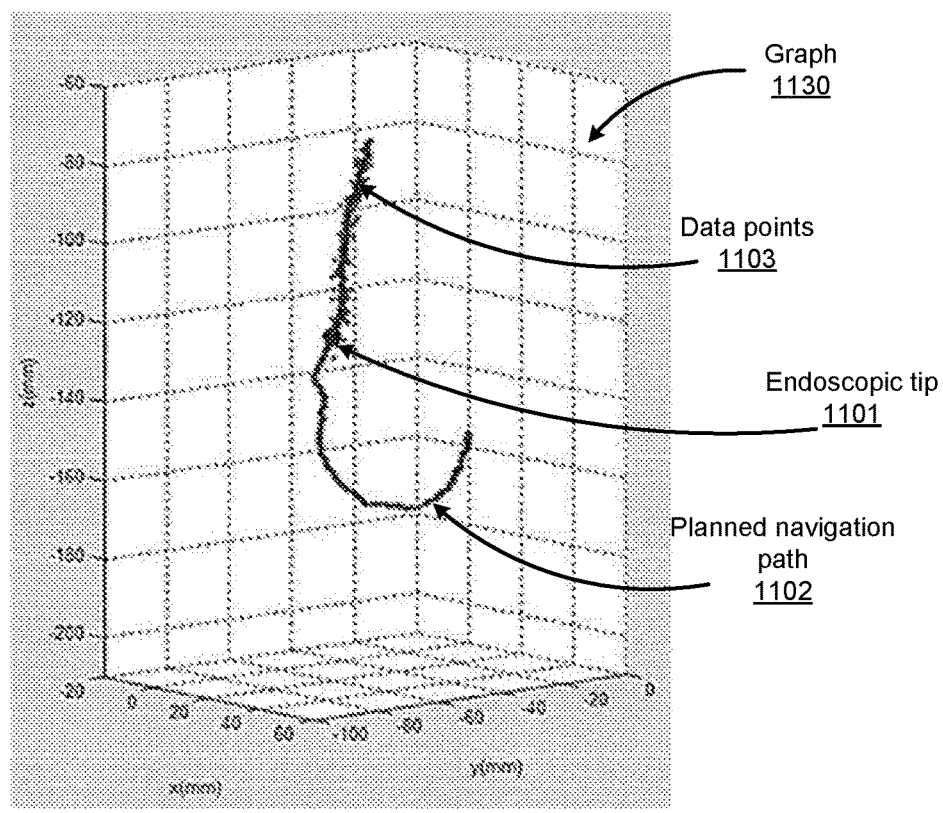

FIG. 11C shows a graph 1130 shortly after the navigation configuration system has accumulated a sufficient amount of data to estimate the registration transform from EM to 3D model coordinates, according to one embodiment. The data points 1103 in FIG. 11C have now shifted from their previous position as shown in FIG. 11B as a result of the registration transform. As shown in FIG. 11C, the data points 1103 derived from EM data is now falling along the planned navigation path 1102 derived from the 3D model, and each data point among the data points 1103 is now reflecting a measurement of the expected position of endoscope tip 1101 in the coordinate system of the 3D model. In some embodiments, as further data are collected, the registration transform may be updated to increase accuracy. In some cases, the data used to determine the registration transformation may be a subset of data chosen by a moving window, so that the registration may change over time, which gives the ability to account for changes in the relative coordinates of the EM and 3D models—for example, due to movement of the patient.

Figure 11D:
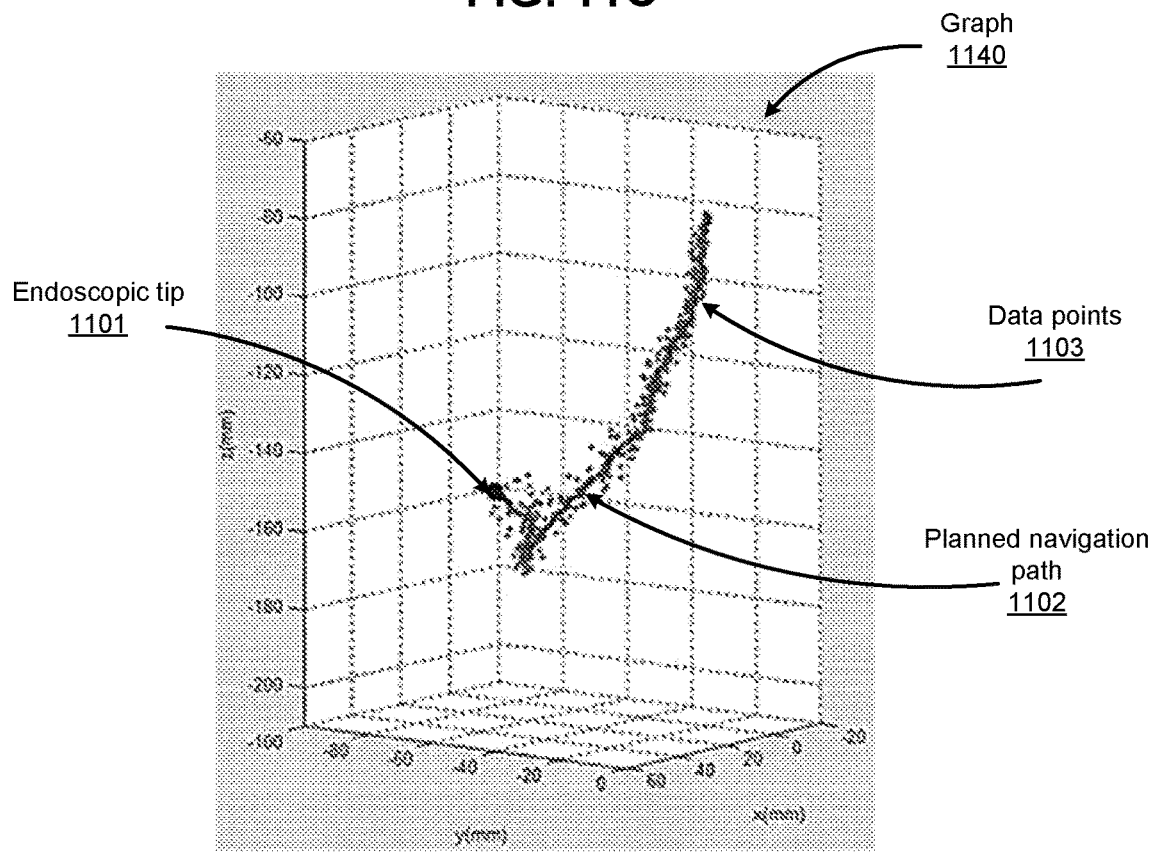

FIG. 11D shows an example graph 1140 in which the expected location of the endoscope tip 1101 has reached the end of the planned navigation path 1102, arriving at the target location in the tubular network, according to one embodiment. As shown in FIG. 11D, the recorded EM data points 1103 is now generally tracks along the planned navigation path 1102, which represents the tracking of the endoscope tip throughout the procedure. Each data point reflects a transformed location due to the updated registration of the EM tracking system to the 3D model.

Each of the graphs shown in FIGS. 11A-11D can be shown sequentially on a display visible to a user as the endoscope tip is advanced in the tubular network. Additionally or alternatively, the processor can be configured with instructions from the navigation configuration system such that the model shown on the display remains substantially fixed when the measured data points are registered to the display by shifting of the measured path shown on the display in order to allow the user to maintain a fixed frame of reference and to remain visually oriented on the model and on the planned path shown on the display.

V.B.IV Mathematical Analysis of Registration Transform

In terms of detailed analysis (e.g., mathematical analysis) and methods of the registration, in some embodiments, a registration matrix can be used to perform the registration between the EM tracking system and the 3D model, and as one example, the matrix may represent a translation and rotation in 6 dimensions. In alternative embodiments, a rotational matrix and a translation vector can be used for performing the registration.

$$M_1(\theta) = \begin{pmatrix} 1 & 0 & 0 \\ 0 & \cos\theta & \sin\theta \\ 0 & -\sin\theta & \cos\theta \end{pmatrix}$$

$$M_2(\varphi) = \begin{pmatrix} \cos\varphi & 0 & -\sin\varphi \\ 0 & 1 & 0 \\ \sin\varphi & 0 & \cos\varphi \end{pmatrix}$$

$$M_3(\psi) = \begin{pmatrix} \cos\psi & \sin\psi & 0 \\ -\sin\psi & \cos\psi & 0 \\ 0 & 0 & 1 \end{pmatrix}$$

From a perspective view of mathematical reasoning, as one example, applying a registration transform involves a shift from one coordinate system (x,y,z) to a new coordinate system (x',y',z') that may in general have its axes rotated to a different 3D orientation as well as having its origin shifted an arbitrary amount in each dimension. For example, a rotation to an azimuthal angle of radians $\theta$ may be expressed by the matrix $M_1$, a rotation to an inclination angle of y radians may be expressed by the matrix $M_2$ etc., and further rotational matrices may be written as the product of rotation matrices. Similarly, a translation vector of $(\Delta x\ \Delta y\ \Delta z)$ may be chosen to represent a translation of the origin in the x, y and z axes by $\Delta x$, $\Delta y$, and $\Delta z$ respectively.

The registration transform may be determined by such methods as singular value decomposition on a cross correlation matrix between measured EM positions and estimated positions in the 3D model. The transformation matrix components may then be extracted from the decomposition, e.g., by identifying the appropriate principle components. An error signal may also be generated from the residuals of the determined transform, and the size of the error signal may be used to determine a level of confidence in the position. As further data are taken and the registration transform is determined more accurately, this error signal may decrease, indicating an increasing confidence in positions estimated in this manner.

V.B.V. Registration Method Using Rigid Landmarks

The registration process may additionally or alternatively incorporate a rigid homogenous transformation (4×4) containing a rotation matrix and a translation vector. This transformation is obtained by a registration of one or more point sets, typically by generating the point sets via single value decomposition (SVD), iterative closest point (ICP) algorithm, or another similar algorithm. For PCNL, generating point sets for input into these algorithms may involve performing a gross registration by (i) selecting, as a first point set, easily identifiable rigid landmarks such as ribs, ASIS of the pelvis, and vertebrae (e.g., those identifiable on the outside of the patient) from the pre-operative CT images during the segmentation process, and/or (ii) intraoperatively capturing these landmarks, as a second point set, with the EM localization system through navigating/touching the landmarks with an EM probe or pointer. The targeted kidney stone may also be used as a landmark. In the case of the kidney stone, the stone's location may be captured via a EM sensor enabled ureteroscope or an EM probe attached to a guide wire. In order to reduce registration error, certain landmarks may be weighted differently within the algorithm workflow. In cases where a kidney stone obstructs the renal pathways, registration using rigid landmarks may be used independently.

In one embodiment, the registration process may include intra-operatively capturing registration data using a combination of a handheld EM probe, such as an embedded or "clipped-on" EM-enabled sensor to identify identifiable external rigid landmarks, such as ribs, ASIS of pelvis, and vertebrae, that does not disturb the PCNL workflow. Calibration of the sensor or sensor-embedded device may be achieved by a pivot test resulting in the correlation between the sensor's position and the probe's tip. In some embodiments, the probe may take the form and functionality of a marker pen.

V.B.VI. Locating a Stone Based on EM and Camera Information

Referring back to FIG. 10A, once the EM sensor data has been registered to the CT scan and the EM-enabled ureteroscope tip or guide wire with EM sensor has been advanced into the kidney KD, the operator is able to move the ureteroscope tip (or guide wire) to identify the location of a stone within the kidney or other patient organ. In the case of a ureteroscope, recall from the description of the tip in Section I.C above with respect to FIG. 3C, the ureteroscope may include a camera for capturing images of the field of view (FOV) in front of the tip. Camera data captured as a video or sequence of images allows the operator to navigate the kidney to look for the stone. Simultaneously provided EM data from a distally coupled EM sensor in the ureteroscope identifies the location of the ureteroscope tip within the kidney.

In some embodiments, an EM probe or guide wire may be deployed down the working channel of the ureteroscope to provide additional EM measurements for alignment. After deployment, the EM probe or guide wire may be extended out of the working channel and past the distal tip of the ureteroscope in order to provide an additional EM measurement. The EM measurement from the EM probe or guide wire may be used in conjunction with the EM data from the distally-mounted EM sensor in the ureteroscope in order to generate a vector (including position and orientation information), which may be used to define a trajectory for the percutaneous needle access to the operative region.

Figure 10A:
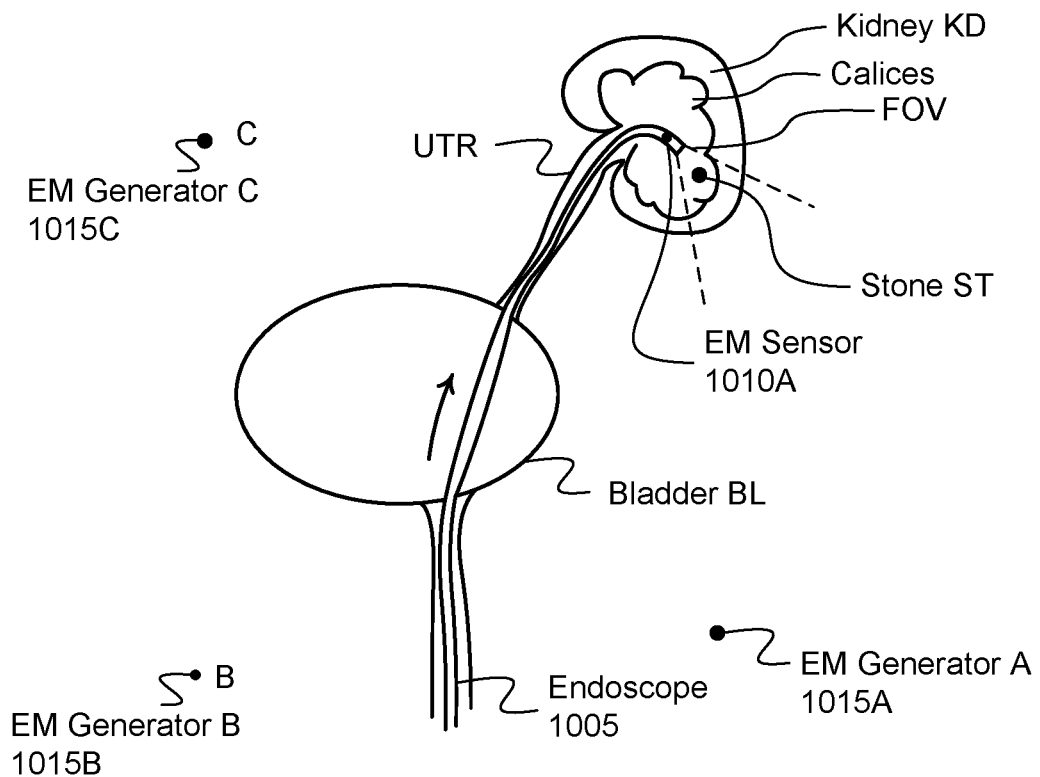
Figure 10B:
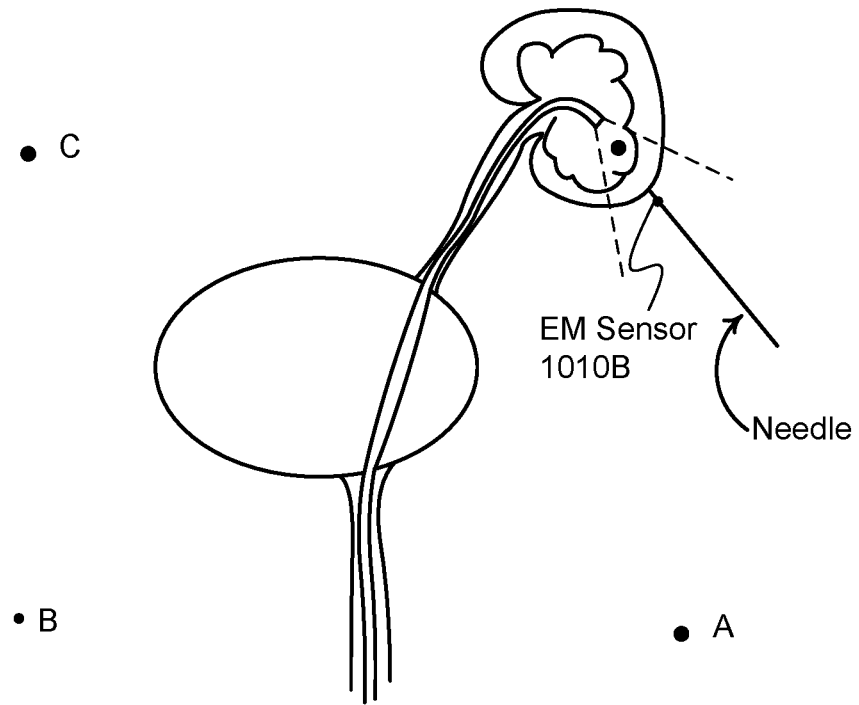

Once the stone has been located, for example by being present in the FOV of the camera on the tip, the percutaneous cut into the kidney can be performed. FIG. 10B illustrates the introduction of a needle to open a port from inside the kidney KD to outside of the patient, according to one embodiment. In this process, like the ureteroscope tip or guide wire, the needle also includes an alignment sensor such as an EM sensor. Similarly to the ureteroscope or guide wire, this may be a simple coil coupled to a wire running up the needle electrically coupled to the computer system. EM data received from the needle EM sensor may be received and processed similarly to ureteroscope tip or guide wire EM data as describe above.

FIGS. 10C and 10D illustrate sample views of a graphical user interface 1060 for visually presenting needle and ureteroscope (or guide wire) EM data, according to one embodiment. The EM data from the needle and the EM data from the ureteroscope tip are processed together by the external computing system to generate a graphical user interface that can be displayed to the operator to facilitate their guiding of the needle towards the stone position, as indicated by the ureteroscope EM data. As illustrated in FIG. 10C, in one embodiment, the location of the needle, as provided by needle EM sensor data, is indicated by a first graphical element, such as a line on the graphical display 1060A, whereas the location of the stone, as indicated by ureteroscope EM data, is indicated by a second graphical element, such as a point. As illustrated in FIG. 10D, as the operator inserts the needle into the patient's body and moves it towards the stone, the needle graphic (line) will generally move closer to the stone graphic (point) on the display 1060B. The positions of the graphics over time will indicate whether the operator is successfully moving towards the stone, or whether they are drifting off target. At any point, the ureteroscope may be separately repositioned to re-center the stone within the FOV, move the ureteroscope closer to or further from the stone, or look at the stone from a different angle to facilitate alignment and motion of the needle towards the stone.

The needle's motion may be constrained by the surgical robotics system performing the process or by design. For example, if the needle contains only a single EM sensor, the needle may not be able to provide information about the roll of the needle about its long axis. In this case, the needle will generally be able to move in 5 degrees of freedom (in/out, pitch +/−, yaw +/−, but not roll). In one embodiment, the X, Y, and Z axes of the system (and subsequently, through the GUI, the user) of the location of the tip of the needle in space relative to the target (ureteroscope tip) and relative to the anatomy (pre-operative CT that has been registered with the EM space and actual patient anatomy). The pitch and yaw of the needle tip informs the system of the current heading of the needle. With this information the system is able to project a predicted path onto the GUI to help the physician align the needle as he continues inserting it towards the target.

In other embodiments, additional EM sensors or other types of alignment sensor may be added more degrees of freedom may be permitted to the needle's motion. In yet other embodiments, the needle may be manually delivered by the physician using the guidance provided through the robotic system's GUI. For example, the introduction of a second EM sensor in the needle that oriented at a non-zero angle with respect to the first EM sensor can provide a roll degree of freedom, and the surgical robotics system 100 may be configured or designed to allow the operator to make a roll motion.

In addition to the basic GUI introduced above, additional graphical or auditory notifications may be provided to indicate that the needle has been positioned sufficiently close to the stone, that the needle has entered the kidney, that the needle has drifted sufficiently far off course, or any other trigger condition that may be warranted or requested by the operator. These notifications may change a color of the graphical user interface, sound a tone, or otherwise. The basic GUI may also be more comprehensive than illustrated in FIGS. 10C and 10D. It may also include an outline of the kidney, which will appear differently based on the orientation in 3D space of the ureteroscope tip and needle. It may further include outlines of the calices of the kidney and/or vasculature surrounding the kidney, as well as outlines of other organs or critical anatomy.

FIG. 10E illustrates a point in the PCNL procedure where the needle has penetrated the kidney near the stone, according to one embodiment. Once the needle has reached the stone, a balloon may be used to inflate the port, and a suction tube 1050 may be introduced to provide access to the kidney for insertion of larger diameter tools.

The PCNL process described above may be accomplished manually. Generally, the ureteroscope may be positioned first near the stone by a first operator. The same or a different operator may then insert the needle using the internal EM-sensor (via ureteroscope or guide wire) as a guide. In some embodiments, the EM sensor may be used to place a fiducial or beacon to assist the physician to return to the location of the stone or calyx, so that the endoscope or guide wire can be removed and does not need to be left in the patient to accomplish the same purpose. Alternatively, manipulation of the ureteroscope, guide wire, and needle may be accomplished by a surgical robotics system 100.

In an alternative embodiment, rather than using two different "live" alignment sensors attached to the needle and ureteroscope or guide wire as described above, the PCNL process may be carried out using only a single "live" alignment sensor attached to the needle. In one version of this embodiment, the EM system is registered using a pen or other another implement located outside the body with an attached EM sensor. The pen is used to identify landmarks of the patient's anatomy, and is rotated to register with respect to the EM generators. With this registration and landmark information, an operator or the surgical robotics system is oriented with respect to the patient's anatomy. Subsequently, the needle can be navigated towards the kidney (or other cavity) based on data provided by the EM sensor located in the needle, the landmark location information, and the registration information. An advantage of this approach is that it removes the need for separate navigation of an instrument with an EM sensor into the patient in order to determine where to direct the needle. The loss of precision provided by the EM sensor close to the stone or other object can be at least partially compensated for by the landmark registration process.

The advantages of the above-described process for placing the needle and associated port are numerous. Navigation of the needle is made less skill intensive using the ureteroscope or guide wire as a guide. A single operator or robotic system may carry out the process. Fluoroscopy can be omitted if desired.

Although the above process has been described with the alignment sensor being an EM sensor (and associated EM generators), in practice other kinds of positioning sensors may be used instead. Examples include, but are not limited to, accelerometers and gyroscopes, magnetometers, fiber optic shape sensing (e.g., via Bragg gratings, Rayleigh scattering, interferometry, or related techniques), etc. Depending on the implementation, registration to a separate form of patient imagery, such as a CT scan, may or may not be necessary to provide a frame of reference for locating stones within the patient.

Further, this process may be used in other operations beyond PCNL, such as gallbladder stone removal, lung (pulmonary/transthoracic) tumor biopsy. Generally, any type of percutaneous procedure may be performed by using an endoscope with an alignment sensor and a needle with a similar alignment sensor. In each of these processes, the alignment sensor-equipped endoscopic tip entered through a patient cavity into a patient organ provides a guide for the insertion of the alignment sensor-equipped needle. Additional examples include stomach operations, esophagus and lung operations, etc. Further, the objects to be removed do not necessarily need to be urinary stones, they may be any object, such as a foreign body or object created within the human body.

V.B.V. Stone and Fragment Removal

With the suction tube in place, a variety of techniques may be used to remove a stone. Various instruments may be inserted into the suction tube or ureteroscope to break up or remove the stone and stone fragments. Examples include the basket apparatus described above, a laser or optical fiber to break up stones via lithotripsy, an ultrasound device to break up stones via shockwaves, a blender, chisel, or drill to break up stones mechanically, and so on. Alternatively, the various instruments described above may be coupled or integrated into the suction tube in order to assist in the breaking up of kidney stone fragments and debris to assist aspiration using the suction tube.

In one embodiment, once the suction tube is in place and given that the ureteroscope is already in place near the stone, any other instrument taking up the working channel is retracted from that ureteroscope. This may, for example, be the EM sensor itself or another instrument. A basket apparatus, such as the one described above in Section III, or another grasping tool, i.e., grasper, may then be inserted into the working channel of the ureteroscope. and is extended out past the ureteroscope tip near the stone.

The basket apparatus (or other similar device) may be used to capture the stone and place it near the opening at the distal end of the suction tube within the patient organ, where instruments coupled to the suction tube, deployed down the suction tube, or deployed down the working channel of the ureteroscope may break up the stone in order to assist aspiration of the material down the suction tube. Additionally or alternatively, lithotripsy may be performed (using a laser tool inserted through the working channel of the basket apparatus, ureteroscope, or deployed down or attached to the suction tube) to break up the stone so that it can be sized to fit through the suction tube.

During the procedure, suction (negative pressure) may be applied down the suction tube in order to aspirate the stone or any stone fragments that are generated, while the ureteroscope or basket apparatus continuously irrigates the operative area. Simultaneous irrigation and suction helps maintain pressure in the patient cavity. In embodiments where the ureteroscope may comprise of both a sheath component and a leader component, i.e., a leaderscope, the irrigation fluid may be provided through the working channel of the sheath component, in order for the working channel of the leader component to remain available for tool deployment, such as a basket apparatus or a grasper, to help position and move the stone into closer proximity to the suction tube for aspiration.

Consequently, any instruments extending out of the ureteroscope and the suction on the suction tube operate in tandem to allow capture and removal of the stone or stone fragments from the kidney. Due to the presence of both the suction tube and the surgical tool, whether it be a basket apparatus or other grasping tool, the removal of the stone effectively proceeds as if the operator had two "hands" present within the kidney to deal with the removal of the stone, along with simultaneous vision of the operating area as provided by the camera on the tip of the ureteroscope.

VI. Additional Considerations

The processes described above, particularly those for controlling the arms of the surgical robotics system, processing alignment sensor data to generate position and orientation information for the alignment sensor and/or needle, and for generating a graphical user interface to display this information may all be embodied in computer program instructions stored within a non-transitory computer-readable storage medium, and designed to be executed by one or more computer processors within one or more computing devices. The non-transitory computer-readable medium can be stored on any suitable computer readable media such as RAMs, ROMs, flash memory, EEPROMs, optical devices (CD or DVD), hard drives, floppy drives, or any suitable device. The computer-executable component is preferably a processor but the instructions may alternatively or additionally be executed by any suitable dedicated hardware device.

Upon reading this disclosure, those of skill in the art will appreciate still additional alternative structural and functional designs through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context unless otherwise explicitly stated.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

What is claimed is:

1. A method for capturing an object in a cavity comprising:
controlling a first robotic arm of a robotic system to advance an endoscope into the cavity comprising the object, the first robotic arm being coupled to the endoscope;
controlling a second robotic arm of the robotic system to advance a basket tool through a working channel of the endoscope to position a basket of the basket tool within the cavity, the basket being associated with a distal end of the basket tool, the second robotic arm being configured to control the basket tool;
controlling the second robotic arm to expand the basket to an at least partially expanded state;
positioning a central portion of the basket in the at least partially expanded state at a first position to enclose the object;
controlling at least one of the first robotic arm or the second robotic arm to collapse the basket while maintaining the central portion of the basket at the first position; and
upon the basket, retracting the basket tool into a sheath associated with the endoscope.

2. The method of claim 1 wherein controlling at least one of the first robotic arm or the second robotic arm to collapse the basket while maintaining the central portion of the basket at the first position comprises:
advancing the endoscope further into the cavity.

3. The method of claim 1 wherein controlling at least one of the first robotic arm or the second robotic arm to collapse the basket while maintaining the central portion of the basket at the first position comprises:
actuating capstans to spool pull wires thereby decreasing the size of the basket within the cavity.

4. The method of claim 1 wherein controlling the first robotic arm of the robotic system to advance the endoscope into the cavity comprising the object comprises:
controlling motion of at least one of the sheath or a leader of the endo scope.

5. The method of claim 4 wherein controlling the second robotic arm of the robotic system to advance the basket tool through the working channel of the endoscope to position the basket of the basket tool within the cavity comprises:
controlling motion of the basket tool along a long axis of the basket tool and endoscope.

6. The method of claim 4 wherein positioning the central portion of the basket in the at least partially expanded state at the first position to enclose the object comprises:
actuating at least one of a tool base or the second robotic arm to control motion of the basket tool along a long axis of the basket tool and endoscope.

7. The method of claim 6 wherein controlling at least one of the first robotic arm or the second robotic arm to collapse the basket while maintaining the central portion of the basket at the first position comprises:
moving at least one of the leader or the basket tool.

8. The method of claim 6 wherein controlling at least one of the first robotic arm or the second robotic arm to collapse the basket while maintaining the central portion of the basket at the first position comprises:
moving at least one of the sheath or leader relative to each other.

9. The method of claim 1 wherein controlling the first robotic arm of the robotic system to advance the endoscope into the cavity comprising the object comprises:
actuating an instrument base coupled to the endoscope.

10. The method of claim 9 wherein controlling the second robotic arm of the robotic system to advance the basket tool through the working channel of the endoscope to position the basket of the basket tool within the cavity comprises:
actuating a tool base coupled to the basket tool, wherein the second robotic arm is configured to control motion of the basket tool along a long axis of the basket tool and the endoscope.

11. The method of claim 9 wherein positioning the central portion of the basket in the at least partially expanded state at the first position to enclose the object comprises:
actuating a tool base coupled to the basket tool, wherein the second robotic arm is configured to control motion of the basket tool along a long axis of the basket tool and the endoscope.

12. The method of claim 11 wherein controlling at least one of the first robotic arm or the second robotic arm to collapse the basket while maintaining the central portion of the basket at the first position comprises:
actuating at least one of the tool base or the second robotic arm to retract the basket tool into the endoscope; and
actuating at least one of the instrument base or the first robotic arm to move the endoscope further into the cavity.

13. The method of claim 11 wherein controlling at least one of the first robotic arm or the second robotic arm to collapse the basket while maintaining the central portion of the basket at the first position comprises:
actuating at least one of the tool base, the instrument base, the first robotic arm or the second robotic arm to move the basket tool and the endoscope in opposite directions relative to each other.

14. The method of claim 1,
wherein the endoscope comprises a sheath component coupled to the first robotic arm, and a leaderscope coupled to the second robotic arm.

15. The method of claim 14 wherein controlling the second robotic arm of the robotic system to advance the basket tool through the working channel of the endoscope to position the basket of the basket tool within the cavity comprises:
controlling motion of the basket tool along a long axis of the basket tool and the endoscope.

16. The method of claim 14 wherein positioning the central portion of the basket in the at least partially expanded state at the first position to enclose the object comprises:
actuating a tool base coupled to the basket tool.

17. The method of claim 16 wherein controlling at least one of the first robotic arm or the second robotic arm to collapse the basket while maintaining the central portion of the basket at the first position comprises:
actuating the tool base to retract the basket tool into the endoscope; and
actuating at least one of the first robotic arm or the second robotic arm to move the endoscope further into the cavity.

18. The method of claim 16 wherein controlling at least one of the first robotic arm or the second robotic arm to collapse the basket while maintaining the central portion of the basket at the first position comprises:
actuating at least one of the tool base, the first robotic arm, or the second robotic arm to move the basket tool and the endoscope in opposite directions relative to each other.

19. The method of claim 1 further comprising:
passing an optical fiber or a laser through the working channel of the basket tool; and
activating the optical fiber or laser to perform lithotripsy on the object to break the object apart.

20. The method of claim 1 further comprising:
passing a mechanical drill through the working channel of the basket tool; and
activating the mechanical drill in contact with the object to break the object apart.

21. The method of claim 1 further comprising:
passing a chisel through the working channel of the basket tool; and
activating the chisel in contact with the object to break the object apart.

22. The method of claim 1 further comprising:
passing fluid through the working channel of the basket tool towards the object to break the object apart.

23. The method of claim 1 wherein the object is at least one from the group consisting of: a kidney stone or a bladder stone, a stone formed from at least one of calcium, magnesium, ammonia, uric acid, and cysteine.

24. The method of claim 1 wherein the cavity is a kidney of a patient or a calyx within the kidney of the patient.

25. The method of claim 1 wherein the endoscope is a ureteroscope.

26. A system comprising:
an endoscope including a working channel;
a first robotic arm configured to couple to the endoscope and configured to advance the endoscope into a cavity including an object; and
a second robotic arm configured to:
advance a basket tool through the working channel of the endoscope to position a basket of the basket tool within a cavity, the basket being associated with a distal end of the basket tool; and
expand the basket to an at least partially open state;
wherein at least one of the first robotic arm or the second robotic arm is configured to:
position a central portion of the basket at a first position to enclose the object;
collapse the basket while maintaining the central portion of the basket at the first position; and
upon collapsing the basket, retract the basket tool into a sheath to remove the object from the cavity.

* * * * *